United States Patent
Schreck et al.

(10) Patent No.: US 10,390,836 B2
(45) Date of Patent: *Aug. 27, 2019

(54) METHOD AND SYSTEM FOR TREATING ANEURYSMS

(71) Applicant: ENDOLOGIX, INC., Irvine, CA (US)

(72) Inventors: Stefan Schreck, Fallbrook, CA (US); Jason Fox, San Carlos, CA (US)

(73) Assignee: Endologix, Inc., Irvine, CA (US)

( * ) Notice: Subject to any disclaimer, the term of this patent is extended or adjusted under 35 U.S.C. 154(b) by 257 days.

This patent is subject to a terminal disclaimer.

(21) Appl. No.: 15/205,365

(22) Filed: Jul. 8, 2016

(65) Prior Publication Data

US 2017/0007263 A1   Jan. 12, 2017

Related U.S. Application Data

(63) Continuation of application No. 13/441,762, filed on Apr. 6, 2012, now Pat. No. 9,415,195.

(Continued)

(51) Int. Cl.
*A61F 2/82* (2013.01)
*A61B 17/12* (2006.01)
(Continued)

(52) U.S. Cl.
CPC ........ *A61B 17/12036* (2013.01); *A61B 6/481* (2013.01); *A61B 6/504* (2013.01);
(Continued)

(58) Field of Classification Search
CPC .. A61F 2/95; A61F 2/954; A61F 2/958; A61F 2002/061; A61F 2250/0097; A61M 25/104
See application file for complete search history.

(56) References Cited

U.S. PATENT DOCUMENTS

| 4,565,738 A | 1/1986 | Purdy |
| 4,638,803 A | 1/1987 | Rand |

(Continued)

FOREIGN PATENT DOCUMENTS

| DE | 4010975 A1 | 10/1991 |
| EP | 95302708.3 | 11/1995 |

(Continued)

OTHER PUBLICATIONS

International Search Report and the Written Opinion of the International Searching Authority, Issued in PCT/US2012/032612 dated Jul. 25, 2012, 13 pages.

(Continued)

*Primary Examiner* — Anh T Dang
(74) *Attorney, Agent, or Firm* — Foley & Lardner LLP

(57) ABSTRACT

Methods for treatment of aneurysms using a sequential manifold console to deploy multiple filling structures are provided herein. In one aspect, aneurysms are treated by simultaneously filling two double-walled filling structure using a sequential manifold console to guide a user in the steps to be followed in the procedure and to reliably achieve a consistent and durable aneurysmal treatment using a curable medium. The structures may be delivered over balloon deployment mechanisms in order to shape and open tubular lumens therethrough. Pairs of filling structures delivered to the aneurysm from different access openings of a patient can be simultaneously prepared and pressurized from a single treatment console when treating abdominal aortic aneurysms using the described systems and methods.

20 Claims, 38 Drawing Sheets

Related U.S. Application Data

(60) Provisional application No. 61/473,051, filed on Apr. 7, 2011, provisional application No. 61/472,209, filed on Apr. 6, 2011.

(51) Int. Cl.
  *A61F 2/07* (2013.01)
  *A61F 2/90* (2013.01)
  *A61B 6/00* (2006.01)
  *A61M 25/09* (2006.01)
  *A61M 25/10* (2013.01)
  *A61B 17/00* (2006.01)

(52) U.S. Cl.
  CPC .. *A61B 17/12118* (2013.01); *A61B 17/12136* (2013.01); *A61B 17/12186* (2013.01); *A61F 2/07* (2013.01); *A61F 2/90* (2013.01); *A61M 25/09* (2013.01); *A61M 25/104* (2013.01); *A61M 25/1018* (2013.01); *A61B 2017/00659* (2013.01); *A61B 2017/1205* (2013.01); *A61F 2002/075* (2013.01); *A61F 2002/077* (2013.01); *A61F 2230/0034* (2013.01)

(56) References Cited

U.S. PATENT DOCUMENTS

| | | |
|---|---|---|
| 4,641,653 A | 2/1987 | Rockey |
| 4,704,126 A | 11/1987 | Baswell |
| 4,710,192 A | 12/1987 | Liotta |
| 4,728,328 A | 3/1988 | Hughes et al. |
| 4,731,073 A | 3/1988 | Robinson |
| 4,733,665 A | 3/1988 | Palmaz |
| 4,743,258 A | 5/1988 | Ikada |
| 4,763,654 A | 8/1988 | Jang |
| 4,856,516 A | 8/1989 | Hillstead |
| 4,858,264 A | 8/1989 | Reinhart |
| 4,892,544 A | 1/1990 | Frisch |
| 4,936,057 A | 6/1990 | Rhoades |
| 4,976,692 A | 12/1990 | Atad |
| 5,002,532 A | 3/1991 | Gaiser |
| 5,074,845 A | 12/1991 | Miraki |
| 5,085,635 A | 2/1992 | Cragg |
| 5,104,404 A | 4/1992 | Wolff |
| 5,108,417 A | 4/1992 | Sawyer |
| 5,122,154 A | 6/1992 | Rhodes |
| 5,133,732 A | 7/1992 | Wiktor |
| 5,139,480 A | 8/1992 | Hickle |
| 5,156,620 A | 10/1992 | Pigott |
| 5,195,984 A | 3/1993 | Schatz |
| 5,199,226 A | 4/1993 | Rose |
| 5,217,484 A | 6/1993 | Marks |
| 5,222,970 A | 6/1993 | Reeves |
| 5,234,437 A | 8/1993 | Sepetka |
| 5,242,399 A | 9/1993 | Lau |
| 5,250,071 A | 10/1993 | Palermo |
| 5,261,916 A | 11/1993 | Engelson |
| 5,263,964 A | 11/1993 | Purdy |
| 5,292,331 A | 3/1994 | Boneau |
| 5,314,444 A | 5/1994 | Gianturco |
| 5,316,023 A | 5/1994 | Palmaz et al. |
| 5,330,528 A | 7/1994 | Lazim |
| 5,334,217 A | 8/1994 | Das |
| 5,350,397 A | 9/1994 | Palermo |
| 5,352,199 A | 10/1994 | Tower |
| 5,375,612 A | 12/1994 | Cottenceau |
| 5,383,892 A | 1/1995 | Cardon |
| 5,421,955 A | 6/1995 | Lau |
| 5,423,849 A | 6/1995 | Engelson |
| 5,425,739 A | 6/1995 | Jessen |
| 5,425,744 A | 6/1995 | Fagan |
| 5,441,510 A | 8/1995 | Simpson |
| 5,441,515 A | 8/1995 | Khosravi |
| 5,443,477 A | 8/1995 | Marin |
| 5,443,496 A | 8/1995 | Schwartz |
| 5,449,373 A | 9/1995 | Pinchasik |
| 5,485,667 A | 1/1996 | Kleshinski |
| 5,494,029 A | 2/1996 | Lane |
| 5,496,277 A | 3/1996 | Termin |
| 5,507,767 A | 4/1996 | Maeda |
| 5,507,769 A | 4/1996 | Marin et al. |
| 5,507,771 A | 4/1996 | Gianturco |
| 5,514,115 A | 5/1996 | Frantzen |
| 5,514,154 A | 5/1996 | Lau |
| 5,522,882 A | 6/1996 | Gaterud |
| 5,530,528 A | 6/1996 | Houki et al. |
| 5,531,741 A | 7/1996 | Barbacci |
| 5,534,024 A | 7/1996 | Rogers et al. |
| 5,545,210 A | 8/1996 | Hess |
| 5,549,662 A | 8/1996 | Fordenbacher |
| 5,549,663 A | 8/1996 | Cottone, Jr. |
| 5,554,181 A | 9/1996 | Das |
| 5,562,641 A | 10/1996 | Flomenblit |
| 5,562,698 A | 10/1996 | Parker |
| 5,562,728 A | 10/1996 | Lazarus |
| 5,569,295 A | 10/1996 | Lam |
| 5,578,074 A | 11/1996 | Mirigian |
| 5,578,149 A | 11/1996 | De Scheerder |
| 5,591,195 A | 1/1997 | Taheri |
| 5,591,223 A | 1/1997 | Lock |
| 5,591,226 A | 1/1997 | Trerotola |
| 5,591,228 A | 1/1997 | Edoga |
| 5,591,230 A | 1/1997 | Horn |
| 5,593,417 A | 1/1997 | Rhodes |
| 5,601,600 A | 2/1997 | Ton |
| 5,603,721 A | 2/1997 | Lau |
| 5,605,530 A | 2/1997 | Fischell |
| 5,607,442 A | 3/1997 | Fischell |
| 5,607,445 A | 3/1997 | Summers |
| 5,607,468 A | 3/1997 | Rogers |
| 5,609,605 A | 3/1997 | Marshall |
| 5,617,878 A | 4/1997 | Taheri |
| 5,618,299 A | 4/1997 | Khosravi |
| 5,624,411 A | 4/1997 | Tuch |
| 5,630,840 A | 5/1997 | Mayer |
| 5,632,760 A | 5/1997 | Sheiban |
| 5,632,762 A | 5/1997 | Myler |
| 5,632,763 A | 5/1997 | Glastra |
| 5,632,771 A | 5/1997 | Boatman |
| D380,266 S | 6/1997 | Boatman |
| 5,634,941 A | 6/1997 | Winston |
| 5,636,641 A | 6/1997 | Fariabi |
| D380,831 S | 7/1997 | Kavteladze |
| 5,662,614 A | 9/1997 | Edoga |
| 5,665,117 A | 9/1997 | Rhodes |
| 5,674,241 A | 10/1997 | Bley |
| 5,676,697 A | 10/1997 | McDonald |
| 5,683,449 A | 11/1997 | Marcade |
| 5,690,643 A | 11/1997 | WiJay |
| 5,693,038 A | 12/1997 | Suzuki et al. |
| 5,693,067 A | 12/1997 | Purdy |
| 5,693,088 A | 12/1997 | Lazarus |
| 5,697,971 A | 12/1997 | Fischell |
| 5,709,707 A | 1/1998 | Lock |
| 5,718,713 A | 2/1998 | Frantzen |
| 5,723,004 A | 3/1998 | Dereume |
| 5,725,568 A | 3/1998 | Hastings |
| 5,725,572 A | 3/1998 | Lam |
| 5,728,068 A | 3/1998 | Leone |
| 5,728,131 A | 3/1998 | Frantzen |
| 5,728,158 A | 3/1998 | Lau |
| 5,733,303 A | 3/1998 | Israel et al. |
| 5,735,892 A | 4/1998 | Myers |
| 5,735,893 A | 4/1998 | Lau |
| 5,741,327 A | 4/1998 | Frantzen |
| 5,741,333 A | 4/1998 | Frid |
| 5,746,691 A | 5/1998 | Frantzen |
| 5,755,769 A | 5/1998 | Richard |
| 5,755,773 A | 5/1998 | Evans et al. |
| 5,755,778 A | 5/1998 | Kleshinski |
| 5,766,151 A | 6/1998 | Valley et al. |
| 5,766,238 A | 6/1998 | Lau |
| 5,769,882 A | 6/1998 | Fogarty et al. |
| 5,776,114 A | 7/1998 | Frantzen |

(56) References Cited

U.S. PATENT DOCUMENTS

| | | |
|---|---|---|
| 5,776,161 A | 7/1998 | Globerman |
| 5,782,907 A | 7/1998 | Frantzen |
| 5,785,679 A | 7/1998 | Abolfathi et al. |
| 5,788,626 A | 8/1998 | Thompson |
| 5,797,953 A | 8/1998 | Tekulve |
| 5,800,393 A | 9/1998 | Sahota |
| 5,800,512 A | 9/1998 | Lentz et al. |
| 5,800,514 A | 9/1998 | Nunez |
| 5,800,525 A | 9/1998 | Bachinski |
| 5,807,404 A | 9/1998 | Richter |
| 5,810,872 A | 9/1998 | Kanesaka |
| 5,824,036 A | 10/1998 | Lauterjung |
| 5,824,037 A | 10/1998 | Fogarty et al. |
| 5,824,040 A | 10/1998 | Cox |
| 5,824,049 A | 10/1998 | Ragheb |
| 5,824,054 A | 10/1998 | Khosravi et al. |
| 5,824,056 A | 10/1998 | Rosenberg |
| 5,827,321 A | 10/1998 | Roubin |
| 5,836,966 A | 11/1998 | St. Germain |
| 5,843,160 A | 12/1998 | Rhodes |
| 5,843,175 A | 12/1998 | Frantzen |
| 5,846,246 A | 12/1998 | Dirks |
| 5,846,261 A | 12/1998 | Kotula et al. |
| 5,849,037 A | 12/1998 | Frid |
| 5,860,998 A | 1/1999 | Robinson |
| 5,863,627 A | 1/1999 | Szycher |
| 5,867,762 A | 2/1999 | Rafferty et al. |
| 5,868,685 A | 2/1999 | Powell et al. |
| 5,868,708 A | 2/1999 | Hart |
| 5,868,782 A | 2/1999 | Frantzen |
| 5,871,537 A | 2/1999 | Holman |
| 5,873,907 A | 2/1999 | Frantzen |
| 5,876,448 A | 3/1999 | Thompson et al. |
| 5,879,381 A | 3/1999 | Moriuchi |
| 5,888,660 A | 3/1999 | Landoni et al. |
| 5,902,332 A | 5/1999 | Schatz |
| 5,919,224 A | 7/1999 | Thompson |
| 5,928,279 A | 7/1999 | Shannon et al. |
| 5,931,866 A | 8/1999 | Frantzen |
| 5,944,750 A | 8/1999 | Tanner |
| 5,947,991 A | 9/1999 | Cowan |
| 5,948,184 A | 9/1999 | Frantzen |
| 5,976,178 A | 11/1999 | Goldsteen et al. |
| 5,984,955 A | 11/1999 | Wisselink |
| 5,994,750 A | 11/1999 | Yagi |
| 6,007,573 A | 12/1999 | Wallace |
| 6,015,431 A | 1/2000 | Thornton |
| 6,022,359 A | 2/2000 | Frantzen |
| 6,033,434 A | 3/2000 | Borghi |
| 6,042,606 A | 3/2000 | Frantzen |
| 6,056,776 A | 5/2000 | Lau |
| 6,066,167 A | 5/2000 | Lau |
| 6,066,168 A | 5/2000 | Lau |
| 6,083,259 A | 7/2000 | Frantzen |
| 6,093,199 A | 7/2000 | Brown |
| 6,099,548 A | 8/2000 | Taheri |
| 6,110,198 A | 8/2000 | Fogarty et al. |
| 6,123,715 A | 9/2000 | Amplatz |
| 6,123,722 A | 9/2000 | Fogarty |
| 6,124,523 A | 9/2000 | Banas et al. |
| 6,132,457 A | 10/2000 | Chobotov |
| 6,152,144 A | 11/2000 | Lesh et al. |
| 6,152,943 A | 11/2000 | Sawhney |
| 6,168,592 B1 | 1/2001 | Kupiecki et al. |
| 6,187,033 B1 | 2/2001 | Schmitt |
| 6,187,034 B1 | 2/2001 | Frantzen |
| 6,190,402 B1 | 2/2001 | Horton et al. |
| 6,190,406 B1 | 2/2001 | Duerig et al. |
| 6,193,745 B1 | 2/2001 | Fogarty et al. |
| 6,196,230 B1 | 3/2001 | Hall et al. |
| 6,203,732 B1 | 3/2001 | Clubb |
| 6,214,022 B1 | 4/2001 | Taylor et al. |
| 6,231,562 B1 | 5/2001 | Khosravi et al. |
| 6,235,050 B1 | 5/2001 | Quiachon et al. |
| 6,241,761 B1 | 6/2001 | Villafana |
| 6,254,633 B1 | 7/2001 | Pinchuk et al. |
| 6,261,305 B1 | 7/2001 | Marotta et al. |
| 6,280,466 B1 | 8/2001 | Kugler |
| 6,283,991 B1 | 9/2001 | Cox et al. |
| 6,290,722 B1 | 9/2001 | Wang |
| 6,290,731 B1 | 9/2001 | Solovay et al. |
| 6,293,958 B1 | 9/2001 | Berry et al. |
| 6,293,960 B1 | 9/2001 | Ken |
| 6,296,603 B1 | 10/2001 | Turnlund et al. |
| 6,299,597 B1 | 10/2001 | Buscemi et al. |
| 6,299,604 B1 | 10/2001 | Ragheb |
| 6,312,462 B1 | 11/2001 | McDermott et al. |
| 6,312,463 B1 | 11/2001 | Rourke et al. |
| 6,325,816 B1 | 12/2001 | Fulton, III |
| 6,325,819 B1 | 12/2001 | Pavcnik et al. |
| 6,331,184 B1 | 12/2001 | Abrams |
| 6,331,191 B1 | 12/2001 | Chobotov |
| 6,334,869 B1 | 1/2002 | Leonhardt et al. |
| 6,344,056 B1 | 2/2002 | Dehdashtian |
| 6,375,675 B2 | 4/2002 | Dehdashtian et al. |
| 6,395,019 B2 | 5/2002 | Chobotov |
| 6,409,757 B1 | 6/2002 | Trout, III et al. |
| 6,432,131 B1 | 8/2002 | Ravenscroft |
| 6,451,047 B2 | 9/2002 | McCrea |
| 6,463,317 B1 | 10/2002 | Kucharczyk et al. |
| 6,506,204 B2 | 1/2003 | Mazzocchi |
| 6,527,799 B2 | 3/2003 | Shanley |
| 6,544,276 B1 | 4/2003 | Azizi |
| 6,547,804 B2 | 4/2003 | Porter et al. |
| 6,554,858 B2 | 4/2003 | Dereume et al. |
| 6,576,007 B2 | 6/2003 | Dehdashtian et al. |
| 6,579,301 B1 | 6/2003 | Bales |
| 6,592,614 B2 | 7/2003 | Lenker et al. |
| 6,613,037 B2 | 9/2003 | Khosravi et al. |
| 6,645,242 B1 | 11/2003 | Quinn |
| 6,656,214 B1 | 12/2003 | Fogarty et al. |
| 6,656,220 B1 | 12/2003 | Gomez et al. |
| 6,663,607 B2 | 12/2003 | Slaikeu et al. |
| 6,663,667 B2 | 12/2003 | Dehdashtian et al. |
| 6,679,300 B1 | 1/2004 | Sommer et al. |
| 6,682,546 B2 | 1/2004 | Amplatz |
| 6,692,486 B2 | 2/2004 | Jaafar et al. |
| 6,695,833 B1 | 2/2004 | Frantzen |
| 6,729,356 B1 | 5/2004 | Baker et al. |
| 6,730,119 B1 | 5/2004 | Smalling |
| 6,733,521 B2 | 5/2004 | Chobotov |
| 6,761,733 B2 | 7/2004 | Chobotov |
| 6,773,454 B2 | 8/2004 | Wholey et al. |
| 6,776,771 B2 | 8/2004 | Van Moorlegem et al. |
| 6,827,735 B2 | 12/2004 | Greenberg |
| 6,843,803 B2 | 1/2005 | Ryan et al. |
| 6,878,161 B2 | 4/2005 | Lenker |
| 6,878,164 B2 | 4/2005 | Kujawski |
| 6,887,268 B2 | 5/2005 | Butaric et al. |
| 6,918,926 B2 | 7/2005 | Letort |
| 6,945,989 B1 | 9/2005 | Betelia et al. |
| 6,958,051 B2 | 10/2005 | Hart et al. |
| 6,960,227 B2 | 11/2005 | Jones et al. |
| 7,022,100 B1 | 4/2006 | Aboul-Hosn et al. |
| 7,105,012 B2 | 9/2006 | Trout, III |
| 7,112,217 B1 | 9/2006 | Kugler et al. |
| 7,122,052 B2 | 10/2006 | Greenhalgh |
| 7,131,991 B2 | 11/2006 | Zarins et al. |
| 7,147,661 B2 | 12/2006 | Chobotov et al. |
| 7,175,651 B2 | 2/2007 | Kerr |
| 7,229,472 B2 | 6/2007 | DePalma et al. |
| 7,314,483 B2 | 1/2008 | Landau et al. |
| 7,326,237 B2 | 2/2008 | Depalma et al. |
| 7,435,253 B1 | 10/2008 | Hartley et al. |
| 7,530,988 B2 | 5/2009 | Evans et al. |
| 7,666,220 B2 | 2/2010 | Evans et al. |
| 7,682,383 B2 | 3/2010 | Robin |
| 7,708,773 B2 | 5/2010 | Pinchuk et al. |
| 7,790,273 B2 | 9/2010 | Lee et al. |
| 7,828,838 B2 | 11/2010 | Bolduc et al. |
| 7,951,448 B2 | 5/2011 | Lee et al. |
| 9,415,195 B2 | 8/2016 | Schreck et al. |
| 2001/0020184 A1 | 9/2001 | Dehdashtian et al. |
| 2001/0027337 A1 | 10/2001 | Di Caprio |

(56) References Cited

U.S. PATENT DOCUMENTS

| | | |
|---|---|---|
| 2001/0027338 A1 | 10/2001 | Greenberg |
| 2001/0044655 A1 | 11/2001 | Patnaik et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0045931 A1 | 4/2002 | Sogard et al. |
| 2002/0052643 A1 | 5/2002 | Wholey et al. |
| 2002/0077594 A1 | 6/2002 | Chien et al. |
| 2002/0151953 A1 | 10/2002 | Chobotov |
| 2002/0151956 A1 | 10/2002 | Chobotov |
| 2002/0151958 A1 | 10/2002 | Chuter |
| 2002/0156518 A1 | 10/2002 | Tehrani |
| 2002/0165521 A1 | 11/2002 | Cioanta et al. |
| 2002/0169497 A1 | 11/2002 | Wholey et al. |
| 2002/0183629 A1 | 12/2002 | Fitz |
| 2003/0004560 A1 | 1/2003 | Chobotov |
| 2003/0009132 A1 | 1/2003 | Schwartz et al. |
| 2003/0014075 A1 | 1/2003 | Rosenbluth et al. |
| 2003/0028209 A1 | 2/2003 | Teoh et al. |
| 2003/0036745 A1 | 2/2003 | Khosravi et al. |
| 2003/0051735 A1 | 3/2003 | Pavcnik et al. |
| 2003/0074056 A1 | 4/2003 | Killion et al. |
| 2003/0078647 A1 | 4/2003 | Vallana et al. |
| 2003/0079752 A1 | 5/2003 | Hart et al. |
| 2003/0093145 A1 | 5/2003 | Lawrence-Brown et al. |
| 2003/0130720 A1 | 7/2003 | DePalma et al. |
| 2003/0130725 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov et al. |
| 2003/0220649 A1 | 11/2003 | Bao et al. |
| 2003/0225446 A1 | 12/2003 | Hartley |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0091543 A1 | 5/2004 | Bell et al. |
| 2004/0098096 A1 | 5/2004 | Eton |
| 2004/0116997 A1 | 6/2004 | Taylor et al. |
| 2004/0147811 A1 | 7/2004 | Diederich et al. |
| 2004/0153025 A1 | 8/2004 | Seifert et al. |
| 2004/0167607 A1 | 8/2004 | Frantzen |
| 2004/0193245 A1 | 9/2004 | Deem et al. |
| 2004/0204755 A1 | 10/2004 | Robin |
| 2004/0215172 A1 | 10/2004 | Chu et al. |
| 2004/0215316 A1 | 10/2004 | Smalling |
| 2004/0220522 A1 | 11/2004 | Briscoe et al. |
| 2004/0243057 A1 | 12/2004 | Vinten-Johansen et al. |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0065592 A1 | 3/2005 | Holzer |
| 2005/0090804 A1 | 4/2005 | Chobotov et al. |
| 2005/0096731 A1 | 5/2005 | Looi et al. |
| 2005/0215989 A1 | 9/2005 | Abboud et al. |
| 2005/0245891 A1 | 11/2005 | McCormick et al. |
| 2005/0251251 A1 | 11/2005 | Cribier |
| 2006/0015173 A1 | 1/2006 | Clifford et al. |
| 2006/0025853 A1 | 2/2006 | Evans et al. |
| 2006/0074481 A1 | 4/2006 | Vardi et al. |
| 2006/0135942 A1 | 6/2006 | Fernandes et al. |
| 2006/0142836 A1 | 6/2006 | Hartley et al. |
| 2006/0155369 A1 | 7/2006 | Edwin et al. |
| 2006/0161244 A1 | 7/2006 | Seguin |
| 2006/0184109 A1 | 8/2006 | Gobel |
| 2006/0206197 A1 | 9/2006 | Morsi |
| 2006/0212112 A1 | 9/2006 | Evans et al. |
| 2006/0265043 A1 | 11/2006 | Mandrusov et al. |
| 2006/0292206 A1 | 12/2006 | Kim et al. |
| 2007/0032850 A1 | 2/2007 | Ruiz et al. |
| 2007/0043420 A1 | 2/2007 | Lostetter |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0150041 A1 | 6/2007 | Evans et al. |
| 2007/0162106 A1 | 7/2007 | Evans et al. |
| 2007/0162109 A1 | 7/2007 | Davila et al. |
| 2007/0208416 A1 | 9/2007 | Burpee et al. |
| 2007/0276477 A1 | 11/2007 | Lee et al. |
| 2008/0039923 A1 | 2/2008 | Taylor et al. |
| 2008/0154368 A1 | 6/2008 | Justis et al. |
| 2008/0228259 A1 | 9/2008 | Chu |
| 2008/0294237 A1 | 11/2008 | Chu |
| 2009/0099649 A1 | 4/2009 | Chobotov et al. |
| 2009/0198267 A1 | 8/2009 | Evans et al. |
| 2009/0209855 A1 | 8/2009 | Drilling et al. |
| 2009/0216125 A1 | 8/2009 | Lenker |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0036360 A1 | 2/2010 | Herbowy et al. |
| 2010/0106087 A1 | 4/2010 | Evans et al. |
| 2010/0217383 A1 | 8/2010 | Leonhardt et al. |
| 2012/0016456 A1 | 1/2012 | Herbowy et al. |
| 2012/0259406 A1 | 10/2012 | Schreck et al. |

FOREIGN PATENT DOCUMENTS

| | | |
|---|---|---|
| EP | 1325717 | 7/2003 |
| EP | 1903985 | 4/2008 |
| FR | 2834199 A1 | 7/2003 |
| JP | H04-322665 A1 | 11/1992 |
| JP | 2003-525692 | 9/2003 |
| JP | 2004-537353 A | 12/2004 |
| JP | 2005-505380 A | 2/2005 |
| JP | 2005-532120 A | 10/2005 |
| JP | 2008-510502 A | 4/2008 |
| WO | 97/17912 A1 | 5/1997 |
| WO | 97/19653 | 6/1997 |
| WO | 98/53761 A1 | 12/1998 |
| WO | 99/00073 A1 | 1/1999 |
| WO | 99/44539 A2 | 9/1999 |
| WO | 00/29060 A2 | 5/2000 |
| WO | 00/51522 | 9/2000 |
| WO | 01/21108 | 3/2001 |
| WO | 01/66038 | 9/2001 |
| WO | 02/078569 A2 | 10/2002 |
| WO | 02/083038 A2 | 10/2002 |
| WO | 02/102282 | 12/2002 |
| WO | 03/007785 A2 | 1/2003 |
| WO | 03/032869 A1 | 4/2003 |
| WO | 03/037222 A2 | 5/2003 |
| WO | 03/053288 A1 | 7/2003 |
| WO | 2004/004603 A1 | 1/2004 |
| WO | 2004/026183 A2 | 4/2004 |
| WO | 2004/026183 A3 | 4/2004 |
| WO | 2004/037116 A2 | 5/2004 |
| WO | 2004/037116 A3 | 5/2004 |
| WO | 2004/045393 A2 | 6/2004 |
| WO | 2006/012567 A2 | 2/2006 |
| WO | 2006/012567 A3 | 2/2006 |
| WO | 2006/116725 A2 | 11/2006 |
| WO | 2007/008600 A2 | 1/2007 |
| WO | 2007/142916 A2 | 12/2007 |

OTHER PUBLICATIONS

Patrick W. Serruys and Michael JB Kutryk; Handbook of Coronary Stents, Second Edition; 1998; pp. 45, 55, 78, 103, 112, 132, 158, 174, 185, 190, 207, 215, 230, 239; Martin Dunitz; UK.

Journal of Endovascular Therapy; Apr. 2000; pp. 111, 114, 132-140; vol. 7' No. 2; International Society of Endovascular Specialists; Phoenix, AZ.

Gilling-Smith, "Stent Graft Migration After Endovascular Aneurysm Repair," presented at 25th International Charing Cross Symposium, Apr. 13, 2003 [Power Point Presentation and Transcript], 56 pages total.

Carmi et al., "Endovascular stent-graft adapted to the endoluminal environment: prototype of a new endoluminal approach," J Endovasc Ther. Jun. 2002;9(3):380-381.

Donayre et al., "Fillable Endovascular Aneurysm Repair," Endovascular Today, pp. 64-66, Jan. 2009.

(56) References Cited

OTHER PUBLICATIONS

International Search Report and Written Opinion of PCT Application No. PCT/US2009/046310, dated Jul. 29, 2009, 9 pages total.
International Search Report of PCT/US 06/16403, dated Aug. 7, 2007. 2 pages.
International Search Report and Written Opinion of PCT Application No. PCT/US2006/062257, dated Jan. 18, 2008. 7 pages total.
International Search Report and Written Opinion of PCT Application No. PCT/US07/69671, dated Jul. 7, 2008, 9 pages.
International Search Report and Written Opinion of PCT Application No. PCT/US09/34136, D dated Apr. 8, 2009, 16 pages total.
U.S. Appl. No. 12/371,087, filed Feb. 13, 2009, first named inventor: K.T. Venkateswara Rao.
International Search Report and Written Opinion of PCT Application No. PCT/US09/41718, dated Jun. 22, 2009, 23 pages total.
Supplementary European Search Report and Search Opinion of EP Patent Application No. 05773726, dated Apr. 23, 2010, 6 pages total.
The International Search Report of the International Searching Authority for Application No. PCT/US2012/021878, dated May 23, 2012, 4 pages.
The Written Opinion, including the search, of the International Searching Authority for Application No. PCT/US2012/021878, dated May 23, 2012, 9 pages.
Extended European search report of corresponding EP Application No. 06751879.5, dated Apr. 16, 2013. 9 pages.
European Search Report and Search Opinion of EP Patent Application No. 06774540.6, dated Mar. 30, 2010, 6 pages total.
EP report, dated Nov. 7, 2013, of corresponding EP Application No. 09733719.0.
Search report dated Oct. 17, 2013 of corresponding PCT/US2012/032612.
International Preliminary Report on Patentability PCT/US2012/021878 dated Aug. 1, 2013.
Report of European Patent Application No. 06850439.8 dated May 15, 2013.
Report for European Patent Application No. 06850439.8.
Examination report for JP Application. No. 2008-547709 dated Dec. 13, 2011.
International Search Report and Written Opinion of PCT Application No. PCT/US2009/046308, dated Nov. 17, 2009, 12 pages total.
Examination Report of corresponding Japanese Application No. 2011-512667, dated Jun. 18, 2013.
International Preliminary Report on Patentability and Written Opinion of the International Searching Authority, Issued in PCT/US2010/061621 dated Jul. 12, 2012, 7 pages.
PCT International Search Report and Written Opinion dated Feb. 28, 2011 for PCT Application No. PCT/US2010/61621. 11 pages.
U.S. Appl. No. 60/855,889, filed Oct. 31, 2006; first named inventor: Steven L. Herbowy.
U.S. Appl. No. 12/429,474, filed Apr. 24, 2009; first named inventor: Steven L. Herbowy.
U.S. Appl. No. 61/052,059, filed May 9, 2008; first named inventor: Gwendolyn A. Watanabe.
William Tanski, Mark Fillinger. Outcomes of original and low-permeability Gore Excluder endoprosthesis for endovascular abdominal aortic aneurysm repair. Journal of Vascular Surgery. Feb. 2007. p. 243-249.
Susan M. Trocciola et al. The development of endotension is associated with increased transmission of pressure and serous components in porous expanded polytetrafluoroethylene stent-grafts: Characterization using a canine model. Journal of Vascular Surgery. Jan. 2006. p. 109-116.
Shan-e-ali Haider et al. Sac behavior after aneurysm treatment with the Gore Excluder low-permeability aortic endoprosthesis: 12-month comparison to the original Excluder device. Journal of Vascular Surgery. vol. 44, No. 4. 694-700. Oct. 2006.
First Office Action of Chinese Application No. 201280027681.X, dated Mar. 18, 2015 (18 pages).
U.S. Office Action dated Apr. 6, 2018, from U.S. Appl. No. 14/717,938.
Notice of Allowance dated Mar. 4, 2019, from U.S. Appl. No. 14/717,938.
Non-Final Office Action dated Oct. 4, 2018, from U.S. Appl. No. 14/717,938.

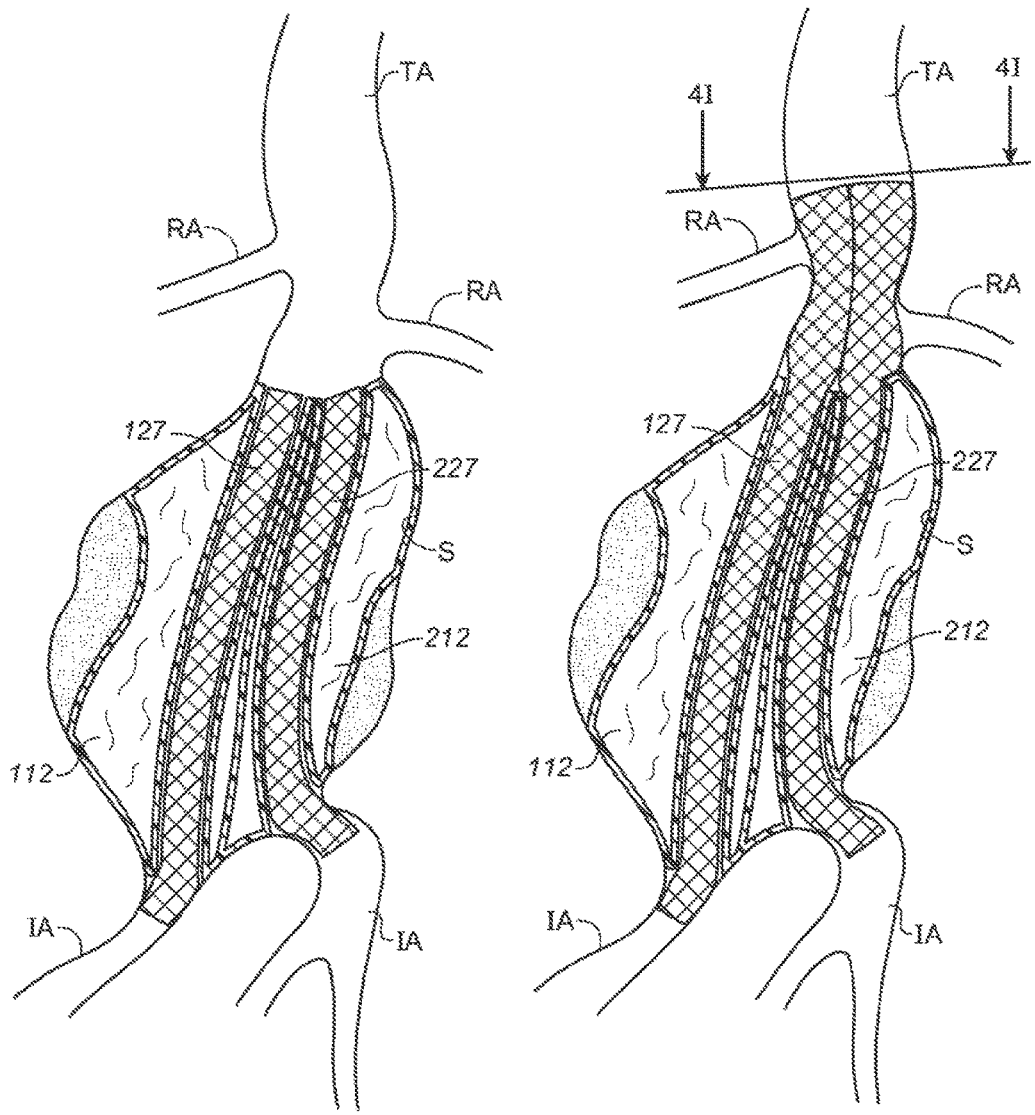
FIG. 10G  FIG. 10H
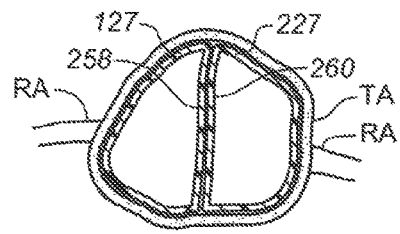
FIG. 10I

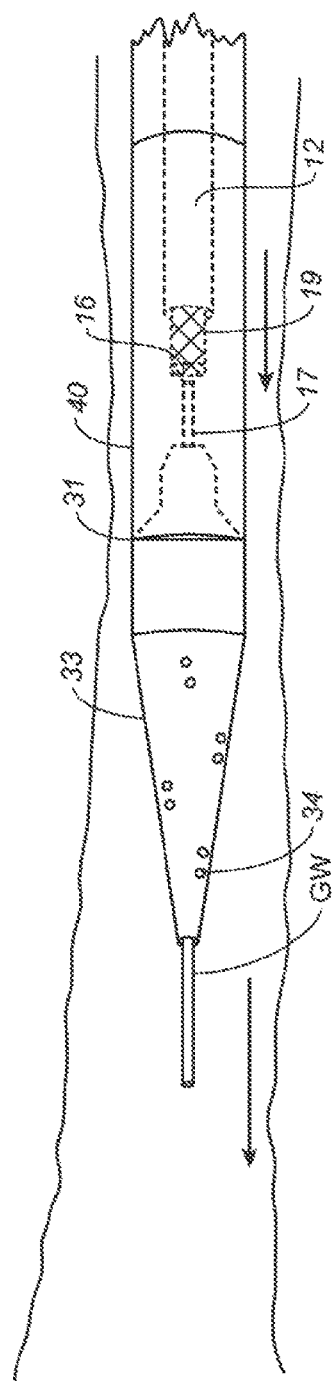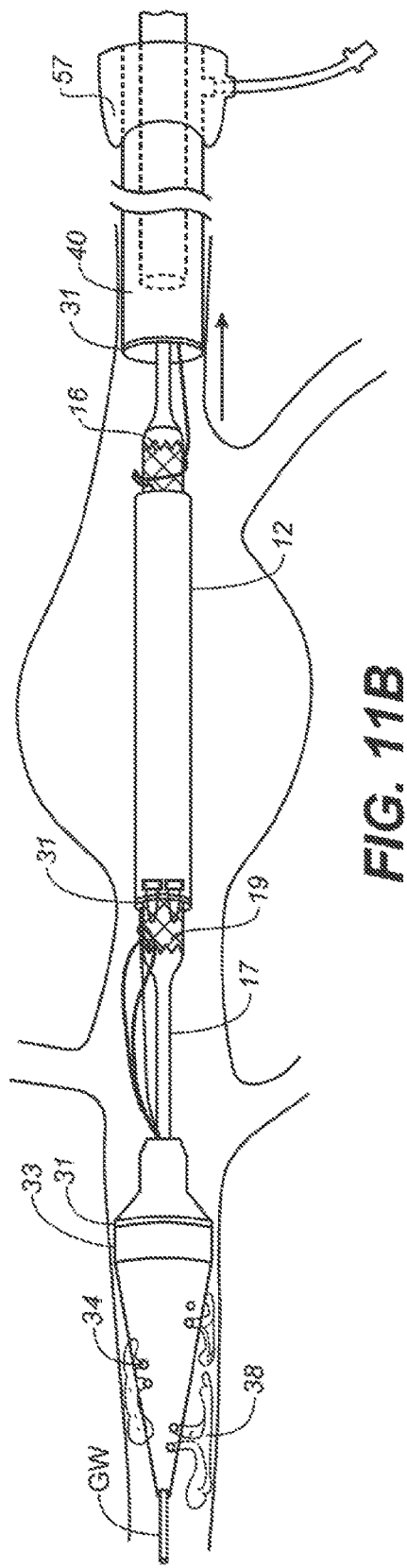

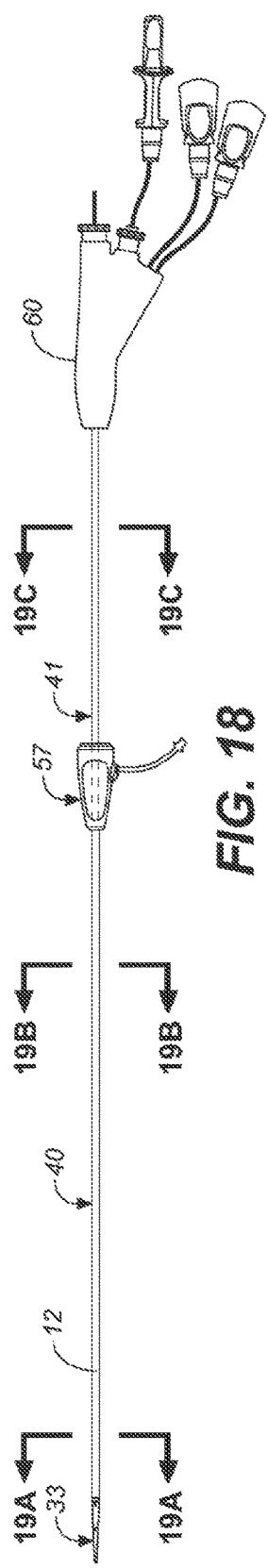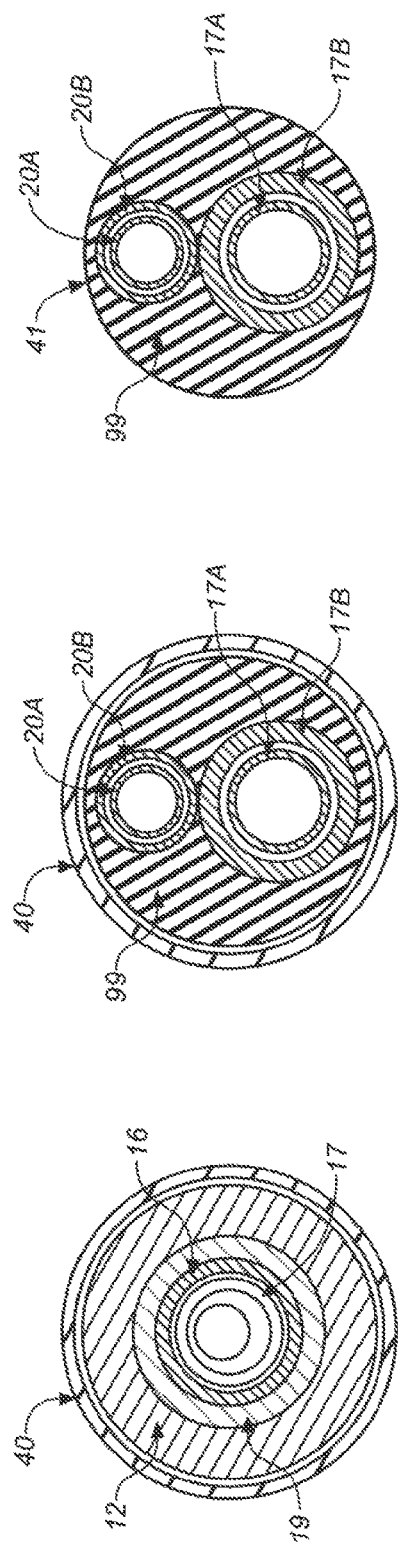
FIG. 18
FIG. 19A
FIG. 19B
FIG. 19C

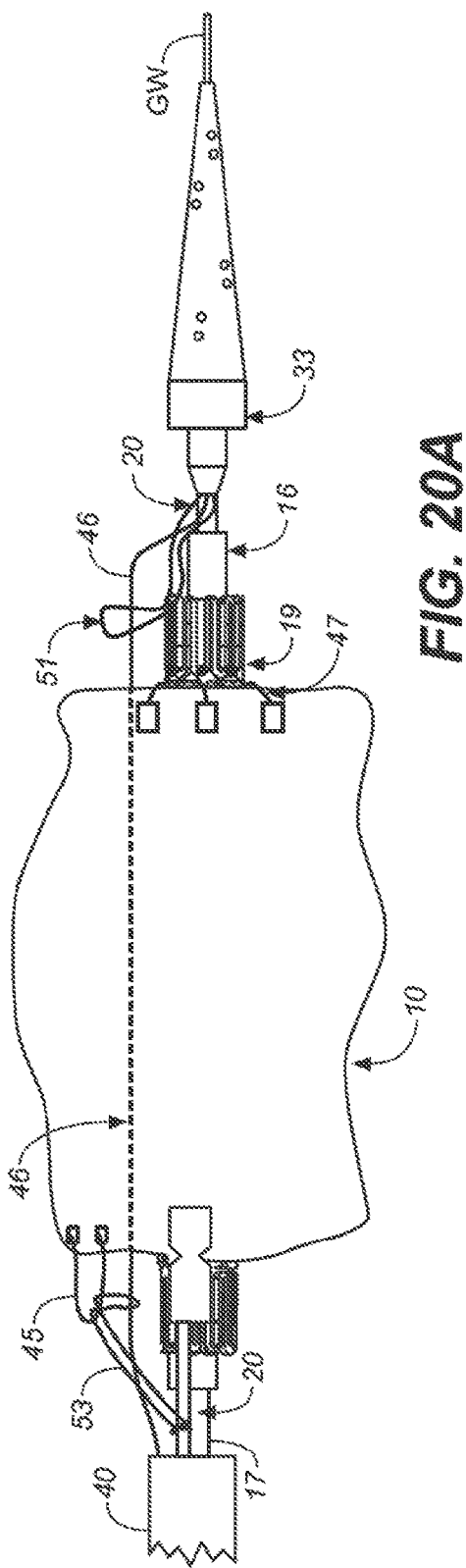
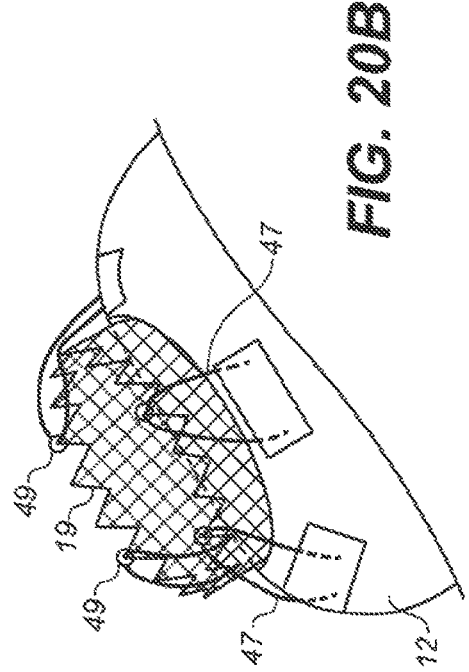
FIG. 20A
FIG. 20B

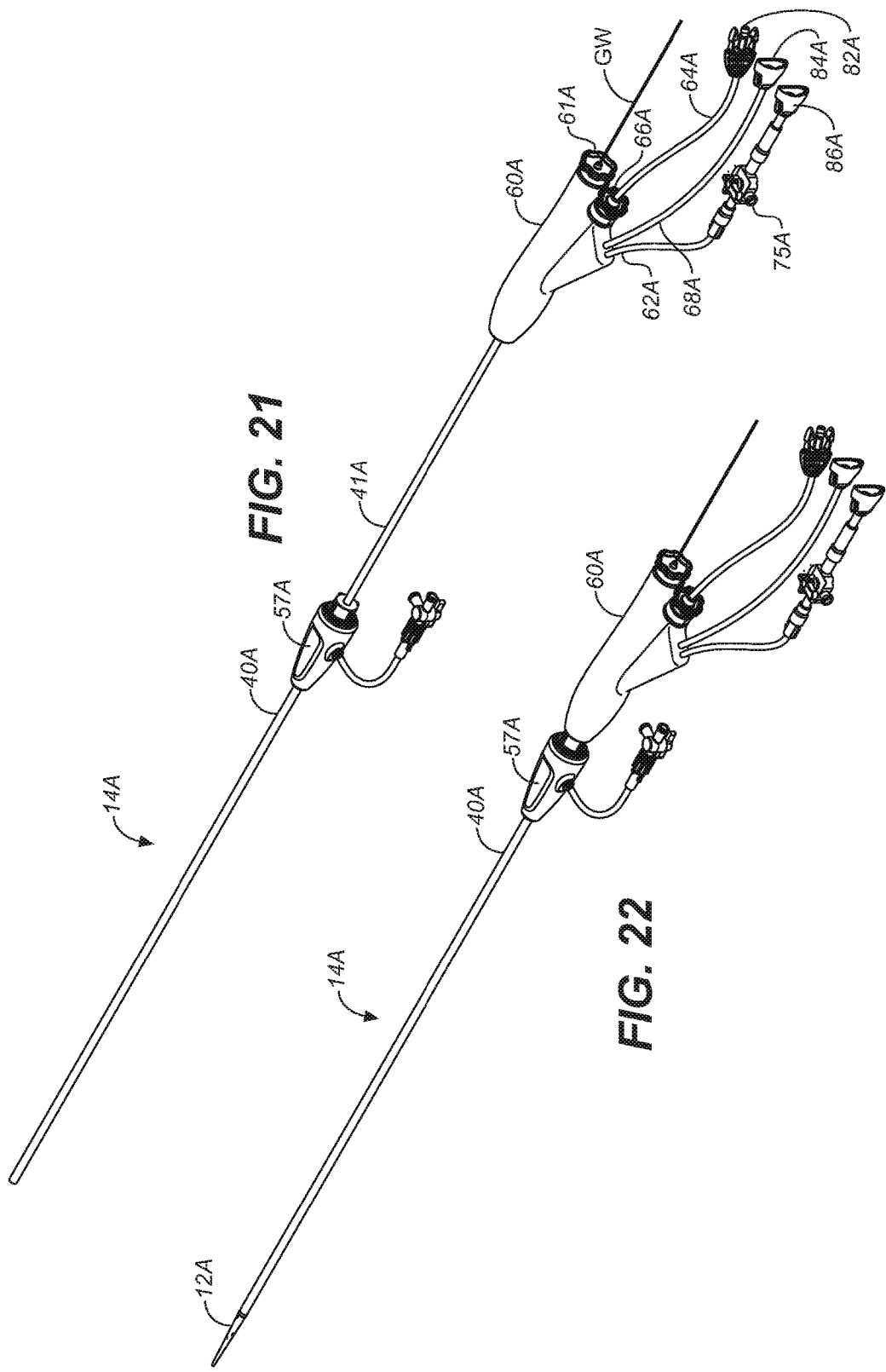

METHOD AND SYSTEM FOR TREATING ANEURYSMS

CROSS-REFERENCES TO RELATED APPLICATIONS

This application is a continuation application of, and claims benefit and priority to U.S. application Ser. No. 13/441,762, filed Apr. 6, 2012, entitled "METHOD AND SYSTEM FOR TREATING ANEURYSMS, now U.S. Pat. No. 9,415,195, issued Aug. 16, 2016, which claims the benefit and priority under 35 U.S.C. 119(e) of U.S. Provisional Application No. 61/472,209, filed Apr. 6, 2011 and U.S. Provisional Application No. 61/473,051, filed Apr. 7, 2011. The entire contents of each of the above-identified patent applications are incorporated herein by reference in their entirety.

BACKGROUND

Field of the Invention

Medical apparatus and methods for treatment related to expandable prosthesis and methods for treating abdominal and other aneurysms are disclosed.

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

There is concern about aneurysms occurring in the aorta, particularly those referred to as aortic aneurysms. Abdominal aortic aneurysms (AAA's) are classified based on their location within the aorta as well as their shape and complexity. Aneurysms which are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about seventy percent (70%) of all aortic aneurysms. Suprarenal aneurysms are less common, representing about 20% of the aortic aneurysms. Thoracic aortic aneurysms are the least common and often the most difficult to treat. Most endovascular systems are also too large (above 12 F) for percutaneous introduction.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Over the past decade, endoluminal grafts have come into widespread use for the treatment of aortic aneurysm in patients who cannot undergo open surgical procedures. In general, endoluminal repairs access the aneurysm "endoluminally" through either or both iliac arteries in the groin. The grafts, which typically have been fabric or membrane tubes supported and attached by various stent structures, are then implanted, typically requiring several pieces or modules to be assembled in situ. Successful endoluminal procedures have a much shorter recovery period than open surgical procedures.

Present endoluminal aortic aneurysm repairs, however, suffer from a number of limitations. A significant number of endoluminal repair patients experience leakage at the proximal juncture (attachment point closest to the heart) within two years of the initial repair procedure. While such leaks can often be fixed by further endoluminal procedures, the need to have such follow-up treatments significantly increases cost and is certainly undesirable for the patient. A less common but more serious problem has been graft migration. In instances where the graft migrates or slips from its intended position, open surgical repair is required. This is a particular problem since the patients receiving the endoluminal grafts are those who are not considered good candidates for open surgery. Further shortcomings of the present endoluminal graft systems relate to both deployment and configuration. Multiple component treatment systems require additional procedure time to allow for introduction of each piece and even more time for assembling the pieces in situ. Such techniques are not only more time consuming, they are also more technically challenging, increasing the risk of failure. Current devices are also unsuitable for treating many geometrically complex aneurysms, particularly infrarenal aneurysms with little space between the renal arteries and the upper end of the aneurysm, referred to as short-neck or no-neck aneurysms. Aneurysms having torturous geometries, are also difficult to treat.

For these reasons, it would desirable to provide improved methods, systems, and prosthesis for the endoluminal treatment of aortic aneurysms. Such improved methods, systems, and treatments should provide implanted prosthesis which result in minimal or no endoleaks, which resist migration, which are relatively easy to deploy, which have a low introduction profile (preferably below 12 F), and which can treat most or all aneurysmal configurations, including short-neck and no-neck aneurysms as well as those with highly irregular and asymmetric geometries.

Description of the Background Art

Grafts and endografts having fillable components are described in U.S. Pat. Nos. 4,641,653; 5,530,528; 5,665,117; 5,769,882; and 7,530,988; U.S. Patent Publication 2004/0116997; and PCT Publications WO 00/51522 and WO 01/66038.

BRIEF SUMMARY OF THE INVENTION

Methods, systems, and apparatuses for the endoluminal treatment of aneurysms, particularly abdominal aortic aneurysms (AAA's) and thoracic aortic aneurysms (TAA's) are provided herein. Generally, the prostheses comprise double-walled filling structures which have outside walls that are compliant or otherwise adapted to substantially fill the enlarged bulk volume of an aneurysm, particularly a fusiform aneurysm, leaving a lumen in place for blood flow.

The double-walled filling structures will thus usually have a generally toroidal structure with an outer wall, an inner wall, a potential space or volume between the outer and inner walls to be filled with a filling medium, and a generally tubular lumen inside of the inner wall which provides the blood flow lumen after the prosthesis has been deployed. The shape of the filling structure is adapted to conform to the aneurysm being treated during deployment. The filling structure size can be chosen from among a few sizes to match the needs and dimensions that might be needed by nearly all patients for treating their particular aneurysmal as determined by using imaging and computer-aided diagnostic techniques. A family or collection of available filling structures may include different geometries and sizes (lengths and lumen diameters) so that a treating physician may select a specific filling structure to treat a particular patient based on the size and geometry of that patient's aneurysm. By using the method and apparatuses described herein, each device can treat a large range of different sized anatomies, such that only a few different size devices need be kept in inventory to be prepared to treat the full range of approved aortic aneurysmal disease indications. Generally, the outer wall of the filling structure conforms or is conformable to the inner surface of the aneurysm being treated, while the inner wall of the structure is substantially aligned with lumens of the blood vessels upstream and downstream of the prosthesis after the prosthesis has been deployed.

The filling structures of the prosthesis will usually be formed from a compliant material, such as silicone, polyurethane, latex, or combinations thereof.

The walls of the filling structures may consist of a single layer or may comprise multiple layers which are laminated or otherwise formed together. Different layers may comprise different materials, including both compliant and/or non-compliant materials. The walls may also be structurally reinforced in various ways, including use of braided reinforcement layers, filament reinforcement layers, and the like. In some embodiments, the system may include self-expanding scaffolds within the filling structures so that the structures can be initially delivered and allowed to self-expand at the treatment site, thus obviating the need for the structures associated with a balloon delivery catheter as described below.

In many embodiments, delivery protocols described utilize delivery catheters having a balloon or other expandable support for carrying the filling structure. When using balloons, the balloons may be substantially or entirely compliant, although non-compliant and combination compliant/non-compliant balloons may also be used. The balloon or other mechanical expansion components of the delivery catheter will initially be disposed within the inner tubular lumen of the filling structure, with the filling structure generally being collapsed into a low width or low profile configuration over the expansion element. The delivery catheter may then be introduced intraluminally, typically into each iliac artery and upwardly to the region within the aorta to be treated. Such delivery catheters may also include one or more lumens, tubes, or other components or structures for delivering the filling medium in a fluid form to an internal filling cavity of the filling structure. Thus, the delivery catheters can be used to both initially place and locate the filling structure of the prosthesis at the aneurysmal site. Once at the aneurysmal site, the internal tubular lumens of the structures can be expanded simultaneously using the balloons or other expandable elements on the delivery catheters. The filling structures (separate from the expansion of the tubular lumen) will be filled and expanded by delivering the filling medium via the catheters into the internal volume of the filling structures. Generally, both expansion and filling operations are performed simultaneously for a reliable and consistently predictable treatment result, or can be individually expanded in either order, e.g. the filling structure may be filled first with the delivery catheter balloon being expanded second, or vice versa, as desired or if simultaneous expansion and filling can for some reason not be performed. The filling structure(s) and/or delivery balloons may have radiopaque markers to facilitate placement and/or pressure sensors for monitoring filling and inflation pressures during deployment. The simultaneous filling allows structures to automatically accommodate one another and does not require the operator take extra special care as is often necessary when pressurization of adjacent separate structures is done separately and not simultaneously from a common source.

As described below, the filling structure may be filled with filling medium at a pressure from 100 mm of Hg to 330 mm of Hg, as needed to achieve or slightly exceed the patient's systolic blood pressure to have the fill bag displace the blood already in the circulatory system; too high a pressure in a compliant balloon can create excess stress on the already weakened aneurysmal wall, thus should be avoided. The above pressures are gage pressures, i.e. measured relative to atmospheric pressure.

The sequential delivery of two prostheses and their respective filling structures may be utilized to initiate treatment of aneurysms located adjacent a vessel bifurcation, such as infrarenal abdominal aortic aneurysms. Two filling structures are introduced in a generally adjacent, parallel arrangement within and substantially spanning the aneurysmal volume and sac. In the specific case of infrarenal aneurysms, each prosthesis is typically delivered separately, one through each of the two iliac arteries. After locating the filling structures of the prosthesis within the aneurysmal space, to achieve an optimal result, they can be filled simultaneously using a pressurization manifold console, particularly a single operator pressurization manifold console, so as to fill and occupy substantially the entire aneurysmal volume, forming a pair of blood flow lumens spanning the aneurysmal sac.

Suitable filling materials typically include a fluid (often having a low viscosity), at least initially, to permit delivery through connected piping in the delivery catheter and may be curable or otherwise hardenable so that, once in place, the filling structure forms a final shape which will remain after the delivery catheter is removed. The fillable materials will usually be curable polymers which, after curing, will have a fixed shape with a Shore hardness typically in the range from 10 durometer to 140 durometer. The polymers may be delivered as liquids, gels, foams, slurries, or the like. The polymers may be epoxies or other curable two-part systems. In other embodiments, the polymer may comprise a single material which when exposed to the vascular environment within the filling structure changes state over time, typically from zero to ten minutes.

After curing, the filling material may have a specific gravity, typically in the range from 0.1 to 5, more typically from 0.8 to 1.2 which is generally the same as blood or thrombus. The filling material may also include bulking and other agents to modify density, viscosity, mechanical characteristics or the like, including microspheres, fibers, powders, gasses, radiopaque materials, drugs, and the like. Exemplary filling materials include polyurethanes, collagen, polyethylene glycols, microspheres, and the like.

Preferably, the filling structures of the prosthesis will require no additional sealing or anchoring means to hold them in place within the aneurysm. In some instances, however, it may be desirable to employ additional sealing or anchoring mechanisms, such as stents, scaffolds, hooks, barbs, sealing cuffs, and the like. For sealing cuffs or stents which extend proximally of infrarenal prosthesis, it may be desirable to provide openings or ports to allow the anchoring or sealing devices to extend over the renal ostia while penetrating blood flow into the renal arteries. The sealing or anchoring devices typically attach to and/or overlap with the filling structure of the prosthesis and provide for a smooth transition from the aortic and/or iliac lumens into the tubular lumens provided by the deployed filling structures.

The filling structures may be modified in a variety of ways. For example, the external surfaces of the filling structures may be partially or entirely modified to enhance placement within the aneurysmal space, typically by promoting tissue ingrowth or mechanically interlocking with the inner surface of the aneurysm. Such surface modifications include surface roughening, surface stippling, surface flocking, fibers disposed over the surface, foam layers disposed over the surface, rings, and the like. The filling structures may also include biologically active substances over all or a portion of the external surface of the filling structure, such as thrombogenic substances, tissue growth promotants, biological adhesives, and the like. The filling structures may further include synthetic adhesives, such as polyacrylamides, over the surface to enhance adherence.

In some applications, it may be desirable to modify all or a portion of the internal surface of the filling cavity of the filling structure. Such surface modifications may comprise surface roughening, rings, stipples, flocking, foam layers, fibers, adhesives, and the like. The purpose of such surface modification is usually be to enhance the filling and bonding to the filling material, and to control the minimum wall thickness when the structure is filled particularly after the filling material has been cured. In particular instances, such as in locations of the filling structure which are pressed together when the structure is deployed, thus potentially excluding filling material, it may be desirable if the surfaces of the filling structure adhere directly to each other.

In view of the above general description, specific embodiments are described and discussed herein. Methods for treating an aneurysm comprise positioning at least two double-walled filling structures across the aneurysm. By "across" the aneurysm, it is meant generally that the filling structure will extend axially from one anatomical location which has been identified by imaging or otherwise as being the beginning of the aneurysm to a second location (or locations in the case of bifurcated aneurysms) where it has been similarly established that the aneurysm ends. After positioning, the two filling structures are filled simultaneous by using a manifold console, particularly a single operator manifold console, to which the filling lines for the structures are securely coupled so that a fluid filling medium is supplied and causes an outer wall of the structure to expand and conform to the inside of the aneurysm and its complementary companion structure and an inner wall of the structures form generally tubular lumens to provide for blood flow after the filling structures have been deployed. The tubular lumens will preferably be supported, typically by a balloon or mechanically expansible element, while the filling structures are being filled, after the filling structures have been filled, or during both periods. After the filling structures have been filled, the filling material or medium is hardened while the tubular lumens remain supported. Supporting the tubular lumens during hardening assures that the lumens have a desired geometry, properly align with adjacent vascular lumens, and that the tubular lumens being formed remains aligned with the native aortic and/or iliac artery lumens after the prostheses have been fully implanted. The support may be provided by a balloon which extends proximally and distally of the filling structure where the balloon may slightly "overexpand" in order to assure the desired smooth transition and conformance of the tubular lumen provided by the filling structure with the native vessel lumens.

After hardening, the support (such as an endoframe) may be left in place, (if not obstructing blood flow) or may be removed, leaving the filling structure in place. In most instances, however, prior to hardening, it will be desirable to confirm proper placement of the filling structure. This can be done using imaging techniques or otherwise testing for patency and continuity. In some instances, it may be desirable to first fill the filling structure with saline or other non-hardenable substance to make sure that the geometry of the filling structure is appropriate for the patient being treated. After testing, the saline may be removed and replaced with the hardenable filler. Through the use of only a few sizes to cover most aneurysmal configurations, the use of a step of prefilling the filling structure with saline and the time expenditure associated with such a step can be avoided.

Treating abdominal aortic aneurysms may comprise use of a first double-walled filling structure and a second double-walled filling structure. The first and second filling structures are adapted to be simultaneously filled with a hardenable filling medium while they positioned adjacent to each other within the aneurysm. The systems further comprise first and second delivery catheters which can be used to align each of the first and second filling structures properly with the right and left iliacs and the infrarenal aorta as they are being deployed, filled, and hardened.

Thus a method for treating an aneurysm includes the steps of: positioning at least two double-walled filling structures having an aneurysm conforming outer wall and a blood transit lumen creating inner wall through two separate arteries across the one aneurysm to be treated; supporting the inner walls of the blood transit lumens with a support structure; causing the support structure to expand wherein each expanded support structure defines the shape of a corresponding expanded blood transit lumen; simultaneously filling the filling structures with a fluid filling medium so that their outer walls conform to the inside of the aneurysm and to each other thereby creating a blood transit barrier substantially filling the bulk volume of the aneurysm and substantially preventing blood transit between the aneurysm conforming outer wall and the inside of the aneurysm and the inner walls surround the expanded support structure to contain blood in each corresponding expanded blood transit lumen; hardening the filling medium; and removing fill lines connected to each of the double-walled filling structures after the fluid filling medium has hardened, wherein the fluid filling structure is filled with fluid filling medium at a filling pressure exceeding the systolic blood pressure experienced by the aneurysm and wherein the expanded support structure provides an outward force which is greater than the inward force applied by the filling pressure. The support structure may be an endoframe. The filling pressure may be in the range from 100 mm Hg to 330 mm Hg. The fluid filling medium can be a flowable polymer which is curable in situ. The polymer can be a polyurethane, a polyethylene glycol, or a collagen. The fluid filling medium can have a density in the range from 0.1 gm/cc to 5 gm/cc when hardened. The fluid filling medium comprises a two-part curable material which hardens after mixing. The method may include positioning an anchor or sealing element within at least one opening of the tubular lumen of the filling structure, wherein the anchor or sealing element extends from the lumen of the filling structure into a lumen of the blood vessel and/or positioning an anchor or sealing element at each opening.

Another method for treating an abdominal aortic aneurysm between the iliacs and the renal arteries, includes: positioning a first double-walled filling structure on a first endoframe from one iliac artery and artery access site, across the aneurysm, and into the aorta beneath the renal arteries, wherein the first endoframe shapes the entire length of a first tubular lumen; positioning a second double-walled filling structure on a second endoframe from the other iliac artery and artery access site, across the aneurysm, and into the aorta beneath the renal arteries and adjacent to the first double-walled filling structure, wherein the second endoframe shapes the entire length of a second tubular lumen; causing the first endoframe and the second endoframe to be expanded to create a first expanded tubular lumen and a second expanded tubular lumen; simultaneously filling the first filling structure and the second filling structure with a fluid filling medium so that an outer wall of the first filling structure and the second filling structure conform to an inside surface of the aneurysm and the first filling structure and second filling structure conform to each other and an inner wall of the first filling structure and the second filling structure each form a generally tubular lumen with a shape defined by the expanded first tubular lumen and the expanded second tubular lumen from the first iliac and the second iliac to the aorta beneath the renal arteries; simultaneously hardening the fluid filling medium in the first filling structure and the second filling structure while the first endoframe continues to define the shape of the expanded first tubular lumen and the second endoframe continues to define the shape of the expanded second tubular lumen. The first and the second endoframes may extend upstream and downstream from each double-walled filling structure of the first filling structure and the second filling structure so that each endoframe aligns and conforms each end of the filling structure with the iliac and aorta. An outer wall of the first filling structure or the second filling structure may be formed from a compliant material and/or from a non-compliant material or a combination thereof. Each endoframe can include a mechanical structure expandable to one or more fixed diameters. Each filling structure can be filled with fluid filling medium at filling pressure and each expanded endoframe resists the force of the filling pressure surrounding it and maintains the expanded shapes of the first and second tubular lumens. The filling pressure may be in the range from 100 mm Hg to 330 mm Hg. An anchor or sealing element may be positioned at one or more openings from the tubular lumen of at least one of the filling structures to a lumen of the iliac or aorta.

Another method of treating an aortic aneurysm using two catheters each having a sheath holding compressed within one or more expandable endobags in fluid communication with one another and an endobag fill line surrounding a compressed endoframe includes the steps of: threading a catheter into each of two separate femoral arteries of a patient to be treated and into the aorta with a common end of each endoframe of the catheters being positioned near a proximal end of an aneurysmal sac of the aneurysm to be treated, wherein the proximal ends of the endoframes of each of the catheters are positioned adjacent one another in anticipation of expansion of the endoframes of each of the adjacent catheters in a configuration ensuring substantially unobstructed blood flow through each lumen of the expanded endoframes; wherein the common end of the endoframes are at the substantially the same level and at a location in the aorta adjacent to where landing of the common ends of the endoframes is intended; removing the sheath exposing the expandable endobag and expanding the compressed endoframe of each of the two catheters; establishing communication between a fill line for an expandable endobag of a first of the two catheters and a fill line for an expandable endobag of a second of the two catheters and a curable filler material source to form an endobag filler circuit; monitoring and controlling the pressure within the endobag filler circuit while using one source of curable filler material to pressurize the endobag filler circuit thereby simultaneously pressurizing the fill line for each expandable endobag of the two catheters causing the expandable endobags disposed across the aneurysm within the patient to inflate to fill the aneurysm and press against each other and the aneurysmal wall, wherein controlling the pressure within the endobag filler circuit consists of filling of the endobag filler circuit until the maximum pressure reading monitored during pressurization is at least equal to the systolic blood pressure of the patient being treated, wherein the maximum pressure reading monitored during pressurization is established when curable filler material injection causing the pressurizing of the endobag filler circuit is stopped and steady state endobag circuit pressure is measured; maintaining the pressure within the endobag filler circuit for a curing time allowing the curable filler material to cure; detaching the endobag fill lines from their respective endobags and removing the two catheters from the patient.

A system for treating an aneurysm includes: a first catheter and a second catheter each catheter having a double-walled filling structure with an aneurysm conforming outer wall and a blood transit lumen creating inner wall, known as an endobag, surrounding an endoframe releasably coupled to the catheter and held compressed in an unexpanded configuration by a retractable sheath, wherein an endobag pressurization piping has one end releasably coupled to the endobag and has an inner lumen in communication with the inside of the endobag with the other end of the endobag pressurization piping extending within the sheath and in communication with endobag pressurization tubing outside the catheter, wherein an inside of an endoframe expanding substantially non-compliant balloon is in communication with endoframe pressurization tubing outside of the catheter, and wherein a guidewire lumen of the catheter is in communication with guidewire lumen pressurization tubing extending outside of the catheter; a single operator sequential manifold console having two endobag pressurization tubing outlet ports, two endoframe pressurization tubing outlet ports, and two guidewire lumen pressurization outlet ports wherein one of the two ports are connectable to the ends of the corresponding pressurization tubing outside of both the first catheter and the second catheter; the manifold console further having sequential inlet ports, wherein a first inlet port communicates with the two endobag pressurization tubing outlet ports, wherein a second inlet port communicates with the two endoframe pressurization tubing outlet ports, and wherein a third inlet port communicates with the two guidewire lumen pressurization outlet ports, wherein when the tubing ends from the first and the second catheters are connected to the corresponding manifold console outlet ports, pressurization of the corresponding inlet port equally pressurizes the corresponding pressure containing passage in both the first catheter and the second catheter simultaneously; wherein the first, second, and third inlet ports are configured in a side by side sequential configuration, where the sequential configuration of first, second, and third ports is arranged to match a recommended sequence of an operator's steps of pressure application to the first and second catheter endobag pressurization, endoframe pressurization, and guidewire lumen pressurization tubing. The single operator sequential manifold console may include a polymer cured indicator comprising a colored surface facing a light transmissive section of the endobag pressurization piping along the polymer flow path of the piping between the endobag pressurization inlet port and the two endobag pressurization outlet ports, such that the color of the colored surface can be seen through the light transmissive section of the piping when the piping is empty or is pressurized to contain uncured polymer and that the color of the colored surface is at least partially obstructed by a change in light transmissivity of the polymer as it cures thereby providing a visual confirmation, by the obstruction of viewing of the colored surface to the operator of the state of cure of the polymer. The single operator sequential manifold console may also include a fourth inlet port, which is also in communication with the endobag pressurization piping in the manifold console, where the fourth port is not located adjacent the first inlet port. The single operator sequential manifold console may include a fourth inlet port flow valve which when closed prevents flow between the endobag pressurization piping in the sequential manifold console and the fourth inlet port. The single operator sequential manifold console includes a third inlet port flow valve which when closed prevents flow between the guidewire lumen pressurization piping in the sequential manifold console and the third inlet port.

A single operator sequential manifold console may include two endobag pressurization tubing outlet ports, two endoframe pressurization tubing outlet ports, and two guidewire lumen pressurization outlet ports wherein one of the two ports are connectable to ends of corresponding pressurization tubing outside of both a first catheter and a second catheter; the manifold console further having sequential inlet ports, wherein a first inlet port communicates with the two endobag pressurization tubing outlet ports, wherein a second inlet port communicates with the two endoframe pressurization tubing outlet ports, and wherein a third inlet port communicates with the two guidewire lumen pressurization outlet ports, wherein when the tubing ends from the first and the second catheters are connected to the corresponding manifold console outlet ports, pressurization of the corresponding inlet port equally pressurizes the corresponding pressure containing passage leading to both the first catheter and the second catheter simultaneously; wherein the first, second, and third inlet ports are configured in a side by side sequential configuration, where the sequential configuration of first, second, and third ports is arranged to match a recommended sequence of an operator's steps of pressure application to the connectable first and second catheter endobag pressurization, endoframe pressurization, and guidewire lumen pressurization tubing. The single operator sequential manifold console may include a polymer cured indicator comprising a colored surface facing a light transmissive section of the endobag pressurization piping along the polymer flow path of the piping between the endobag pressurization inlet port and the two endobag pressurization outlet ports, such that the color of the colored surface can be seen through the light transmissive section of the piping when the piping is empty or is pressurized to contain uncured polymer and that the color of the colored surface is at least partially obstructed by a change in light transmissivity of the polymer as it cures thereby providing a visual confirmation, by the obstruction of viewing of the colored surface to the operator of the state of cure of the polymer. The single operator sequential manifold console may also include a fourth inlet port, which is also in communication with the endobag pressurization piping in the manifold console, where the fourth port is not located adjacent the first inlet port and which when closed prevents flow between the endobag pressurization piping in the sequential manifold console and the fourth inlet port. The single operator sequential manifold may include a third inlet port flow valve which when closed prevents flow between the guidewire lumen pressurization piping in the sequential manifold console and the third inlet port.

BRIEF DESCRIPTION OF THE DRAWINGS

FIGS. 10A-10I illustrate exemplary usage of the system of FIG. 9 for treating an infrarenal abdominal aortic aneurysm.

FIGS. 11A-11B illustrates an exemplary system having a fenestrated nosecone during advancement of the system in the vasculature and during deployment of the filling structure at the treatment site, respectively.

FIGS. 18 and 19A-19C illustrate an exemplary embodiment and cross-sections of the embodiment.

FIGS. 20A-20E illustrates exemplary coupling mechanisms of an aneurysm treatment system, in accordance with several embodiments.

FIGS. 21 and 22 show two lateral views of a catheter treatment system, the catheter of FIG. 21 is shown in its as shipped configuration, i.e., prior to initiating deployment, where the sheath retraction knob, end handle, fluid connection, and endobag release wire fittings are in their pre-deployment configuration. FIG. 22 shows a configuration of the catheter with the sheath having been retracted, i.e., after deployment has been initiated.

FIG. 23 is a lateral view showing two single catheter treatment systems configure for operation with a single operator manifold console.

DETAILED DESCRIPTION

Figure 1:
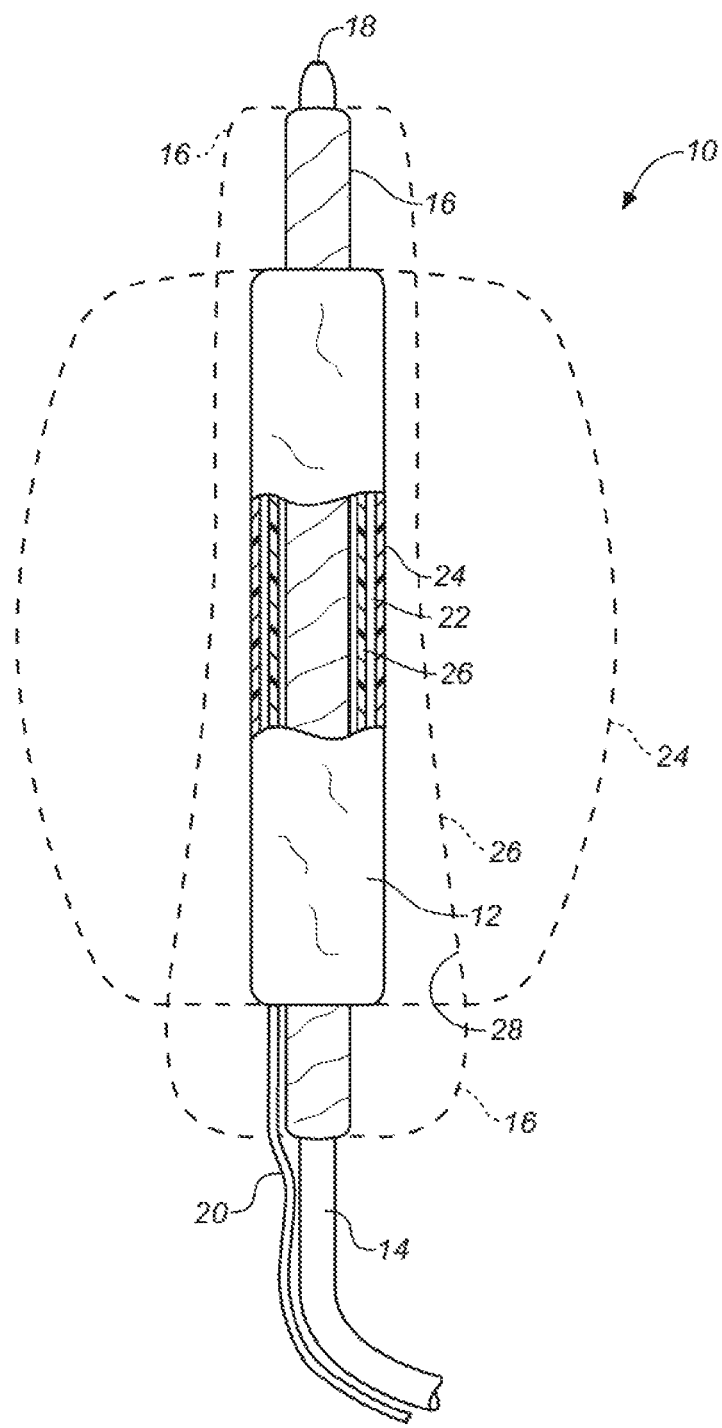
FIG. 1 illustrates an example of a single prosthesis system comprising a filling structure mounted over a delivery catheter.

A system 10 is for delivering a double-walled filling structure 12 to an aneurysm includes the filling structure and a delivery catheter 14 having an expandable element, typically an inflatable balloon 16, at its distal end. The catheter 14 will comprise a guidewire lumen 18, a balloon inflation lumen (not illustrated) or other structure for expanding other expandable components, and a filling tube 20 for delivering a filling medium or material to an internal space 22 of the double-walled filling structure 12. The internal space 22 is defined between an outer wall 24 and inner wall 26 of the filling structure. Upon inflation with the filling material or medium, the outer wall will expand radially outwardly, as shown in broken line, as will the inner wall 26, also shown in broken line. Expansion of the inner wall 26 defines an internal lumen 28. The expandable balloon 16 or other structure will be expandable to support an inner surface of the lumen 28, as also in broken line in FIG. 1.

Figure 2:
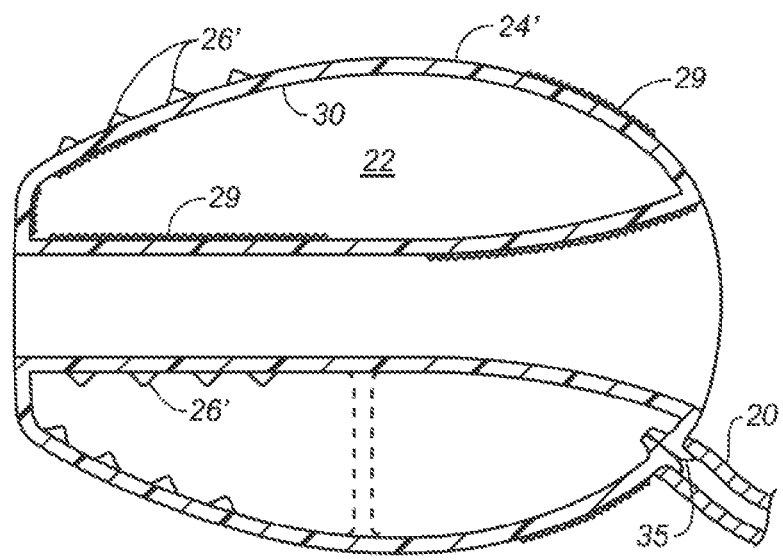
FIG. 2 is a cross-sectional view of the filling structure of FIG. 1 illustrating various surface modifications and a filling valve.

Referring now to FIG. 2, and the various internal and external surfaces may be shaped, coated, treated, or otherwise modified, to provide for a number of potentially desirable features of the present apparatus. For example, the external surface 24' of the outer wall may be shaped to have rings, stipples, or other surface features 26' which are typically formed into the material of the structure at the time of molding, vapor deposition, or other manufacturing process. The outer surface may also be coated with materials 29 which can be adhesives, drugs, active substances, fibers, flocking, foams, or a variety of other materials. In most cases, such surface features or modifications will be intended to enhance sealing or attachment of the outer wall 24 to the inner surface of the aneurysm being treated.

The inner surface 30 of the filling volume 22 may also be modified by providing features 26', coatings, surface roughening, coated with materials 29, or a variety of other modifications. The purpose of such internal features is typically to enhance adherence of the walls to the filling material or medium as the medium is cured or otherwise hardened. In some instances, materials may be coated on all or a portion of the inside surface 30 to induce or catalyze hardening of the filling material as it is being introduced.

The double-walled filling structure 12 will typically comprise at least one valve 35 to permit the introduction of the filling material or medium into the internal volume 22 using filling tube 20. As illustrated, the valve 35 may be a simple flap valve. Other more complex ball valves, and other one-way valve structures may be provided. In other instances, two-way valve structures may be provided to permit both filling and selective emptying of the internal volume 22. In other instances, the filling tube may comprise a needle or other filling structure to pass through the valve 35 to permit both filling and removal of filling medium.

Figure 3A:
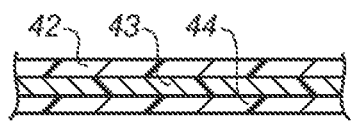
FIGS. 3A-3C illustrate alternative wall structures for the filling structure.
Figure 3B:
Figure 3C:

As illustrated in FIG. 2, the wall structure of the double-walled filling structure may be a single layer, typically molded or otherwise conventionally formed. The wall structures may also be more complex, as illustrated for example, FIGS. 3A-3C. FIG. 3A shows a multi-layered wall comprising layers 42, 43 and 44. It will be appreciated that such multiple layer structure can provide for increased strength, puncture resistance, variations in compliance and/or flexibility, differences in resistance to degradation, and the like. As shown in FIG. 3B, a single wall or multiple wall structure can be reinforced by braid, coils, or other metal or non-polymeric reinforcement layers or structures 48. As shown in FIG. 3C, the external surface 24' of the wall may be covered with drugs, fibers, protrusions, holes, active agents or other substances for a variety of purposes.

Figure 4:
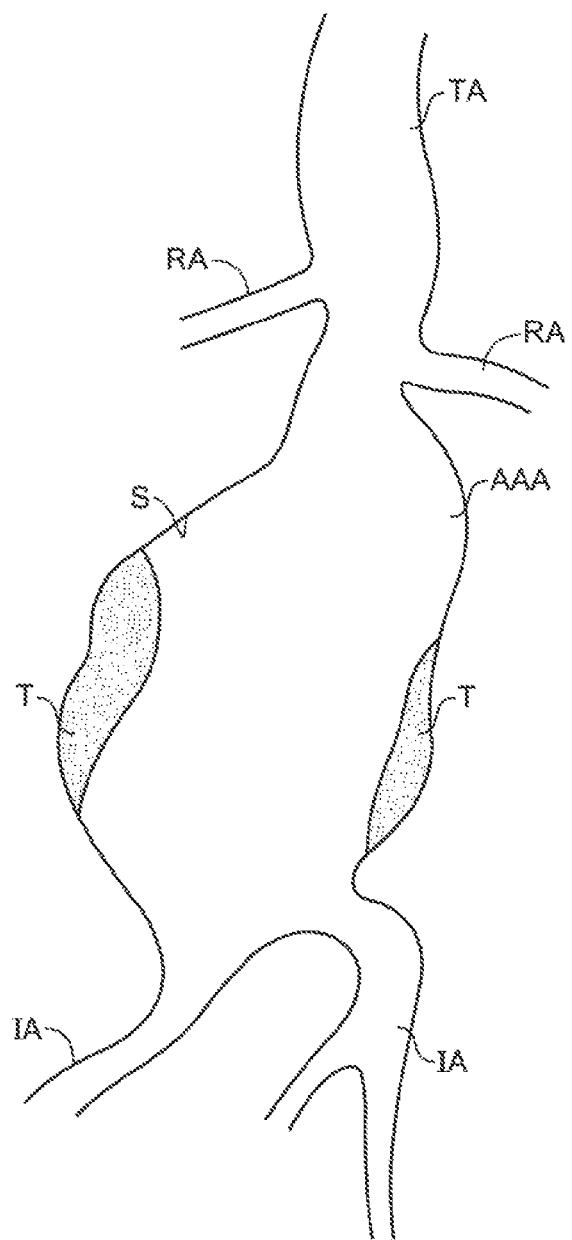
FIG. 4 illustrates the anatomy of an infrarenal abdominal aortic aneurysm.

Referring now to FIG. 4, the anatomy of an infrarenal abdominal aortic aneurysm comprises the thoracic aorta (TA) having renal arteries (RA) at its distal end above the iliac arteries (IA). The abdominal aortic aneurysm (AAA) typically forms between the renal arteries (RA) and the iliac arteries (IA) and may have regions of mural thrombus (T) over portions of its inner surface (S).

Figure 5A:
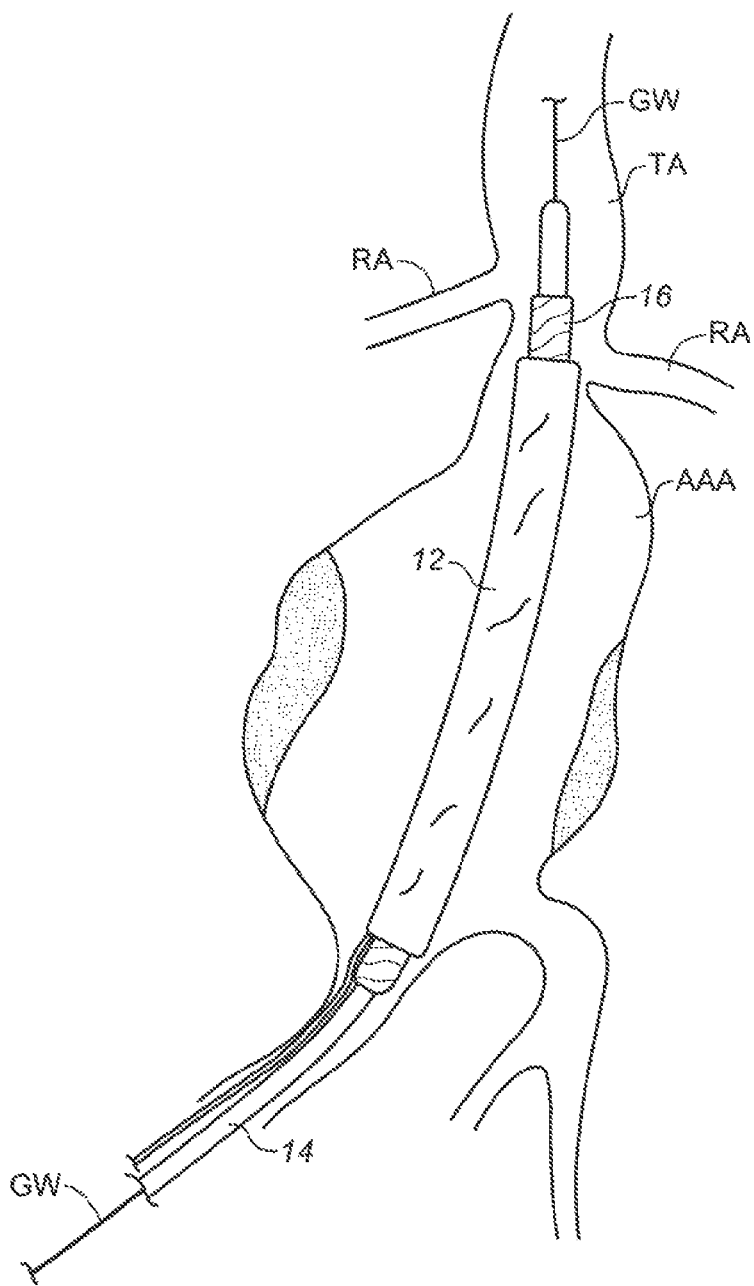
FIGS. 5A-5D illustrate use of the prosthesis system of FIG. 1 for treating the infrarenal abdominal aortic aneurysm.

Referring to FIGS. 5A-5D, the system 10 of FIG. 1 may be utilized to treat the complex geometry of the transmural abdominal aortic aneurysm (AAA) of FIG. 4 by first positioning the delivery catheter 14 to place the double-walled filling structure 12 (in its unfilled configuration) generally across the aneurysm from the region of the aorta beneath the renal arteries (RA) to a region over the iliac arteries (IA), as best seen FIG. 5A. Usually, the delivery catheter 14 will be introduced over a guidewire (GW) through a puncture in the patient's groin accessing the iliac artery by the Seldinger technique.

After the double-walled filling structure 12 is properly positioned, a hardenable inflation medium is introduced into the internal space 22 filling of the inner space 22 and expands the outer wall 24 of the structure outwardly so that it conforms to the inner surface (S) of the aneurysmal space.

Figure 5B:
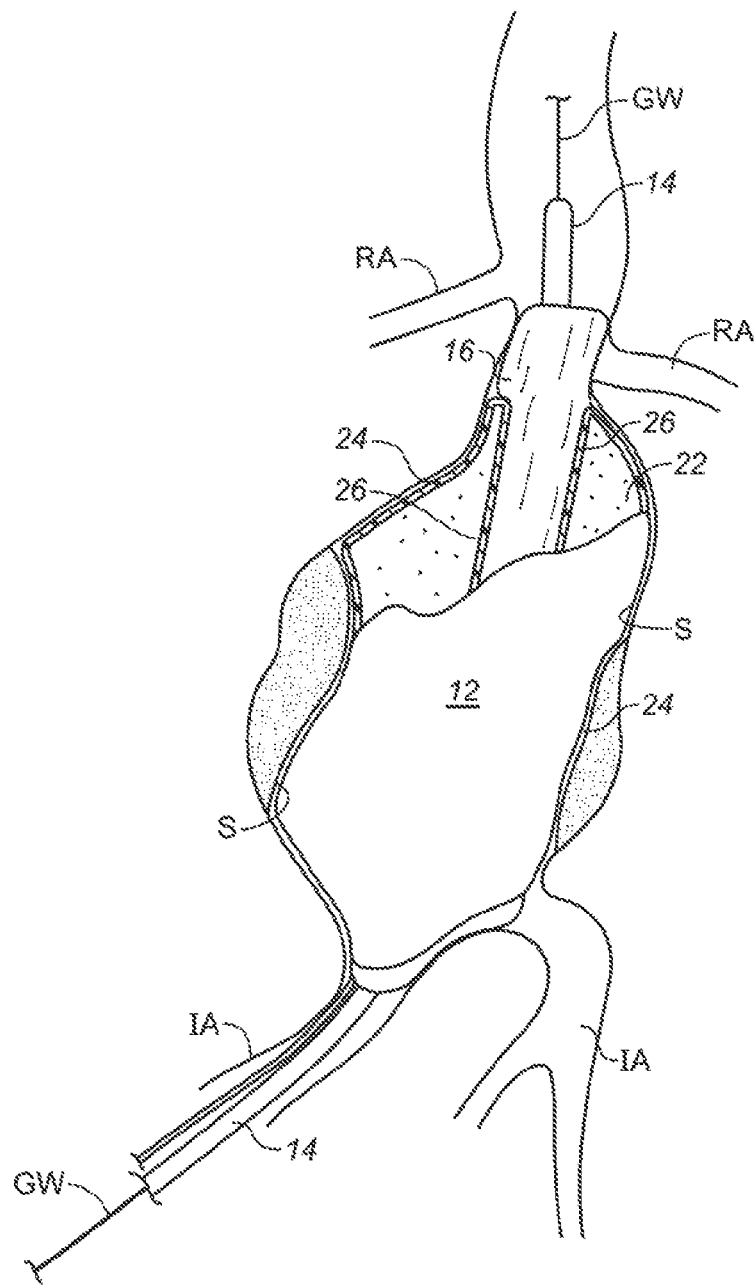
Figure 5C:
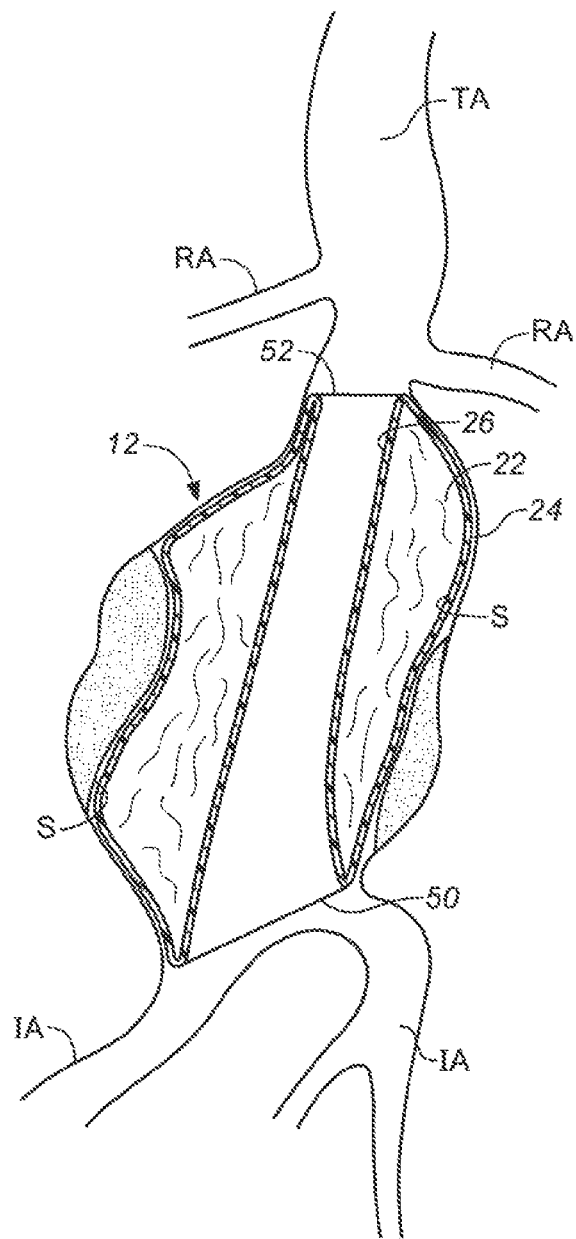

Before, during, or after filling of the double-walled filling structure 12 with inflation medium, as illustrated in FIG. 5B, the balloon 16 or other expansible structure will also be inflated or expanded to open the tubular lumen defined by the interior of the inner wall 26. Commonly, a non-compliant balloon 16 will be used, typically having a maximum diameter of width which is at or slightly larger than the desired tubular lumen diameter or width through the deployed double wall filling structure 12. The filling structure 12, in contrast, may be partially or completely formed from a generally compliant material, thus allowing the non-compliant balloon 16 or other expansible structure to fully open the tubular lumen and conform the ends of the lumens to the aorta and iliac walls, as illustrated in FIG. 5C. A lower or distal end 50 of the tubular lumen may be flared to a larger diameter so that it can accommodate the openings into both of the iliac arteries (IA) as illustrated. The filling structure 12 geometry can be chosen to most closely match the particular patient geometry being treated as determined during pre-treatment planning. A balloon 16 or other expansible structure which will be shaped to preferentially open the lower distal end 50 of the tubular lumen to a larger diameter than the upper or proximal end 52 can be used.

After the filling material has been introduced to the filling structure 12, typically through the filling tube 20, the fluid filling material must be cured or otherwise hardened to provide for the permanent implant having a generally fixed structure which will remain in place in the particular aneurysmal geometry. Methods for curing or hardening the filling material will depend on the nature of the filling material. For example, certain polymers may be cured by the application of energy, such as heat energy or ultraviolet light. Other polymers may be cured when exposed to body temperature, oxygen, or other conditions which cause polymerization of the fluid filling material. Still others may be mixed immediately prior to use and simply cure after a fixed time, typically minutes. Often, after the filling material has been hardened, the delivery catheter 14 may be removed and the filling structure left in place as the completed prosthetic implant.

Figure 5D:
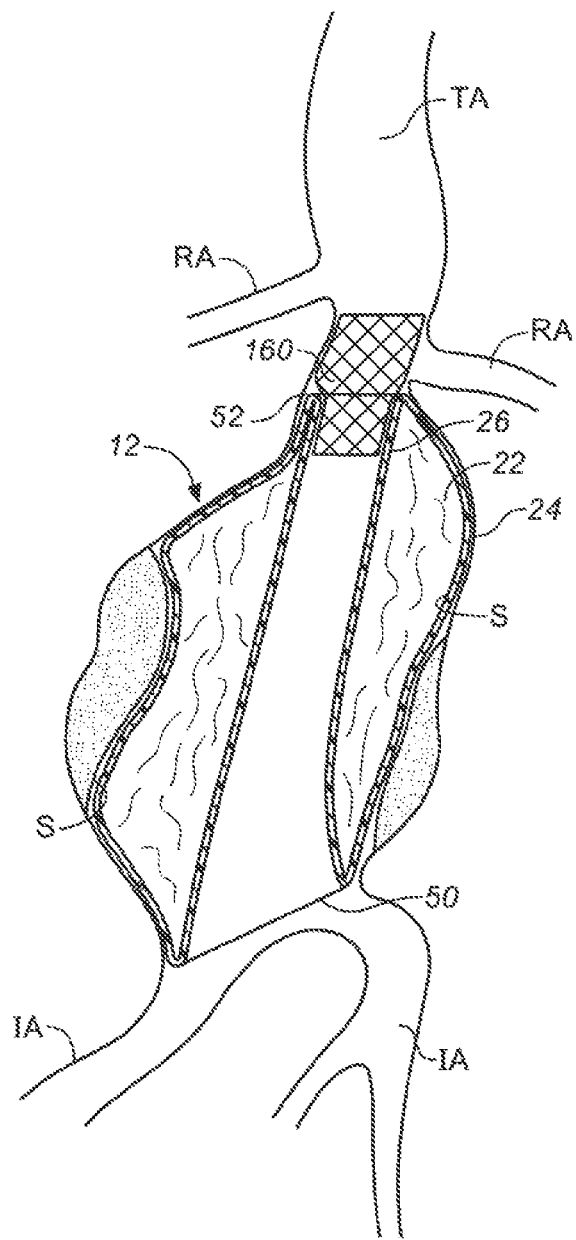

In other cases, however, it may be desirable to further position certain seals, anchors, stents, or other additional prosthetic components at either the proximal end 52 or distal end 50 of the graft. As illustrated in FIG. 5D, for example, a stent-like structure 160 may be planted in the upper proximal end opening of the tubular lumen of the filling structure 12 in order to help anchor the structure, help prevent intrusion of blood into the region between the outer wall 24 and inner surface (S) of the aneurysm, and to generally improve the transition from the aorta into the tubular lumen. The sealing or anchoring structure may simply comprise a stent-like component, preferably having a port or other access route to allow blood flow into the covered renal arteries (if any). Alternatively, the anchor structure could be another inflatable unit, such as the anchor described in co-pending, commonly owned application US Patent Application US2004/0116997A1, the full disclosure of which is incorporated herein by reference.

Figure 6:
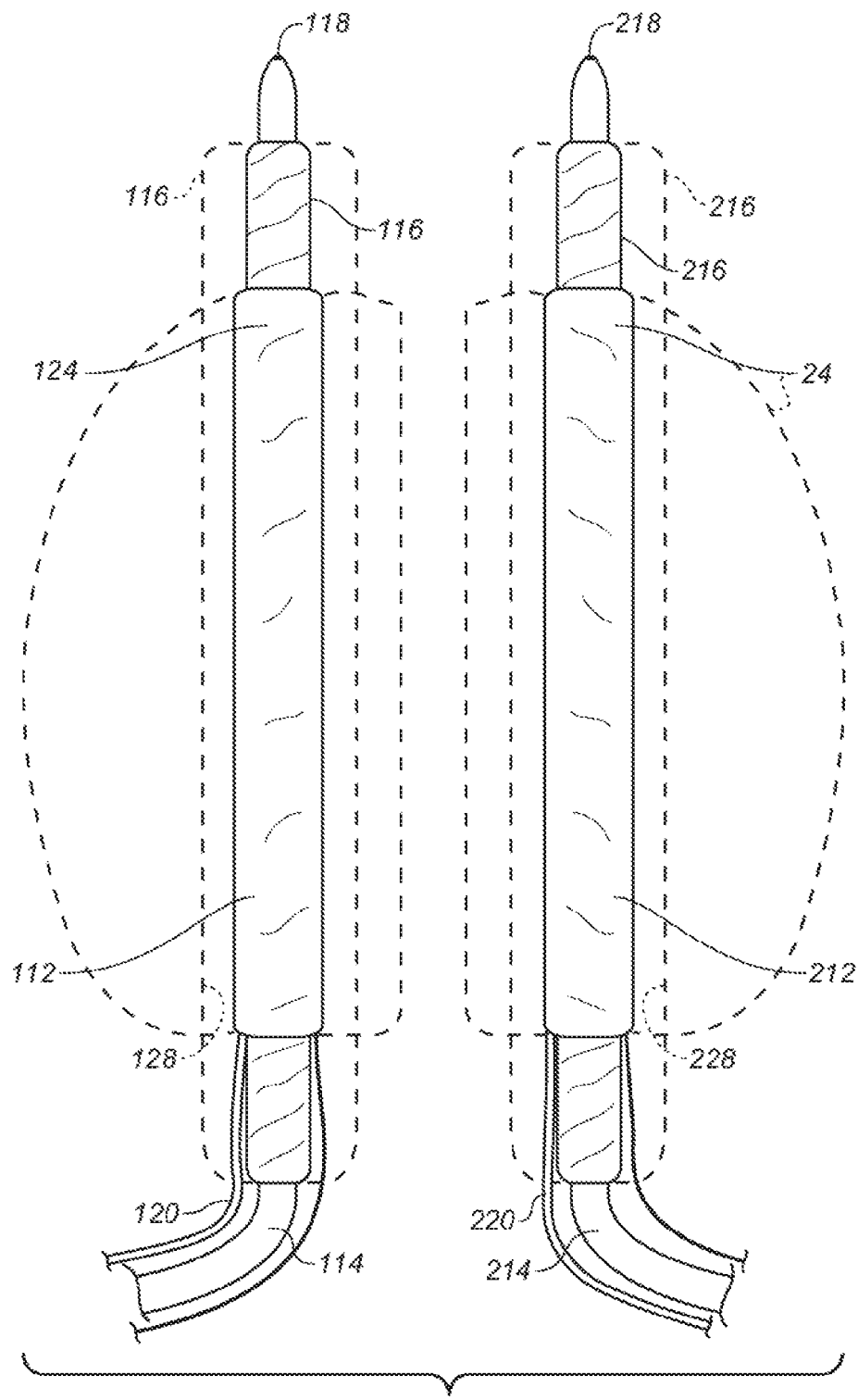
FIG. 6 illustrates an example of a system with a pair of prosthesis for delivery to an infrarenal abdominal aortic aneurysm, where each prosthesis comprises a filling structure mounted on a delivery catheter.

In a particular, a pair of double-walled filling structures will simultaneously be used to treat infrarenal abdominal aortic aneurysms, instead of only a single filling structure as illustrated in FIGS. 5A-5C. A system comprising such a pair of filling structures is illustrated in FIG. 6 which includes a first filling structure 112 and a second filling structure 212. Each of the filling structures 112 and 212 are mounted on delivery catheters 114 and 214, respectively. The components of the filling structures 112 and 212 and delivery catheters 114 and 214 are generally the same as those described previously with respect to the single filling structure system 10 of FIG. 1. Corresponding parts of each of the fillings structures 112 and 212 will be given identical numbers with either the 100 series base number or 200 series base number. The difference between the filling structures 112 and 212, on the one hand, and the filling structure 12 of FIG. 1 is that the pair of filling structures may generally have slightly smaller filling volume configurations as they only need to occupy an approximately complimentary half the volume of the aneurysm which are meant to be positioned adjacent to each other within the aneurysmal space and to in combination fill that space, as will be described with specific reference to FIG. 7A-7F below.

Figure 7A:
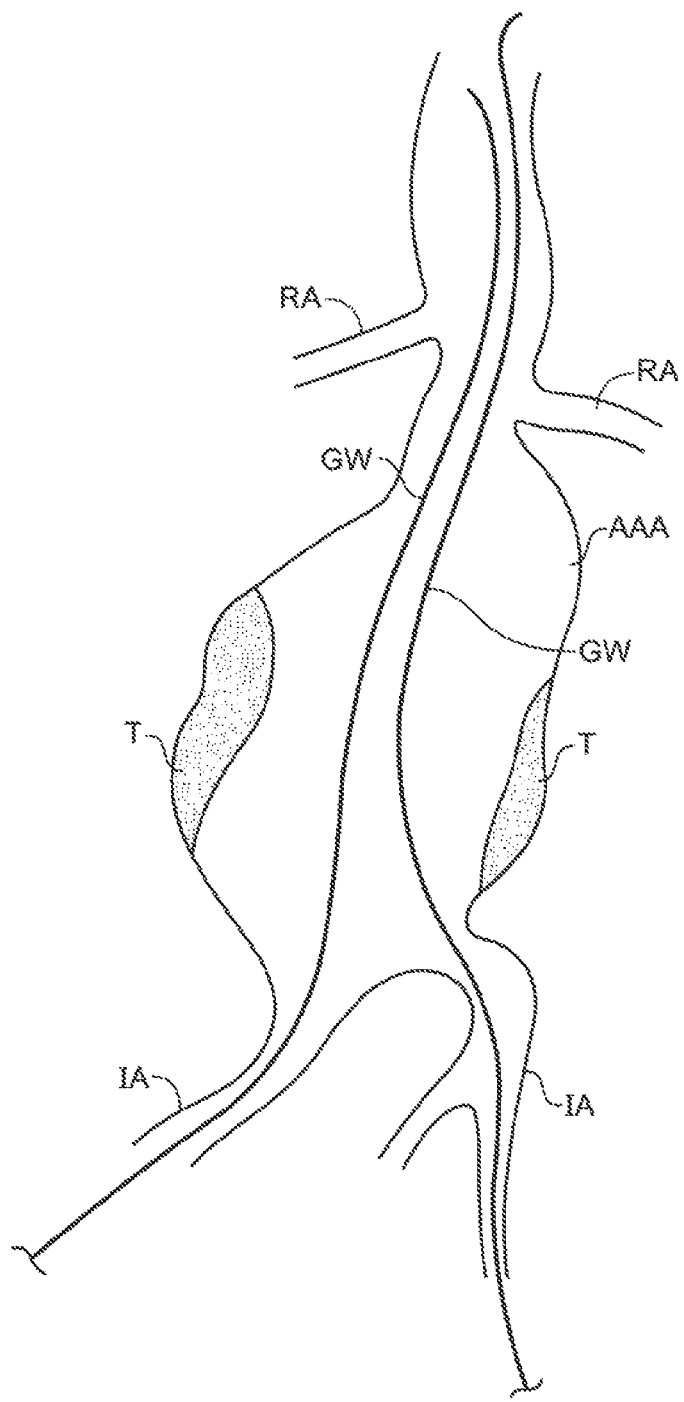
FIGS. 7A-7F illustrate use of the prosthesis system of FIG. 6 for treating an infrarenal abdominal aortic aneurysm.
Figure 7B:
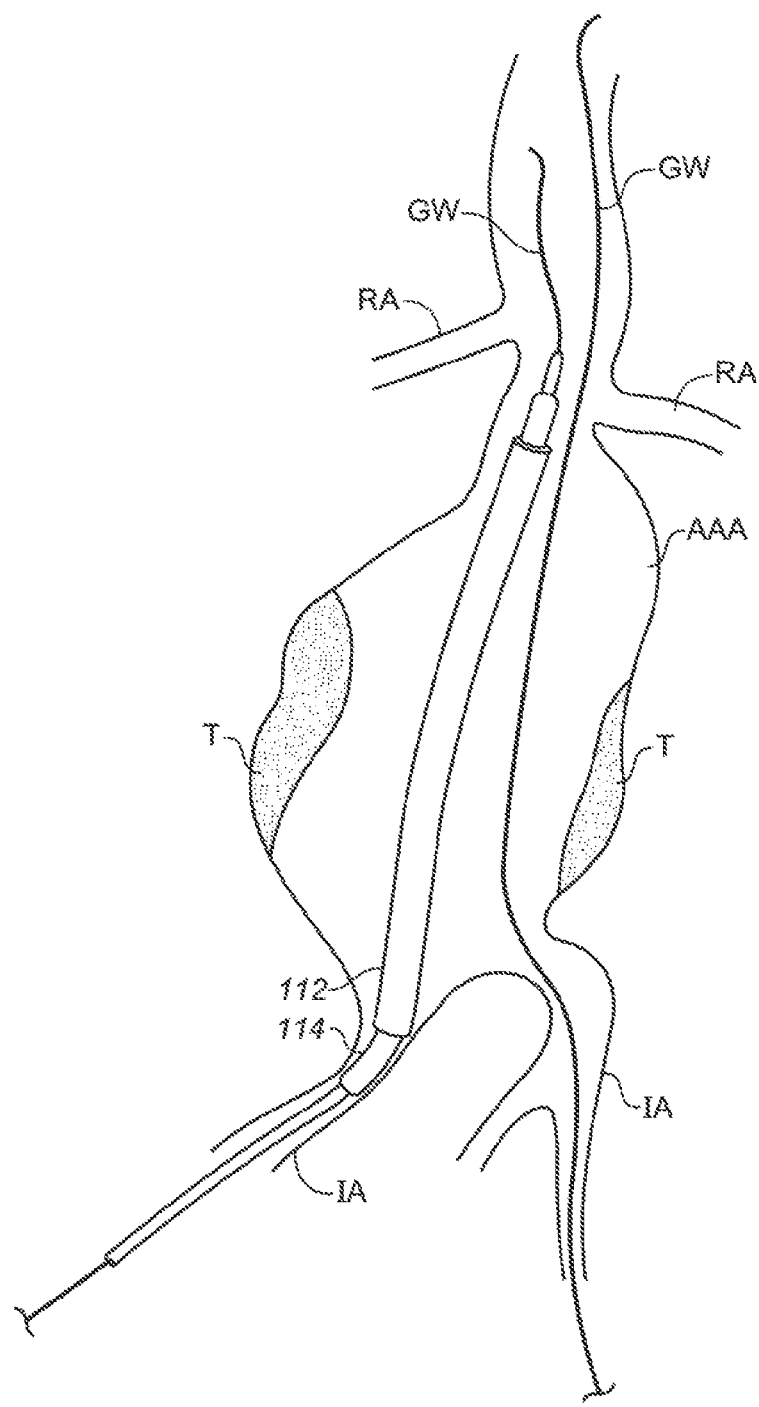
Figure 7C:
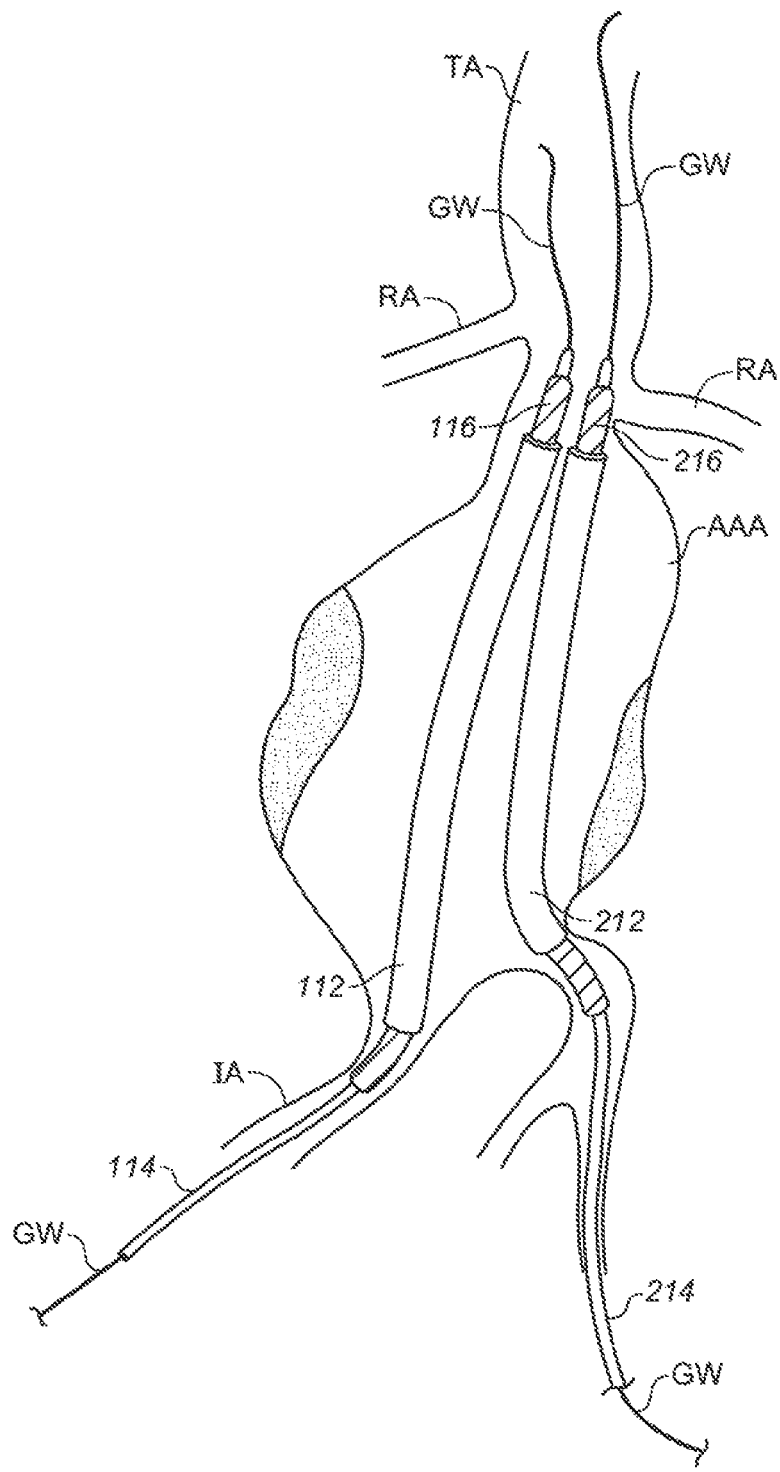
Figure 7D:
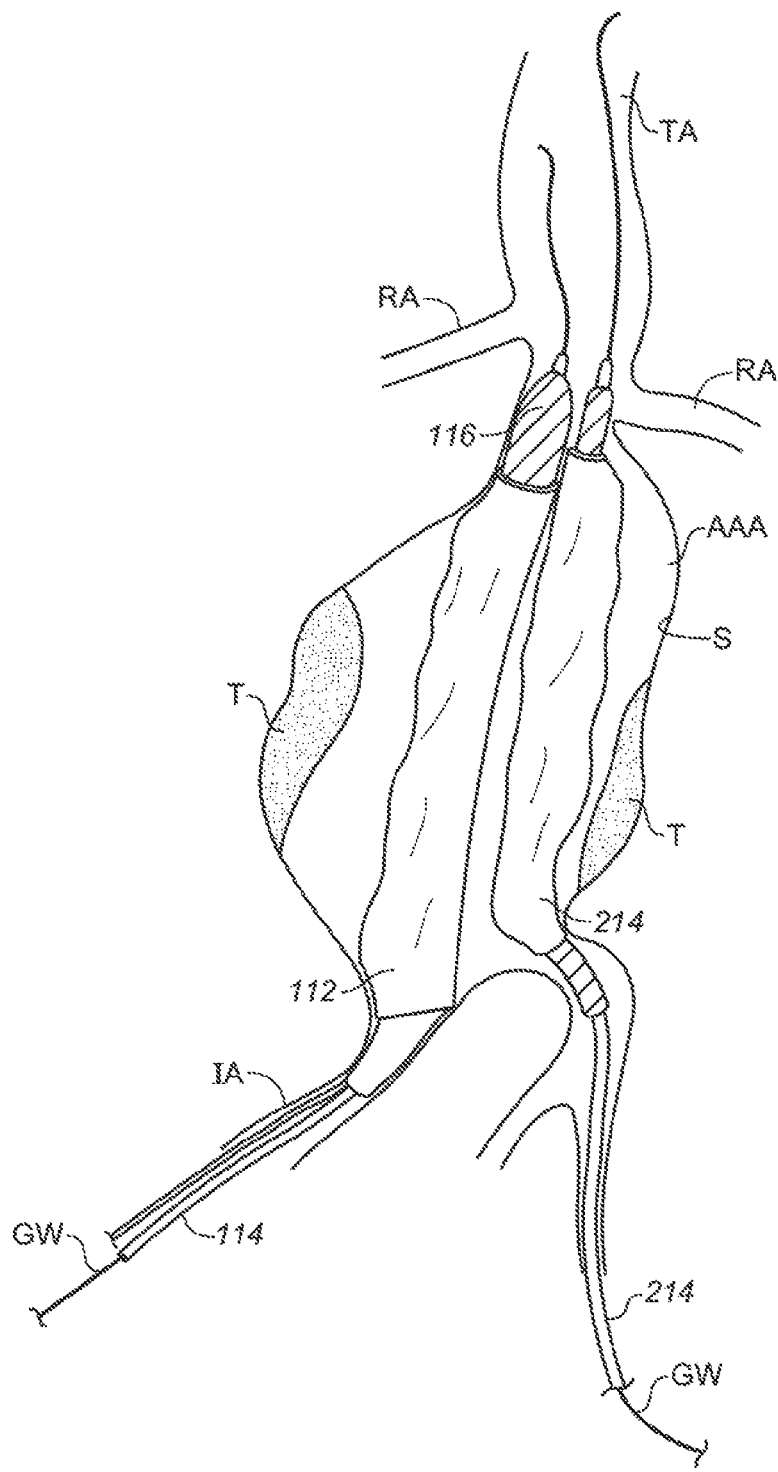
Figure 7E:
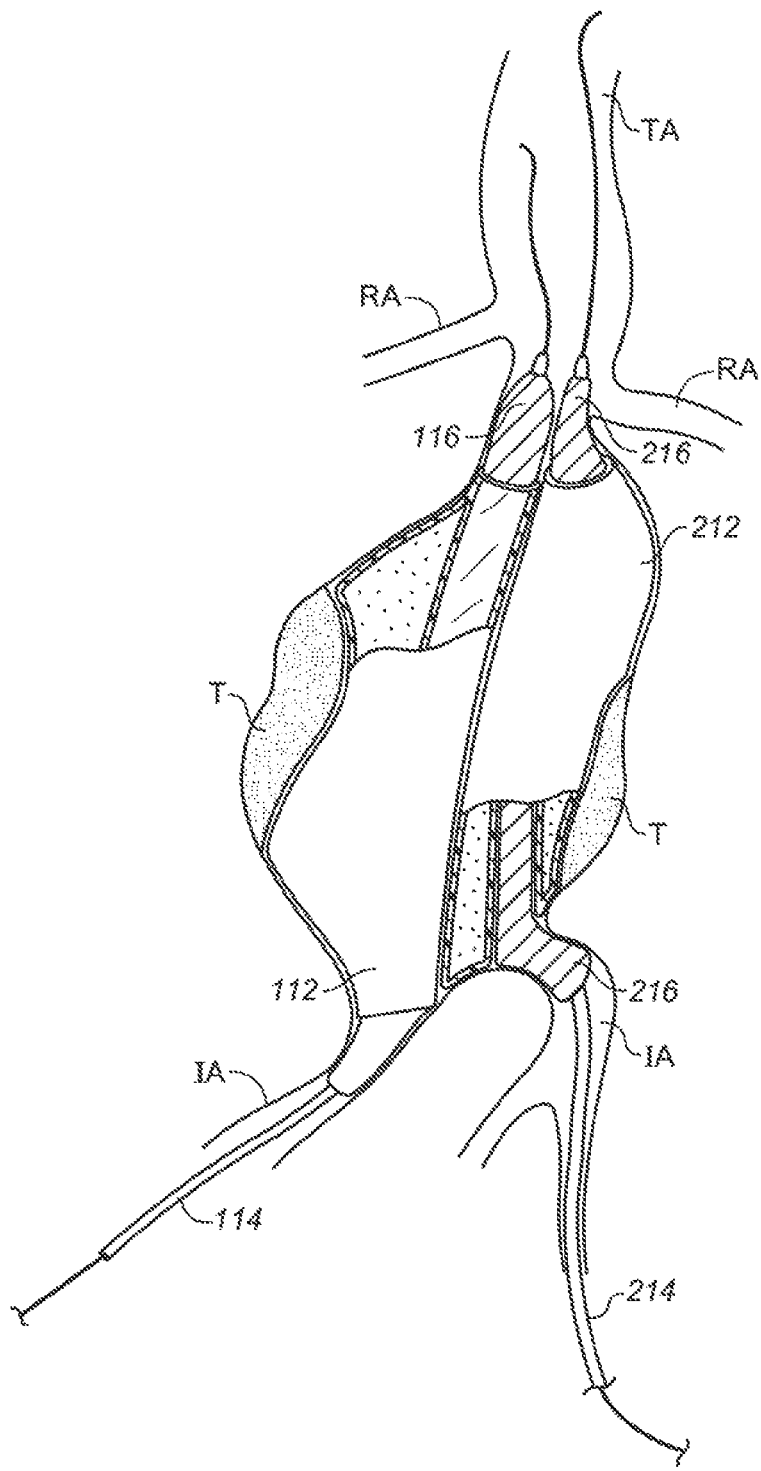

In treating an infrarenal abdominal aortic aneurysm using the pair of filling structures 112 and 212 illustrated in FIG. 6, a pair of guidewires (GW) will first be introduced, one from each of the iliac arteries (IA). As illustrated in FIG. 7A. The first delivery catheter 114 will then be positioned over one of the guidewires to position the double-walled filling structure 112 across the aortic aneurysm (AAA), as illustrated in FIG. 7B. The second delivery catheter 214 is then delivered over the other guidewire (GW) to position the second filling structure 212 adjacent to the first filling structure 112 within the aneurysm (AAA), as illustrated in FIG. 7C. As discussed herein below the two filling structures and associated balloons will be expanded simultaneously, a partially filled (in process) filling condition is illustrated in FIG. 7D where the filling structure 112 and balloon 116 are shown being simultaneously inflated to simultaneously expand to fill the aneurysmal volume, as illustrated in FIG. 7D. A completed filing is illustrated in FIG. 7E. The upper ends of the balloons 116 and 216 will conform the tubular lumens of the filling structures against the walls of the aorta as well as against each other, while the lower ends of the balloons 116 and 216 will conform the tubular lumens into the respective iliac (IA).

Figure 7F:
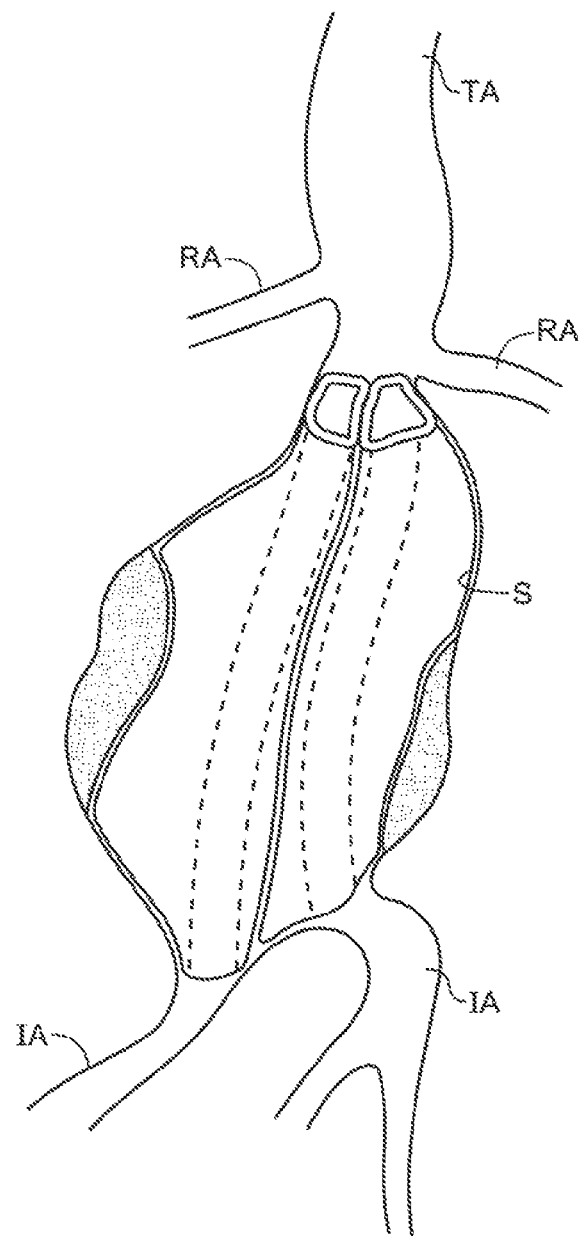

After filling the filling structures 112 and 212 as illustrated in FIG. 7E, the filling materials or medium will be cured or otherwise hardened, and the delivery catheters 114 and 214 removed, respectively. The hardened filling structures will then provide a pair of tubular lumens opening from the aorta beneath the beneath the renal arteries to the right and left iliac arteries, as shown in broken line in FIG. 7. The ability of the filling structures 112 and 212 to conform to the inner surface (S) of the aneurysm, as shown in FIG. 7F, helps assure that the structures will remain immobilized within the aneurysm with little or no migration. Immobilization of the filling structures 112 and 212 may be further enhanced by providing any of the surface features described above in connection with the embodiments of FIG. 2. Optionally, and not illustrated, anchoring or sealing structures could be provided in either of the upper or proximal openings of the tubular lumens into the aorta or from either of the distal or lower openings into the respective iliac arteries.

Figure 8:
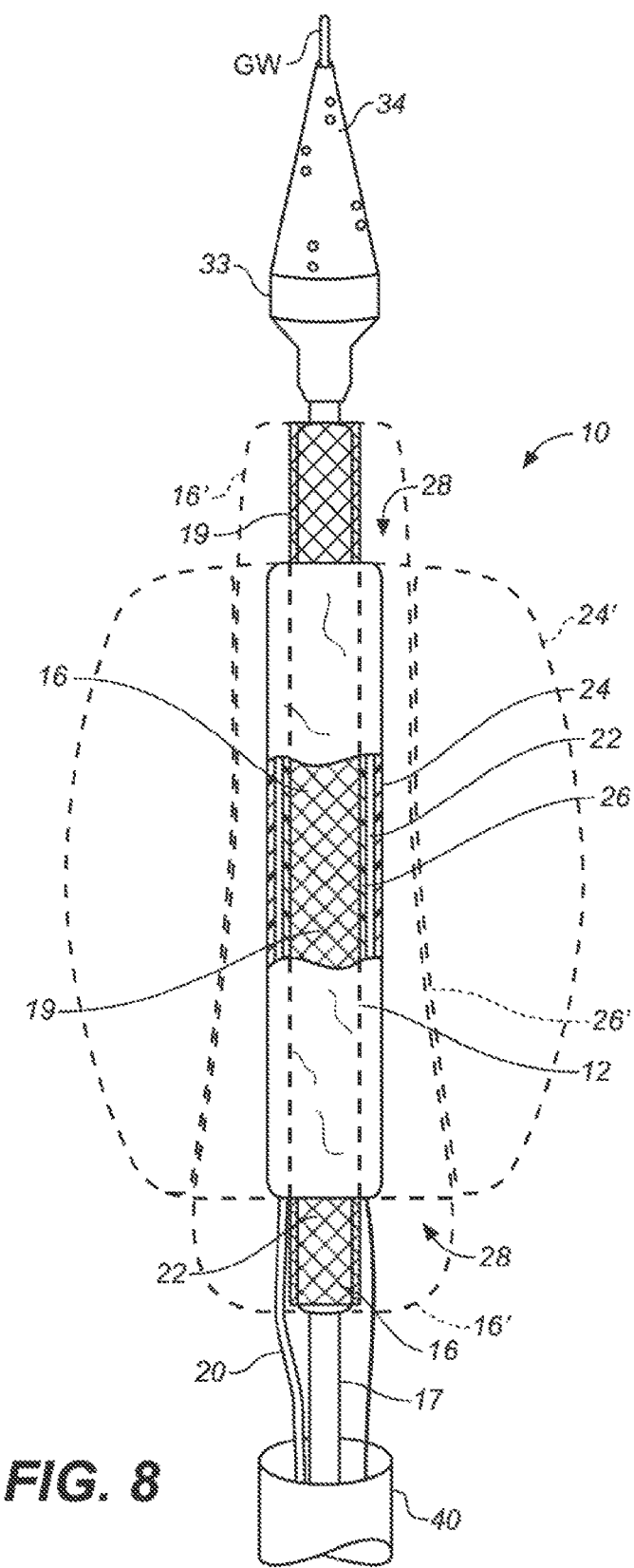
FIG. 8 illustrates an example of a delivery catheter shaft carrying a single prosthesis system which comprises a filling structure mounted over a endoframe structure.

Referring now to FIG. 8, shows a system 10 constructed for delivering a double-walled filling structure 12 (also referred to as an endograft in this disclosure) to an aneurysm. It includes the filling structure 12 disposed over a radially expandable endoframe 19, both of which are then mounted on a inner delivery catheter shaft 17 having an expandable element, typically an inflatable balloon 16, near its distal end and a nosecone 33 at its distal end. Nosecone 33 may be shaped to facilitate advancement of the delivery system through the vasculature and may include a series of side ports 34 for performing angiography before, during, or after deployment of the filling structure 12. An outer sheath 40 is slidably disposed over the inner delivery catheter shaft 17, the distal end of which interfaces with a proximal portion of nosecone 33 so as to facilitate advancement of the system through the vasculature of the patient. Expandable element 16 traverses the entire length of the endoframe 19 so that the endoframe 19 may be radially expanded upon expansion of the expandable element balloon 16 (expanded balloon 16' shown in broken line). Endoframe 19 traverses the entire length of filling structure 12 and most of endoframe 19 is covered by filling structure 12, however, endoframe 19 may also have proximal and a distal regions that extend uncovered beyond the filling structure 12. One of skill in the art will appreciate that lengths of the filling structure, endoframe and expandable element may be adjusted as required and thus the relative lengths are not limited to those disclosed above. Further details about the double-walled filling structure are disclosed in U.S. Patent Publication No. 2006/0212112 and embodiments of an endoframe are disclosed in U.S. Patent Application Publication No. 2010/0004728, both of which the entire contents are incorporated herein by reference.

The catheter 14 will comprise a guidewire lumen (not shown), a balloon inflation lumen (not shown) or other structure for expanding other expandable components, and a filling tube 20 for delivering a filling medium or material to an internal space 22 of the double-walled filling structure 12. The internal space 22 is defined between an outer wall 24 and inner wall 26 of the filling structure. Upon inflation with the filling material or medium, the outer wall 24 will expand radially outwardly (expanded outer wall 24 shown in broken line) as will the inner wall 26 (expanded inner wall 26' shown in broken line). Expansion of the inner wall 26 defines an internal generally tubular lumen 28 through which blood flows after deployment of the filling structure in the aneurysm. The expandable balloon 16 or other structure will be expandable to correspondingly expand the endoframe 19 to provide support and to shape an inner surface of the lumen 28. In this embodiment, the expandable balloon is cylindrically shaped and therefore the generally tubular lumen 28 will also be cylindrically shaped. In other embodiments, the balloon may be pre-shaped to more precisely match the curvature of the vessel. For example, when treating an aortic aneurysm, a tapered, pre-shaped or curved balloon may be used so that the lumen substantially matches the aorta. Various balloon configurations may be used in order to match vessel tortuosity. Pre-shaped, curved or tapered balloons may be used in any of the embodiments disclosed herein in order to obtain a desired lumen shaped.

Figure 9:
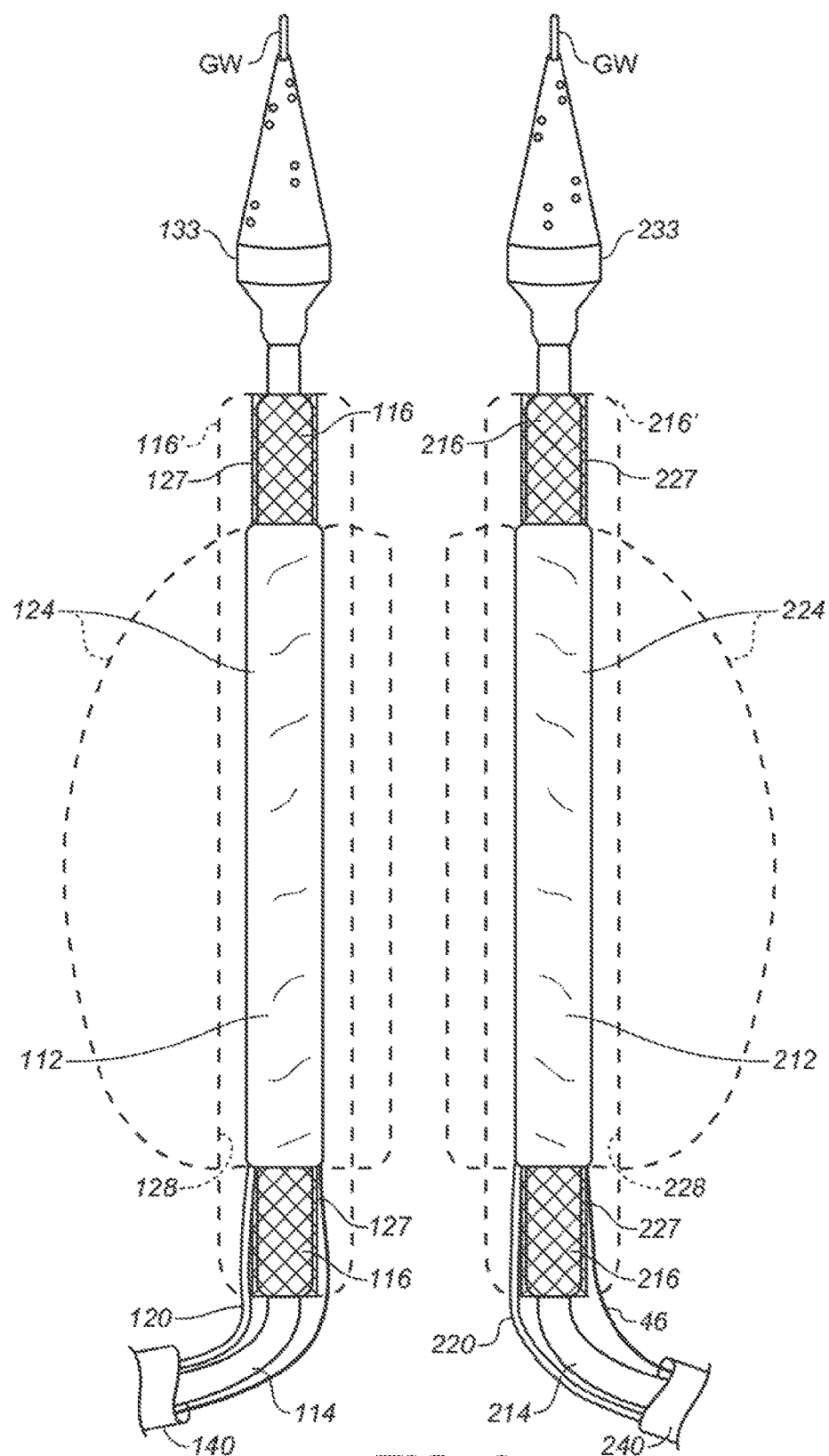
FIG. 9 illustrates an example of a system comprising a pair of prostheses for delivery to an infrarenal abdominal aortic aneurysm, where each prosthesis comprises a delivery catheter shaft carrying a fining structure mounted over an endoframe structure.

In a particular, a pair of double-walled filling structures will be used to treat infrarenal abdominal aortic aneurysms, instead of only a single filling structure as illustrated in FIG. 8. A system comprising such a pair of filling structures is illustrated in FIG. 9 which includes a first filling structure 112 and a second filling structure 212. Each of the filling structures 112 and 212 are mounted on delivery catheter inner shafts 114 and 214, respectively and each system also has a radially expandable endoframe 127, 227. Inner delivery catheter shafts 114 and 214 include fenestrated nosecones 133, 233 for performing angiography before, during or after treatment, and outer sheaths 140, 240 slidably disposed over the filling structure during advancement of the system through the vasculature along the guidewires (GW). The components of the filling structures 112 and 212, the endoframes 127, 227 and inner delivery catheter shafts 114 and 214 are generally the same as those described previously with respect to the single filling structure system 10 of FIG. 8. Corresponding parts of each of the filling systems 112 and 212 will be given identical numbers with either a 100 series number or a 200 series number. Filling structures 112 and 212 will generally be positioned adjacent each other within the aneurysmal space to fill that space, as will be described with specific reference to FIGS. 10A-10I below.

Figure 10B:
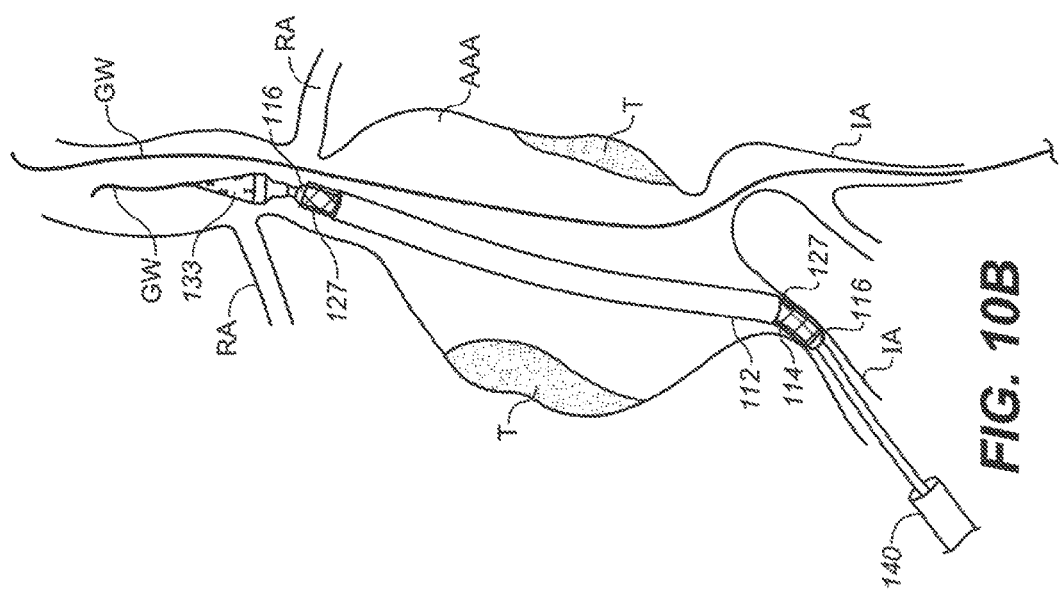
Figure 10A:
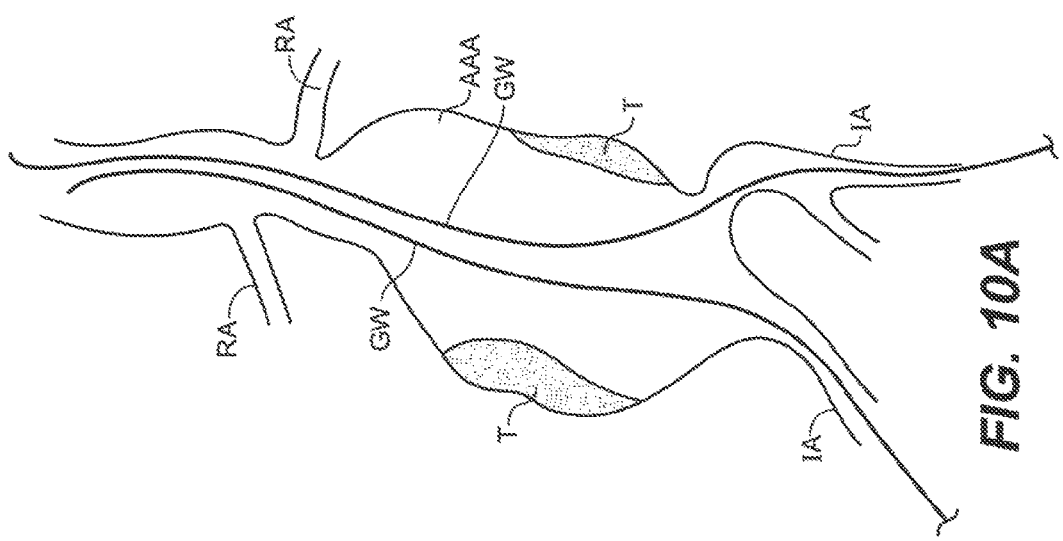
Figure 10C:
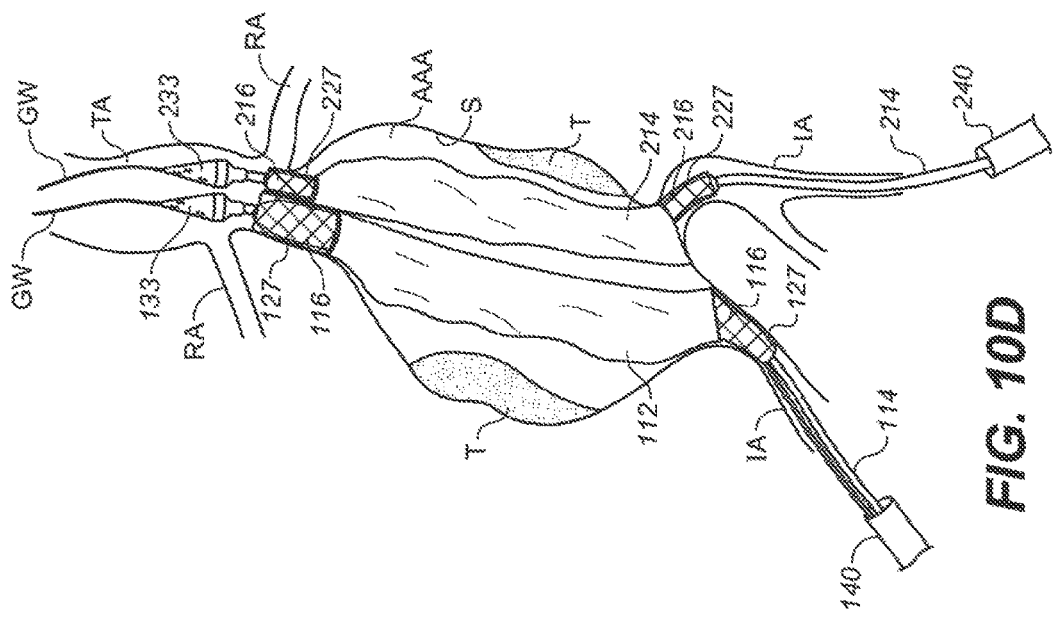

FIGS. 10A-10I illustrate an exemplary use of the system in FIG. 9 for treating an infrarenal abdominal aortic aneurysm AAA with or without mural thrombus T. After the inner delivery catheter shafts 114 and 214 are advanced so that the filling structures 112 and 212 are positioned at the treatment site, the outer sheaths 140 and 240 are retracted relative to the inner catheter shaft 114 and 214. The outer sheaths 140 and 240 are slidably disposed over the filling structures 112 and 212 and the corresponding endoframes 127 and 227 disposed therein. In FIG. 10A a pair of guidewires (GW) will first be introduced preferably percutaneously or by surgical cut down, from each of the iliac arteries (IA) and advanced across the aneurysm toward the renal arteries (RA). Referring now to FIG. 10B, the first delivery catheter shaft 114 having a fenestrated nosecone 133 at its distal end and an expandable balloon 116 disposed on a distal portion will then be advanced over one of the guidewires GW to position the double-walled filling structure 112 across the aortic aneurysm (AAA) along with endoframe 127. An outer sheath 140, slidably disposed over the filling structure 112 and inner shaft 114, is retracted to expose the filling structure 112 at the target treatment site. The second inner catheter shaft 214 having expandable balloon 216 and fenestrated nosecone 233 at its distal end is then delivered over the other guidewire GW to position the second filling structure 212 adjacent to the first structure 112 across the aneurysm (AAA) along with endoframe 197, as illustrated in FIG. 10C. The outer sheath 240, slidably disposed over the filling structure 212 and inner shaft 214, is retracted to expose the second filling structure 212 at the target treatment site.

In an exemplary method, first, the balloon 116 or 216 is expanded. Expanding the balloon 116 or 216 expands the corresponding filling structure 112 or 212 and endoframe 127, 227 disposed thereon. Next, the expanded filling structure 112 or 212 is filled with the fluid filling medium. Then, the balloon 116 or 216 is deflated to allow a flow of blood through the filling structure 112, 212 filled with the fluid filling medium, while the expanded endoframe 127, 227 maintains the patency of the generally tubular lumen within the expanded filled filling structure 112 or 212. In another embodiment, one or both of filling structures 112 or 212 are be filled with the fluid filling medium first, then the balloon 116 or 216 expanded to expand the endoframe 127 or 227 to form a generally tubular lumen in the corresponding filling structure 112 or 212. In still another embodiment, filling structure 112 or 212 is filled with the fluid filling medium simultaneously with expanding the balloon 116 or 216 disposed therein. Typical variations of deployment procedures may include: one of the filling structures 112, 212 and associated balloons 116, 216 being expanded first along with the corresponding endoframe 127, 227, followed by the other filling structure, endoframe and balloon. As discussed in the configurations described below, both balloons are radially expanded simultaneously thereby also expanding the filling structures and endoframes simultaneously.

Alternatively, one or both filling structures 112, 212 may be filled with a hardenable material and then the filling structures 112, 212 are radially expanded along with the corresponding endoframe 127, 227. In still other embodiments, combinations of filling and expanding may be performed in different order depending on physician preference and aneurysm anatomy. In some embodiments, an optional pre-filling step may be performed prior to filling with the hardenable filling medium. In this optional step, once the delivery system is positioned across the aneurysm, the filling structure may be filled with $CO_2$ gas, contrast media, saline or other fluids to unfurl the filling structure 12 away from the delivery catheter thereby helping to ensure more uniform filling later on and reduce or eliminate stiction between folds of the filling structure that may be present. During unfurling, the filling structure may be partially filled or fully filled so that it conforms to the inner aneurysm wall. Once unfurled, angiography may be performed through a fenestrated nosecone 133 or 233 on the inner catheters shafts 114 or 214 upstream of the aneurysm to detect leaks in the deployed filling structure 12. Once an optimal filling volume and pressure is determined to prevent the occurrence of endoleaks, the fluid may be removed from the filling structure and it may be filled with the hardenable material to expand and conform to the aneurysmal space between the lumens and the inner aneurysm wall. Pressure relief valves such as those described herein may also be used to ensure that the filling structure is not over filled. In order to prevent overfilling of the filling structure, any of the pressure relief valves disclosed below may also be used to bleed off excess fluid from the filling structure.

Figure 10D:
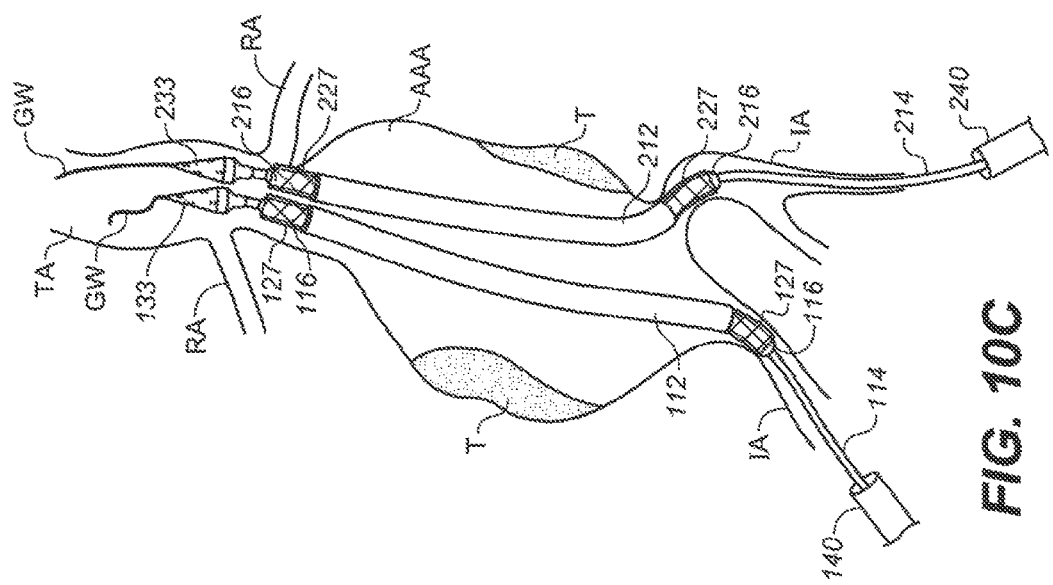
Figure 10F:
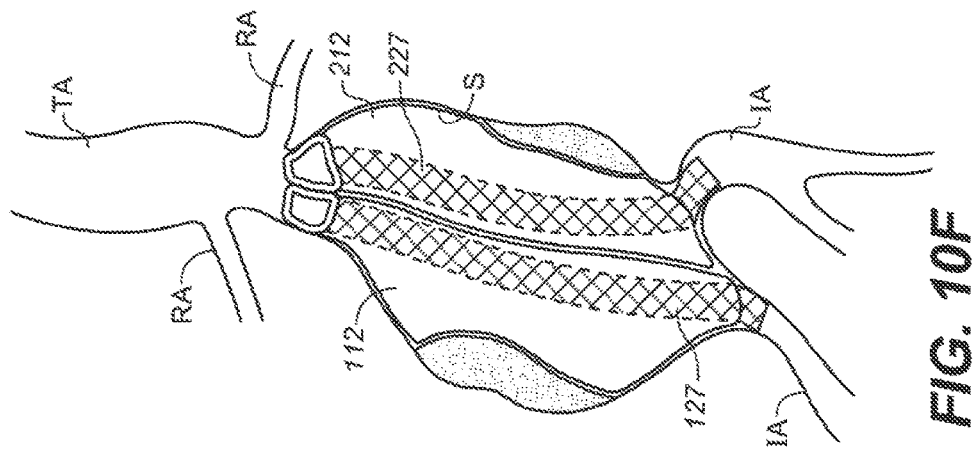
Figure 10E:
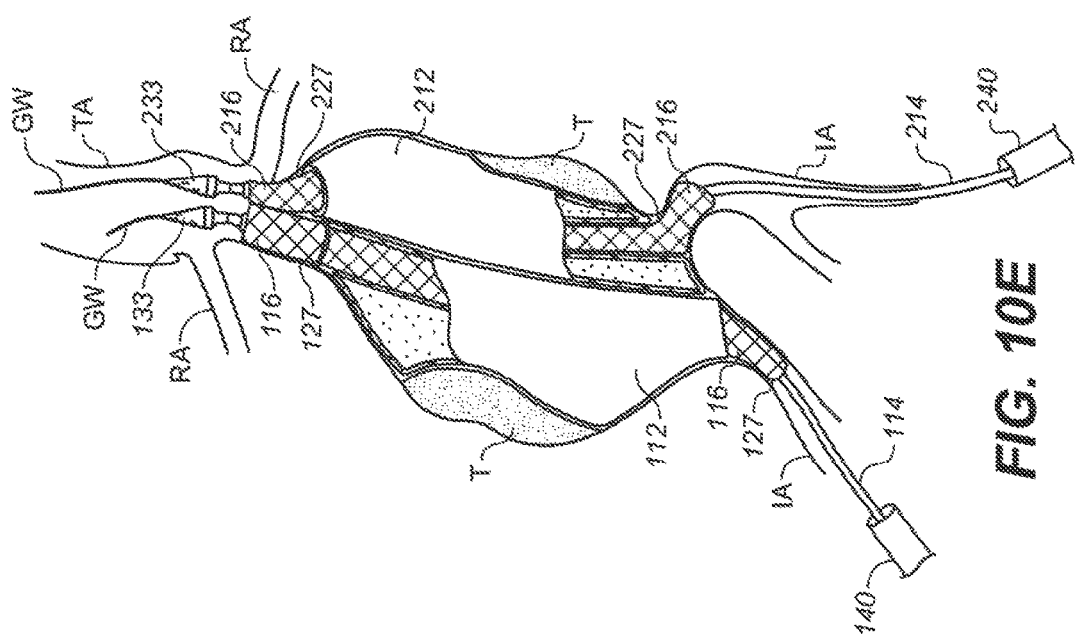

FIG. 10D illustrates the simultaneous inflation of both balloons 116, 216 along with endoframes 127, 227 in addition to expansion and filling of filling structures 112, 212. The filling structures and balloons are expanded and inflated to fill the aneurysmal volume in contact with the aneurysmal wall and each other, as illustrated in FIG. 10E. U.S. Patent Publication No. 2006/0212112 discloses filling of one filling structure in more detail including pressures, filling materials and other details, the entire contents of which have previously been incorporated herein by reference. FIG. 10E also illustrates a cut away view of the expanded endoframes 127, 227 within the filled filling structures 112, 212. The upper ends of the balloons 116 and 216 will conform the tubular lumens of the filling structures against the walls of the aorta as well as against each other, while the lower ends of the balloons 116 and 216 will conform the tubular lumens into the respective iliac artery, IA. The expanded endoframe 127 not only provides support to filling structure 112, but also creates and shapes a lumen for blood passage from the aorta to one of the iliac arteries. Similarly, expanded endoframe 197 also provides a lumen for blood passage from the aorta into the other iliac artery. In some protocols filling of the filling structures (either both filled simultaneously or one after the other) may be performed before, during or after radial expansion of the balloons and the endoframe 127, 227 (either both expanded simultaneously or one after the other). Additionally, as discussed above with respect to FIG. 9, the endoframes 127, 227 may be radially expanded using a cylindrically shaped balloon to form a substantially cylindrically shaped lumen. Curved, tapered or pre-shaped balloons may also be used to expand the endoframes 127, 227, thereby forming a lumen that also is curved, tapered or shaped. The curved, tapered or pre-shaped balloon may be selected to match the anatomy of the vessel in which the endoframe and endograft is placed. Pre-shaped, curved or tapered balloons may be used in any of the other embodiments disclosed herein in order to obtain a desired lumen shape.

After filling the filling structures 112 and 212 as illustrated in FIG. 10E, the filling materials or medium will be cured or otherwise hardened as described in U.S. Patent Publication No. 2006/0212112 and the inner delivery catheter shafts 114 and 214 removed, respectively. The hardened filling structures along with the expanded endoframes 127, 227 will then provide a pair of tubular lumens opening from the aorta beneath the renal arteries to the right and left iliac arteries, as shown more clearly in broken line in FIG. 10F. The ability of the filling structures 112 and 212 to conform to the inner surface (S) of the aneurysm, as shown in FIG. 10F, helps the structures to remain immobilized within the aneurysm with little or no migration. Immobilization of the filling structures 112 and 212 may be further enhanced by providing any of the surface features described in U.S. Patent Publication No. 2006/0212112 which has been incorporated herein by reference.

The double filling structure embodiments may include at least one endoframe deployed within each of the tubular blood flow lumens. The endoframes will generally be endoskeletal structures that lay the foundation for new lumens, and will be deployed within the tubular lumens of the double-walled filling structures using balloon or other expansion catheters (in the case of malleable or balloon-expandable endoframes) and an optional retractable constraining sheath. FIG. 10G more clearly shows the first endoframe 127 disposed within the generally tubular lumen of the first filling structure 112 while a second endoframe 197 is disposed in the tubular lumen of the second filling structure 212. As illustrated, in this exemplary embodiment, the endoframes are balloon expandable structures which extend into the iliac arteries IA at the lower end of the filling structures. In other embodiments, the endoframes may be self-expanding endoframe-like structures fabricated from a shape memory alloy such as Nitinol.

Referring now to FIG. 10H, first and second endoframes 127 and 227 may extend upwardly on the aortic side of the first and second filling structures 112 and 212. In such embodiments, the first and second endoframes 127 and 227 may be constructed so as to not obstruct the renal arteries. For example, the first and second filling structure 112 and 212 may include a side hole so as to allow flow of blood through the renal arteries (RA). When the endoframe structures extend into the thoracic aorta TA, it will usually be desirable that they be expanded so that they conform to each other along a plane or region of contact. For example, as shown in FIG. 10I, the upper ends of the endoframes 127, 227 may be formed from their respective expansion balloons and manufacturing shape treatments to have D-shaped cross-sections when expanded, although other cross-sections such as elliptical, circular, etc. may be formed. Thus, flat faces 258 and 260 will engage each other with the remaining portion of the endoframe conforming to the inner wall of the aorta. In this way, most of the cross-sectional area of the aorta will be covered with the endoframe, thus enhancing blood flow through the filling structures. Other configurations are disclosed in U.S. Patent Publication No. 2006/0212112 previously incorporated herein by reference.

In the exemplary embodiment of FIGS. 10A-10I, each endoframe and filling structure is both disposed coaxially and generally concentrically over an expandable member coupled to a delivery catheter and the entire system is delivered to the aneurysm at one time. Such a coaxial and concentric system, such as that shown in FIG. 8, typically includes a filling structure 12, also referred to as an endograft that is coaxially disposed over the endoframe 19, both of which are then coaxially and concentrically positioned over a radially expandable balloon 16 which is coupled to the distal region of a inner shaft 17. Proximal and distal portions of endoframe 19 may extend uncovered by filling structure 12 and a filling tube 20 allows a fluid to be delivered to the filling structure 12. Under certain conditions, endoleaks occur, thereby resulting in incomplete occlusion of the aneurysm. Although a separate angiography catheter may be useful to visualize the blood flow through the aneurysm and detect endoleaks during deployment, a separate angiography catheter would likely increase the profile and further complicate the method of delivery. Additionally, in certain situations, the filling structure may move relative to the endoframe during delivery, thereby resulting in inaccurate placement of one or both devices. It would therefore be advantageous an integrated system provide a system that can perform an angiography procedure without substantially increasing the profile of the delivery system or over complicating the procedure. It would be further advantageous for such a system to provide more effective ways of coupling the filling structure and endoframe to the delivery catheter to inhibit movement and facilitate more accurate delivery of the endoframe and endograft to the treatment site.

FIGS. 11A-11B illustrate an exemplary embodiment of a delivery system having a fenestrated nosecone 33 and a retractable outer sheath 40, as shown both during delivery of the system to the aneurysm (FIG. 11A) and during deployment of the filling structure at the aneurysm (FIG. 11B). The exemplary embodiment includes an inner shaft 17 having a filling structure 12 and endoframe 19 disposed thereon, and an outer sheath 40 slidably disposed over the inner shaft 17, filling structure 12 and endoframe 19. Nosecone 33, attached to the distal end of inner shaft 17, includes a lumen extending therethrough, preferably a single through lumen, the through lumen connected to a guidewire lumen of the inner shaft 17, such that the nosecone and inner shaft can be simultaneously advanced along the same guidewire GW. The nosecone includes a series of sideports 34 in fluid communication with the through lumen for performing angiography before, during or after deployment of the filling structure 12. The system includes releasable coupling mechanisms to attach filling 10 and endoframe 19 to inner delivery catheter 17 during delivery of the system to the aneurysm (shown in detail in FIGS. 20A-20E). The distal end of outer sheath 40 releasably couples with the nosecone to facilitate advancement of the system through a patient's vasculature, as illustrated in FIG. 11A. A marker band 31 may be disposed near the interface on one or both of the proximal portion of nosecone 33 and the distal end of the outer sheath 40, so as to allow a user to visualize the location of the outer sheath 40 relative to the filling structure 12. Once the filling structure is positioned as desired, outer sheath 40 can be retracted relative to the filling structure 12 and inner shaft 17, as shown in FIG. 11B, thereby exposing the filling structure for deployment within the aneurysm. The fenestrated nosecone remains attached to the end of the inner shaft 17 distal of the filling structure 12 so that an angiography procedure may be performed. For example, as shown in FIG. 11B, a contrast media 38 may be injected through the guidewire lumen of the inner shaft 17 and out through the side ports 34 of the nosecone 33 into the vasculature. In one embodiment, outer sheath 40 is retracted by pulling proximally on an annular knob 57 depicted in FIG. 15. After deployment and release of the filling structure and endoframe from the inner catheter, outer sheath 40 can be advanced, typically using knob 57, so as to interface with nosecone 33 to facilitate withdrawal of the system from the patient.

Figure 12:
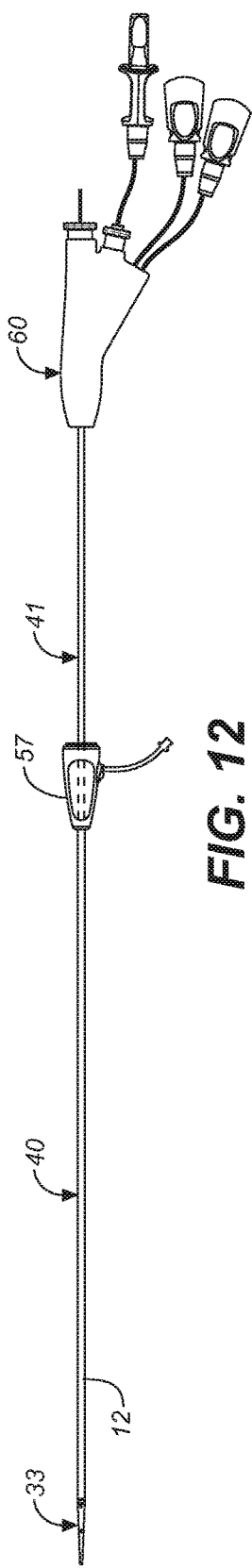
FIG. 12 shows an exemplary aneurysm treatment system having a fenestrated nosecone, a carrier knob and a handle.

FIG. 12 shows an exemplary embodiment of the delivery system, which includes the fenestrated nosecone 33, an outer sheath 40, a filling structure 12 (not shown) disposed within outer sheath 40, an annular carrier knob 57 for retracting the outer sheath 40, and a handle 60. In an exemplary method of treating an aneurysm, the system, as shown in FIG. 12, is inserted into the vasculature of the patient. The distal tapered shape of nosecone 33 and the smooth transition between the nosecone 33 and outer sheath 40 coupled thereto facilitates advancement of the system through the vasculature of the patient. Once the filling structure 12 is positioned at the aneurysm treatment site, the physician may retract the outer sheath 40 by pulling carrier knob 57 proximally, thereby retracting outer sheath 40 over hypotube 41 proximal of knob 57. The carrier knob 57 is fixedly attached to the proximal end of outer sheath 40 and includes a seal between outer sheath 40 and hypotube 41. Handle 60, disposed at the proximal end of inner shaft 17 is used to advance and withdraw the system, as well as to deploy the (fillable) filling structure 12 or perform angiography through nosecone 33.

Fenestrated Nosecone

Figure 13:
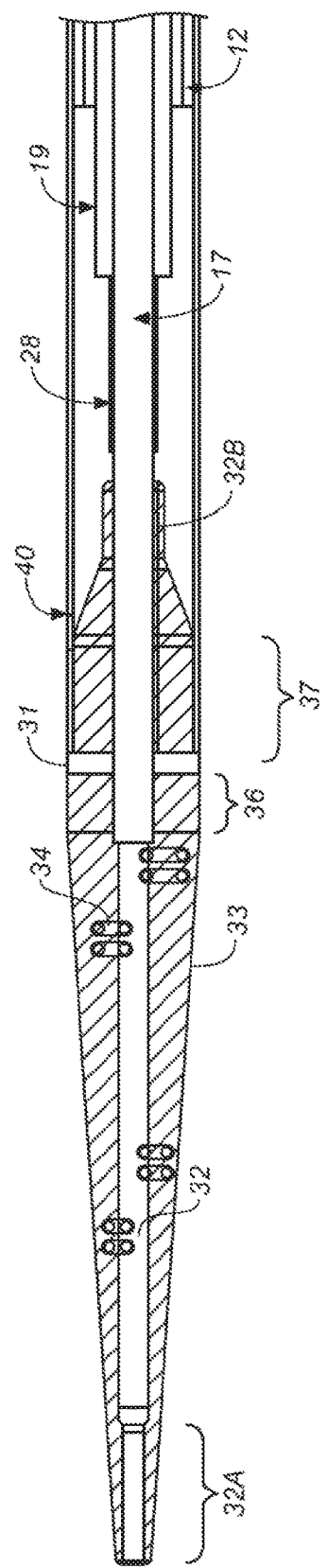
FIG. 13 illustrates the fenestrated nosecone of the system of FIG. 12.

FIG. 13 illustrates the nosecone 33 of the embodiment of FIG. 12 in more detail. Although shown in the embodiment of FIG. 12, nosecone 33 may be incorporated into any of the embodiments disclosed herein. Nosecone 33 is distally tapered and includes a through lumen 18 extending along a longitudinal axis of the nosecone to facilitate advancement of the system over a guidewire through the vasculature. Nosecone 33 is also fenestrated having a series of sideports in fluid communication with the through lumen for performing angiography. The through lumen 18 of the nosecone is sized so as to simultaneously receive a guidewire and a flow of contrast media for performing angiography through the side ports 34. The fenestrated nosecone 33 is advantageous as it facilitates both advancement of the system over a guidewire and delivery of contrast media in an angiography procedure through the same lumen while the guidewire is disposed therein, thereby simplifying the procedure while maintaining a reduce profile.

To facilitate both advancement of the system and deployment of the filling structure, fenestrated nosecone 33 releasably couples or interfaces with the distal end of outer sheath 40. In an exemplary embodiment, nosecone 33 includes an isodiametric portion 36 which is isodiametric with the outer diameter of the distal end of outer sheath 40 so as to create a smooth transition at the interface and prevent "snowplowing" against a vessel wall as the system advances through the patient's vasculature. Isodiametric portion 36 extends a distance distal of the interface so as to increase the stiffness of the nosecone near the interface and prevent flexure of the nosecone and/or outer sheath at the interface during advancement of the system. Nosecone 33 may also include a portion 37 having an outside diameter slightly smaller than the inside diameter of the distal end of outer sheath 40; thus, portion 37 is disposed within the outer sheath 40 such that the outer sheath 40 fittingly receives portion 37 so as to releasably couple with the nosecone 33. Portion 37 may extend a distance proximal of the interface so as to increase the stability of the coupling and to increase the stiffness near the interface to prevent separation between the nosecone and outer sheath 40 as the system winds through complex or tortuous vasculature, thereby further reinforcing the smooth transition between the nosecone 33 and the outer sheath 40 to reduce the likelihood of "snowplowing" against the vessel wall. The nosecone 33 and/or the outer sheath 40 may further include a radiopaque marker band 31 near the interface to allow a physician to image the location of the distal end of the outer sheath 40 relative to nosecone 33. The resin to manufacture the nosecone may also include a radiopaque filler to facilitate imaging during the procedure.

Nosecone 33 is dimensioned to facilitate advancement in a patient's vasculature. An exemplary nosecone may be between 1 to 4 inches in length, preferably 2.5 to 3 inches, and have an outside diameter tapering from about 0.25 inches at a proximal end to about 0.050 inches at a distal end. The through lumen 18 extending through the nosecone 33 may also reduce in size as the outside diameter tapers down. For example, the through lumen at the proximal end 32B may be between 0.05 and 0.1 inches, preferably about 0.08 inches, and reduce in size gradually or incrementally to 0.02 to 0.04 inches, preferably about 0.05 inches at the distal portion 32A of nosecone 33.

Angiography may be performed by injecting a contrast media through the guidewire lumen of the inner shaft 17, which then flow into the through lumen 18 of nosecone 33 and out the side ports 34, preferably while the guidewire GW is disposed within the guidewire lumen and through lumen 18. Angiography may be performed through nosecone 33 before, during, or after treatment of the aneurysm, and is useful for imaging the flow of blood, particularly for detecting leaks in an endograft deployed in an aneurysm. In an angiography procedure, a radiopaque contrast media is delivered into a blood vessel and an X-ray based imaging technique, such as fluoroscopy, is used to image the flow of the contrast media as it flows through the blood vessel. Thus, the contrast media is released uniformly into the blood vessel so that the imaging produces a more accurate representation of blood flow through the vessel.

In an many embodiments, fenestrated nosecone 33 includes pairs of side ports 34 arranged in a series equally distributed along the nosecone in a helical fashion so as to evenly distribute the contrast media into the vasculature. Preferably, each of side ports 34 extends in an orthogonal direction from the longitudinal axis of the nosecone 33. In an exemplary embodiment, the nosecone 33 comprises a series of 4 to 10 pairs of side ports 34, preferably 5 to 7 pairs of side ports, arranged in a helical fashion as described above. Typically, a side port 34 has a diameter within a range of 0.01 inches to 0.05 inches, and more preferably within a range of 0.03 to 0.04 inches.

Figure 14:
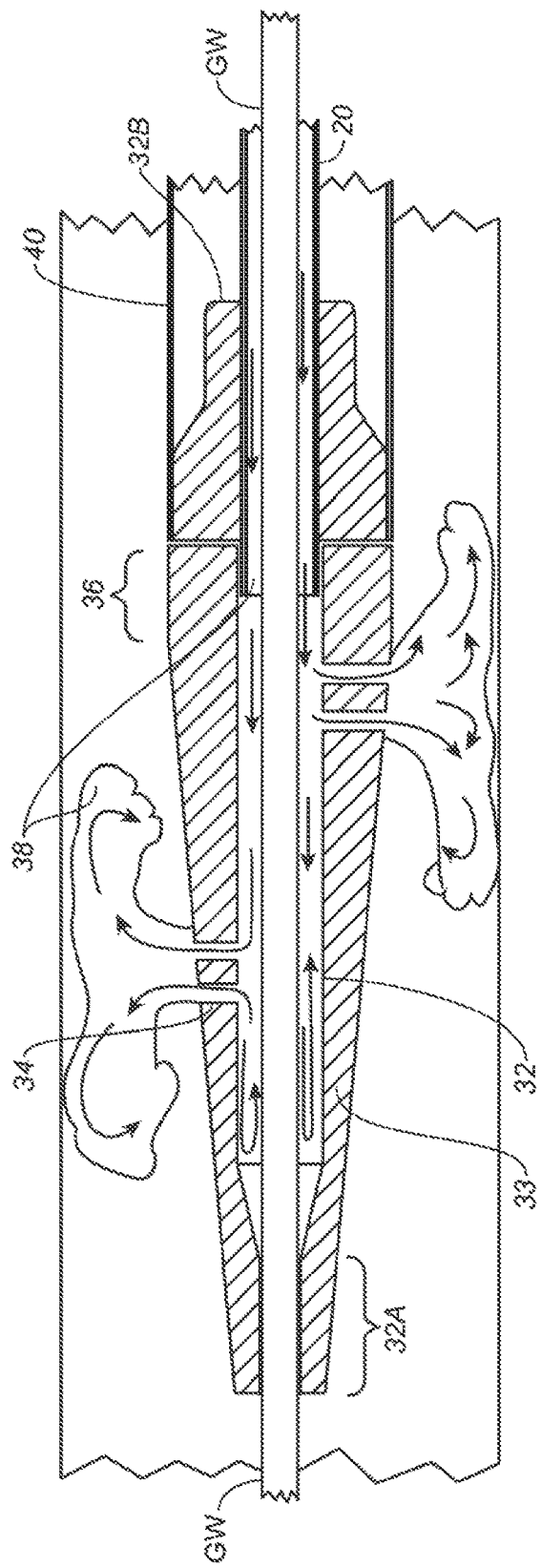
FIG. 14 depicts angiography as performed with the nosecone of FIG. 12.

FIG. 14 illustrates the nosecone 33 having a guidewire GW disposed within guidewire lumen 18 as well as a flow of contrast media 38 through a portion of guidewire lumen 18. In an exemplary embodiment, the guidewire lumen 18 includes a distal portion 32A which is reduced in size from the guidewire lumen 18 at the proximal end of nosecone 33. Distal portion 32A of the through lumen 18 is sized to slidably receive the guidewire and fit so as to inhibit flow of contrast media through the distal opening when the guidewire is disposed therein. The portion of the through lumen 18 proximal of portion 32A, however, is sized to simultaneously receive the guidewire and facilitate flow of contrast media 38. The narrowed distal region 32A of through lumen 18 substantially inhibits flow of contrast media through the distal opening of the nosecone, thereby directing the flow of contrast media through the side ports 34 and into the vasculature of the patient, as illustrated in FIG. 14.

Annular Knob

Figure 15:
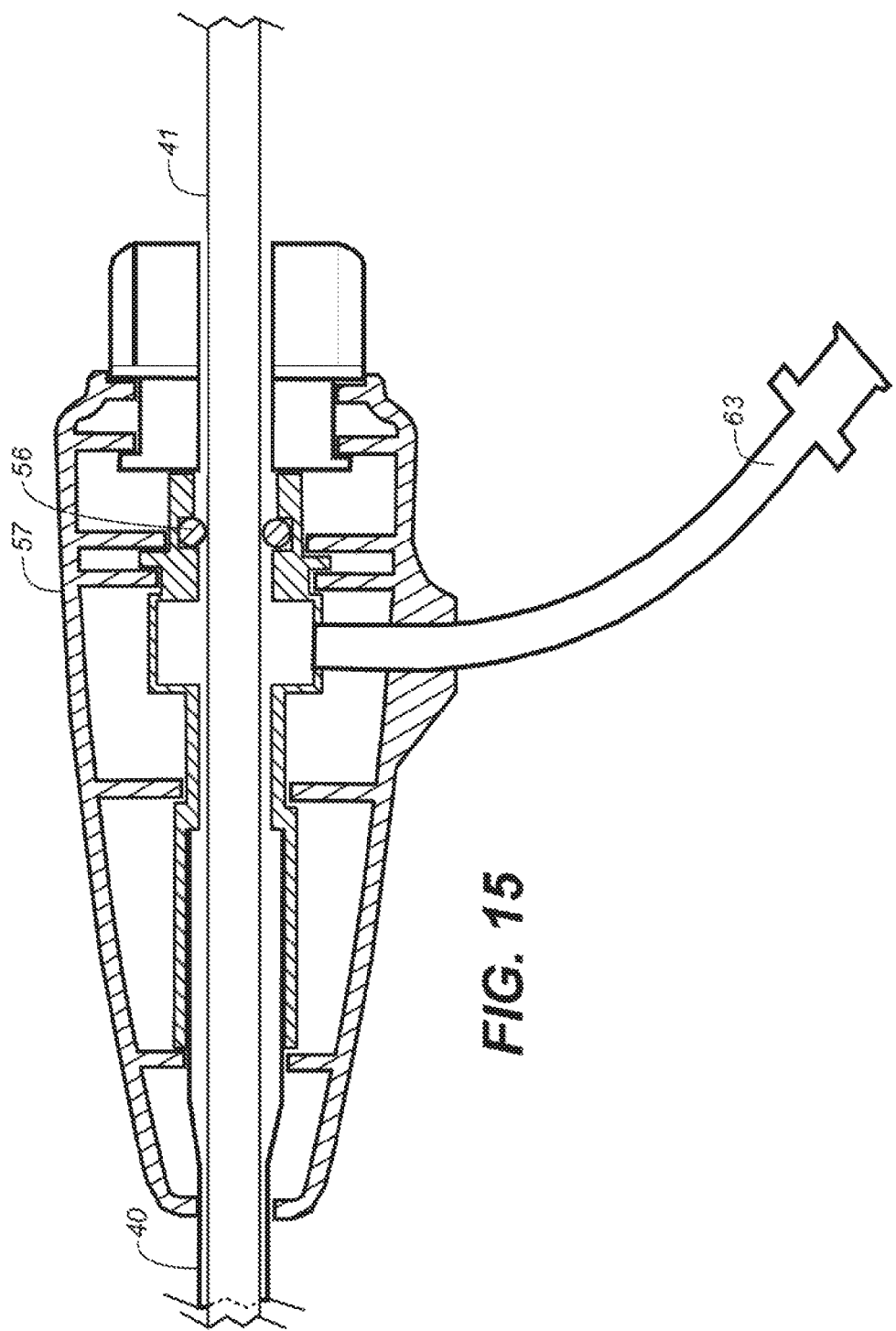
FIG. 15 illustrates the annular carrier knob of the system of FIG. 12.

FIG. 15 illustrates the carrier knob of the system of FIG. 12, the carrier knob coupling the proximal end of outer sheath 40 with hypotube 41. In such an embodiment, the outer sheath 40 is slidably disposed, at least partially, over hypotube 41 (main catheter shaft) when outer sheath 40 is retracted. In use, outer sheath 40 is retracted relative to the inner shaft 17 to expose the filling structure 12, endoframe 19 and expandable member, i.e., balloon 16, on a distal region of inner shaft 17. The carrier knob 57 is fixedly coupled to the proximal end of the outer sheath 40, preferably with a heat bond, so that a physician may manually pull the carrier knob 57 to retract outer sheath 40 over hypotube 41. Carrier knob 57 may also include an internal seal. The carrier knob 57 may comprise any material, such as polyetheramide, which can be bonded with the outer sheath 40.

Carrier knob 57 may include an internal seal 56, such as an silicone O-ring, to prevent fluid outflow from between the distal and proximal segments of the outer sheath 40. Typically, the blood pressure of the patient against internal seal 56 is sufficient to prevent fluid outflow from the body between outer sheath 40 and hypotube 41. As the carrier knob 57 is pulled proximally internal seal 56 slides proximally contacting the outer surface of the hypotube 41 and inside the annular knob 57.

Carrier knob 57 may be heat bonded to the outer sheath 40 by covering the proximal end of outer sheath 40 by a laminate material, preferably a polymer material such as Pebax®, placing a cavity in the knob 57 over the laminate covered outer sheath 40, and heating the assembly so that the laminate bonds to the outer shaft 40 and/or the knob 57, preferably bonding with both the outside surface of outer sheath 40 and the inside surface of the knob 57. The system may further include a retaining mechanism to prevent the hypotube 41 from slipping out of the knob 57 when the outer sheath 40 is advanced. The retaining mechanism may comprise a collar, a ring, a pin, a screw or any mechanism suitable to maintain a slidable coupling between the hypotube 41 and the annular knob 57. The system may also include a keying mechanism to prevent rotation between hypotube 41 (main catheter shaft) and sheath 40. Knob 57 include a sheath flush line 63, to allows flushing of the sheath or shooting contract through the sheath during the treatment procedure.

Handle

Figure 16:
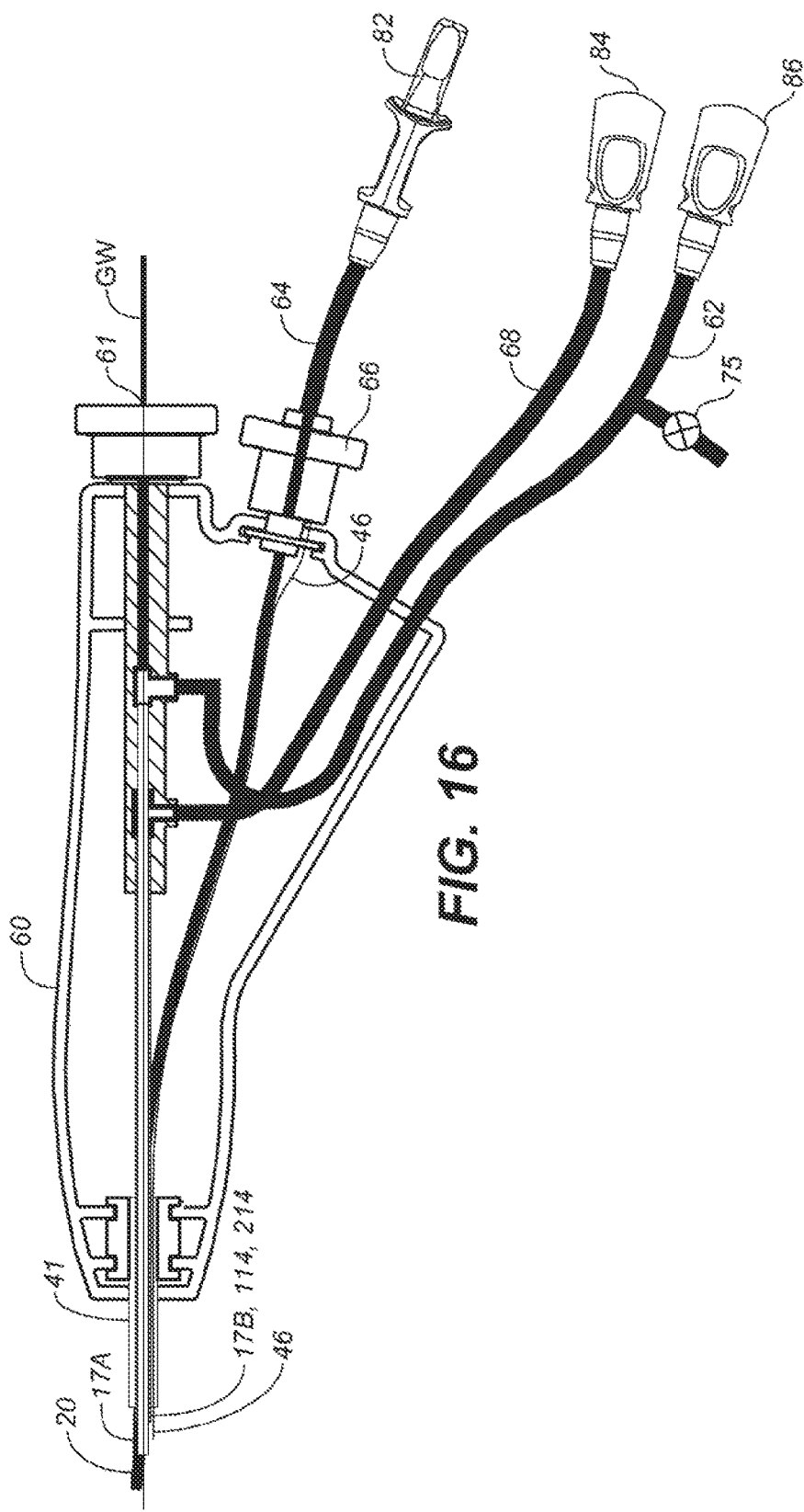
FIG. 16 illustrates the handle of the system of FIG. 12.

FIG. 16 illustrates a handle 60 of an exemplary delivery system of FIG. 12. Handle 60 include a body having a guidewire access port 61, an angiography line 62, a fill tube line 64, a release wire port/connector 66, and a balloon inflation line 68. The angiography line 62 provides access to the guidewire lumen such that contrast media can be injected through the guidewire lumen and out the series of side ports 34 of the nosecone 33. As the contrast media may be viscous, the backend pressure needed to perform angiography may reach 1,000 psi or more. These pressures may potentially cause the guidewire to "shoot" out of the guidewire lumen. To prevent this from happening, the guidewire access port 61 may include a locking mechanism for locking guidewire GW to the handle during the angiography process. Thus, angiography line 62 provides access to the guidewire lumen, while the guidewire access 61 may seal and lock the guidewire GW into place. Release wire access port/connector 66 provides access for removal of the release wire so as to decouple the coupling mechanisms and release the deployed filling structure from the inner shaft 17. Release wire access port/connector 66 may include a threaded luer type connector, which is fixed to the proximal end of the release wire, such that removing the port connector (along with the filling structure fill tube 64) and pulling in the proximal direction will retract the release wire and decouple the coupling mechanisms. Optionally, handle 60 may rotate on its inner and outer shafts to prevent undesired transfer of torque to the catheter shafts. The descriptions of additional components depicted are included in the descriptions of FIGS. 18 and 21.

A pressure monitor 69 is utilized to monitor the filling structure filling pressure during the treatment procedure. Typically, the pressure monitor is fluidly coupled with the filling tube circuit so as to monitor the system filling pressure during filling of the filling structure 12 with the hardenable medium.

Pressure Monitoring

In an exemplary method of simultaneous action in deploying filling structures and endoframes in separate catheters, pressure monitoring may be utilized in the following way.

After two filling structures have been delivered to the treatment site, both endoframes are radially expanded to help create a lumen for blood flow through the filling structure across the aneurysm. Using data from a patient's computerized tomography (CT) scans, a fill volume of the aneurysm treatment site may be estimated. This represents the baseline filling volume for both filling structure and is the minimum expected volume of filling material to be injected into the filling structure feed circuitry. Syringes or other injection devices coupled with a pressure gage may be used to optionally pre-fill each filling structure with contrast material using the baseline volume and the resulting baseline fill pressure may be noted. In addition, the pressure monitoring system may include a pop-off valve to relieve excess pressure in the event of overfilling. The pressure monitoring system may include a sensor inside the filling structure and a sensor monitoring the patient's systolic and or diastolic blood pressure used for calculating the patient's differential blood pressure. A differential blood pressure reading between the filling structure and the patient's systolic and or diastolic pressure simplifies the process of filling the structures as this allows the physician to accurately target the pressure inside the filling structure. This allows unfurling of the filling structure and provides a preliminary assessment of how the expanded filling structures fit into the aneurysmal space. Once this is accomplished, the contrast material is removed from the filling structures (in a method utilizing a pre-filling step). Again using the patient CT data, a functional fill volume may be determined. This volume is a percentage of the aneurysm volume obtained from the CT data, or it may be a predetermined number and is the volume of filling material that effectively seals and excludes the aneurysm. Functional fill pressure will be the pressure at which the functional fill volume is attained. A polymer fill dispenser may then be used to fill each filling structure with the functional fill volume and the functional fill pressure is noted. While holding the functional fill volume and pressure, the filling structure may be observed under fluoroscopy to check for proper positioning, filling and the absence of leakage across the aneurysm. If leaks are observed, additional polymer may be added to the filling structures until the leaks are prevented or minimized. Excessive additional polymer should not be added to the filling structure in order to avoid exceeding a safe fill volume or safe fill pressure. Once the physician is satisfied with the filling and positioning of the filling structures, stopcocks to the filling structures may be closed to allow the polymer to harden and then the delivery devices may be removed from the patient.

Figure 17:
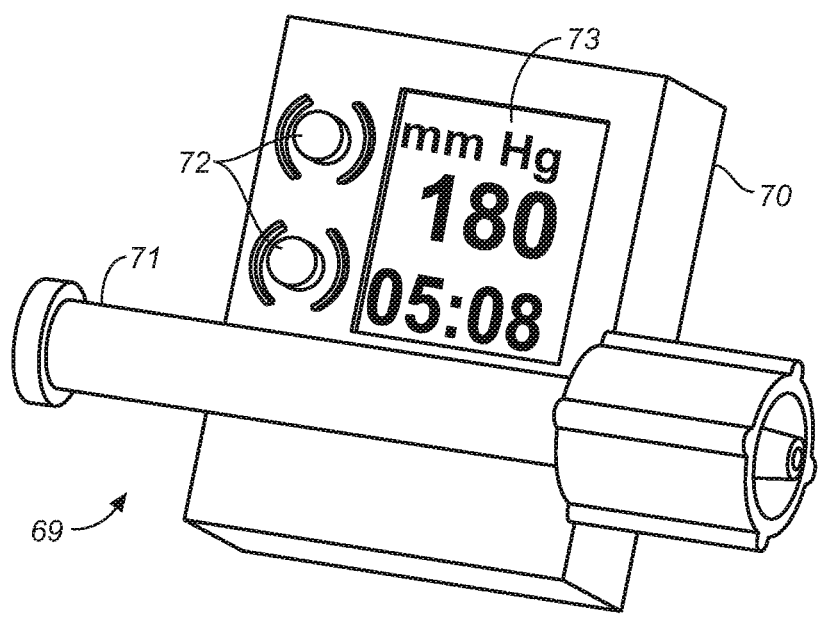
FIG. 17 illustrates an exemplary pressure monitor.

FIG. 17 illustrates a pressure monitor 69 comprising an integrated pressure gauge transducer. Pressure monitor 69 may include a body 70, a pressure fitting 71, control buttons 72, and a digital display 73 for reading the pressure and time output. The body 70 may include pressure transducers for determining the pressure and/or differential pressure. Pressure fitting 71 couples the pressure transducers of the body 70 to the filling system, control buttons 72 allow a user to adjust the pressure or the pressure or time readout. The pressure fitting 71 may include a tubular member and a luer cap for fluidly coupling with a filling line of the delivery system 10. Pressure monitor 69, or a portion thereof, may be re-usable or disposable, preferably the pressure transducers are for a single use and are disposable. In addition to actual pressure monitoring by gages and graphical displays etc., other pressure indicators may also be used to facilitate determining the filling status of the filling structure. For example, some embodiments may employ a relief valve. The relief valve is preset to a certain pressure such that beyond the preset pressure, any additional filling material will bleed out of the filling structure. While the relief valve may be adjacent the filling structure, preferably the filling material will be vented toward the proximal end (handle end) of the catheter, outside the body. This keeps potentially dangerous fluids or other filling material from being introduced into the body.

The methods may also include use of a pressure monitoring system that allows a physician to monitor the pressure before, during or after filling the filling structure. The system may include a user interface for displaying the pressure output and may optionally include a time output displayed in conjunction with the pressure output. The monitoring system may also include a processor for analyzing the pressure data. The processor may be programmed to normalize the pressure data. The pressure monitoring system enables the physician to closely monitor the filling pressure during deployment of the filling structure and may include additional functions to facilitate proper deployment, including: pressure cut-off switches, warning indicators if the measured filling pressure is outside an acceptable range, and pressure bleed off switches to optimize filling pressure and compensate for fluctuations in pressure during filling. The monitoring system may also record the pressure data during deployment. Additionally, in embodiments deploying two filling structures, the monitoring systems may be operatively coupled such that the system or a physician may monitor pressures during filling of one filling structure in response to pressure output readings from the other adjacent filling structures.

Pressure monitoring can also be performed at various stages of the aneurysm repair procedure to help control the filling process of the filling structure. The monitoring of pressures serves to reduce the risk of dissection, rupture or damage to the aneurysm from over pressurization and also can be used to determine an endpoint for filling. Monitoring can be done before, during or after filling and hardening of the filling structure with filling medium. Specific pressures which can be monitored include the pressure within the internal space of the filling structure as well as the pressure in the space between the external walls of the filling structure and the inner wall of the aneurysm. A composite measurement can also be made combining pressures such as those measured within the interior space of the filling structure, together with that in the space between the external walls of the structure and the aneurysm wall or other space at the aneurysm site and an external delivery pressure used by a fluid delivery device, such as a pump or syringe, to deliver the filling medium. Control decisions can be made using any one of these pressure measurements or a combination thereof Methods of pressure monitoring are discussed in detail in related commonly-owned applications: U.S. Pat. No. 7,666,220 and U.S. Patent Application No. US 20100036360 A1, the entire contents of which are incorporated herein by reference.

The pressure monitor as shown in FIG. 17 is used by an operator to monitor the filling pressure for the polymer being injected into the double wall filling structure 12. While a vacuum is initially pulled on the double wall filling structure 12, as described below, once the filling of the double wall filling structure 12 is initiated by the injection of polymer the associated pressure sensor monitor on the polymer tubing system as shown in FIG. 17 will detect the systemic blood pressure of the patient as the double walled filling structure 12 is surrounded by the patient's blood in the arterial system. As further injection of polymer progresses and any compressible fluid in the system becomes compressed (though there should be very little air or other compressible fluid in the system because a vacuum has been pulled on the system in the first step of the pressurization portion of the deployment procedure). The sensitivity of the pressure monitor to the blood pressure of the patient being treated will increase as more of the tubing system is filled with the liquid fluid (understood to be an incompressible fluid—which transmits pressure instantaneously). The system will then operate merely as a pressure sensor while the double walled filling structure 12 is unrestrained and surrounded by systemic blood pressurized in the normal manner by the patient's pulsating heart.

Pressure monitors 69, such as that shown in FIG. 17, can be programmed to display various desired systemic blood pressure specific points in the cycle of the pulsating blood pressure of a patient's normal arterial function. The high pressure being the systolic pressure and the low pressure in a cycle being the diastolic pressure. The pressure monitor, if so programmed, will provide a readout of both the systolic and diastolic pressures (two readings on one display face). The pressure monitor 69 can be reprogrammed (it's firmware adjusted) to readout specifically selected pressure parameters, e.g., the systolic pressure, the diastolic pressure, or a mean pressure (which averages the systolic pressure and diastolic pressure). The length of the sampling (averaging) time of the pressures measured and then displayed can also be adjusted in the pressure monitor 69. The averaging of each parameter over time can be taken over a selected range of seconds. For example the selected sampling ranges may be 5 seconds, 10 seconds, or 15 seconds, or other intervals desired—and available in the hardware and programmable software of the pressure monitoring device. The monitor will then update its digital display at each selected time interval. In the normal operation of deployment of the filling structure, the operator will inject polymer into the double walled filling structure pressurization system and observe the diastolic pressure of the system. The diastolic pressure will very according to system pressure (patients arterial blood pressure system pressure) until the outer wall of the double walled filling structure reaches the inner wall of the aneurysm. Simultaneously the inner wall of the double walled filling structure which is already adjacent to or situated on a support structure or endoframes (e.g., 19) will become restricted in its inward expansion as a result of resting on against the internal support structure or endoframe. Once the limits of unopposed expansion are reached, the pressure inside the double walled filling structure (endobag) will increase. A monitoring of the pressure readout on the pressure monitor programmed to present either the diastolic pressure or the mean pressure will provide information about the state of expansion of the double walled filling structure. The polymer injection/filling should continue until the diastolic (lower) pressure is increased to be equal to or below above the systolic readout so that the mean pressure and diastolic pressure readout of the pressure monitor 69 is nearly the same (in the instance where all three pressures can be read on a display or detected by various means (known to person skilled in the art) during an operation. Once the endobag reaches its full expansion (limited from further expansion by the inner wall of the aneurysm), the pressure monitor 69 will no longer be measuring the system pressure or be sensing a variation system pressure. The diastolic pressure will not vary very much and the pressure in the double walled filling structure 12 (the endobag) will be shown on the digital display 73. The target pressure for the endobag is usually at or slightly above the expected systolic pressure of the patient being treated. The pressure the systemic pressure expected to be overcome is in the range of 180 to 300 mmHg which is less than half an atmosphere (equal to 380 mmHg). Thus while the pressurization of the double walled filling structure initially reads the systemic arterial pressure, ultimately the arterial pressure is excluded and only the inner pressure of the double walled filling structure (endobag) is detected. Once the pressure inside the endobag exceeds the maximum systemic arterial pressure there is a high degree of reliability that the aneurysm is excluded and sealed. At that point further injection of the polymer will cease and possibly checking of the sealing by use of angiography can take place. There is a time duration of 5 to 10 min. from the initial injection time until the polymer becomes cured or set and during that 5 to 10 min. it may be possible to further inject polymer and detect the internal pressure of the double walled filling back 12, if necessary. These aspects may be used in any of the methods and systems described herein.

FIG. 18 illustrates and exemplary delivery system and FIGS. 19A-19C illustrate cross sections of the delivery system of FIG. 18. FIG. 19A shows cross-section A-A at a location proximal of the nosecone at which the filling structure 12, endoframe 19 and balloon 16 are each disposed concentrically outside inner shaft 17 and inside of outer sheath 40. FIG. 19B shows cross-section B-B at a location distal of the carrier knob 57 at which concentric inner and outer filling tubes 20A, 20B are disposed adjacent concentric inner and outer balloon shafts 17A, 17B of inner shaft 17 within outer sheath 40. FIG. 19C shows cross-section C-C at a location between the handle 60 and carrier knob 57 at which concentric inner and outer filling tubes 20A, 20B are disposed adjacent concentric inner and outer balloon shafts 17A, 17B of inner shaft 17 within hypotube 41. In many embodiments, the outer sheath 40 and hypotube 41 comprise different materials. For example, the distal segment of outer sheath 40 may comprise polyether block amide, while the segment of outer sheath 40 proximal of the carrier knob 57 may comprise 304 stainless steel.

FIGS. 19B and 19C also show an inner core 99 or filler that typically terminates about 2.5 cm from the proximal (illiac side) balloon bond to the balloon outer shaft. The inner core 99 is typically a filler material, often a TPE material with a hardness of 70D (durometers on the D Shore scale) or lower (e.g. Pebax 6333). The inner core 99 can be a solid of a low durometer material, such as Pebax 6333, or a pellethane may be used so long as the density of the inner core aids in pushability. The outer surface of the inner core can be smooth or textured. Surface design of the inner core can be configured to provide a desired coefficient of friction low between it and the outer sheath. The distal end of the inner core 99 stops about 2 to 2.5 cm from the balloon taper/neck transition to allow for the balloon to expand and inhibit kinking of the fill tube. This transition is typically heat formed and UV bonded to create a tapered transition and to seal the lumens to ensure no air can pass through these lumens and inhibit back bleeding. At the handle end, the inner core can terminate 1 cm into the handle hypotube or can run entirely through the handle hypotube. Ideally, at least 1 cm of the inner core extends inside the handle hypotube to ensure attachment and inhibit kinking at this location.

Delivery System Coupling Mechanisms

FIGS. 20A-20E illustrates coupling mechanisms of an exemplary delivery system. The coupling mechanisms inhibit movement of the filling structure and endoframe relative to the delivery catheter so as to facilitate positioning of the filling structure and endoframe at the aneurysm. FIG.

20A depicts the coupling mechanisms during deployment of the filling structure, wherein the outer sheath 40 has been retracted and filling structure 12 has been partially filled. The coupling mechanisms may include tethers 51,53 and/or tether loops for attaching filling structure 12 and endoframe 19 to inner shaft 17. As shown in FIG. 20A, filling structure 12 is disposed over endoframe 19 which is crimped onto expandable member 16 disposed near the distal end of inner shaft 17. Two releasable coupling mechanisms, tethers 51 and 53, along with release wire 46 inhibit movement of filling structure 12 and endoframe 19 relative to inner shaft 17 during delivery and positioning at the aneurysm.

Figure 20E:
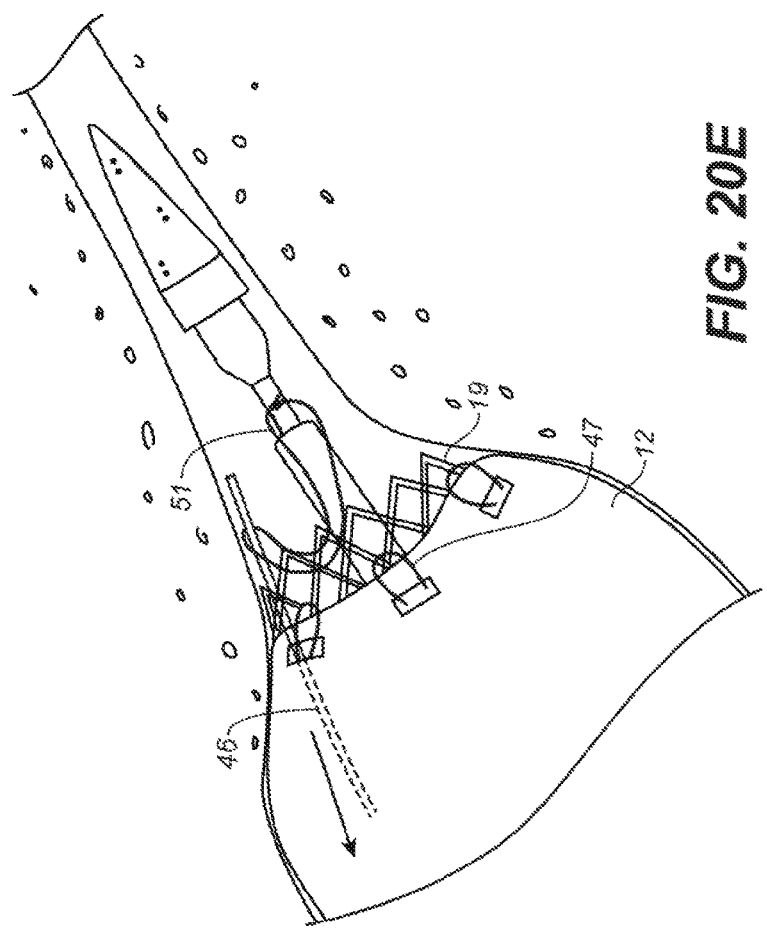
Figure 20C:
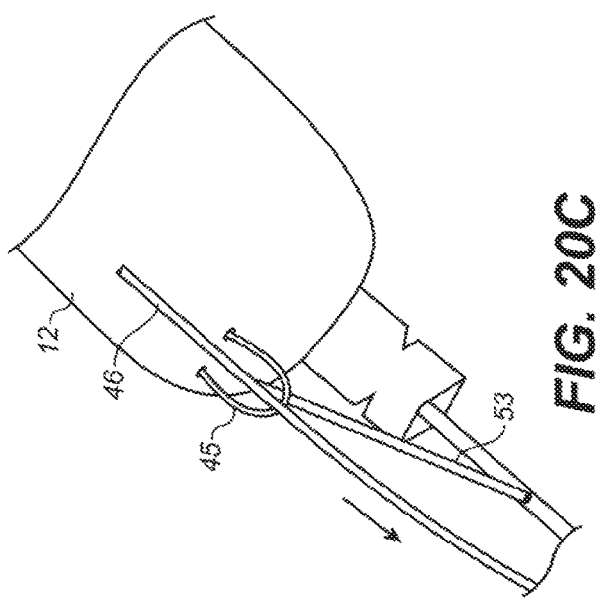
Figure 20D:
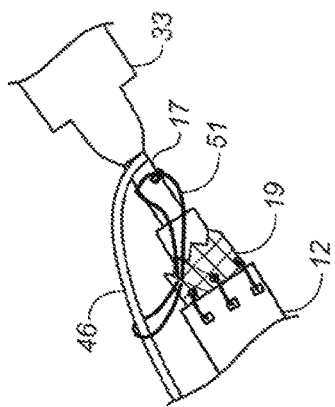

Tether 51 may comprise a tether loop fixedly attached to inner shaft 17 distal of the filling structure 12, the tether loop extending through an opening in endoframe 19 and around release wire 46, as shown in detail in FIG. 20E. Tether 51 couples the endoframe 19 to inner shaft 17 so long as release wire 46 remains within the loop of tether 51. In this embodiment, the filling structure 12 is indirectly coupled to inner shaft 17, since endoframe 19 is also coupled to the filling structure 12 with sutures 47. Once release wire 46 is withdrawn, tether loop 51 easily slips out through the opening in endoframe 19 and can be withdrawn with inner shaft 17.

Tether 53 may comprise a tether loop fixedly attached to filling tube 20, which then extends through a suture loop 45 on the proximal end of filling structure 12 and around the release wire 46. So long as release wire 46 remains within the suture loop 45, filling tube 20 remains coupled with the proximal end of filling structure 12. Tether 53 may inhibit movement of the proximal region of the filling structure 12 during delivery, and may help prevent release of the fill tube 20 from the filing structure 12. Thus, tether 53 provides a fail safe mechanism prior to filling and during filling or re-filling of the filling structure, until the procedure is over, at which time the release wire can be retracted releasing the coupling between filling tube 20 and the filling structure 12.

Once the filling structure 12 has been deployed and filled with hardenable fluid filling medium, the release wire 46 can be withdrawn by pulling the proximal end of the release wire 46 from the handle 60. After releasing the filing structure 12 and endoframe 19, the delivery system 10) can be withdrawn from the body as tether loops 51 and 53 no longer couple the filling structure 12 or endoframe 19 to the system. In an exemplary embodiment, the release wire 46 extends the length of and runs parallel to inner shaft 17. During delivery, the distal end of release wire 46 is releasably coupled to inner shaft 17 just proximal of the nosecone 33, as shown in detail in FIG. 20D. This is to ensure the release wire does not interfere with deployment of the filling structure 12. A UV adhesive, such as Loctite 3321, may be applied to hold the knot and create a temporary bond between the release wire and the inner shaft. In many embodiments, release wire 46 is Teflon coated, so that the temporary bond easily delaminates and releases from inner shaft 17 when a physician pulls the proximal end of release wire 46 at handle 60. The release wire 46 may be made from polytetrafluroroethylene coated 304 stainless steel and sized so as to be easily withdrawn from between the filling structure 12 and the endoframe 19 after deployment.

As shown in FIG. 20B, filling structure 12 is coupled with the distal end of the endoframe 19 by one or more sutures 47, preferably four sutures, disposed at regular intervals about the distal end of filling structure 12. The sutures 47 couple the filling structure 12 to endoframe 19 to maintain the relative position of the endoframe 19 during deployment and may also help anchor the filling structure 12 to the endoframe 19 after deployment of the filling structure 12 in the aneurysm. One of skill in the art will appreciate that other releasable coupling mechanisms, including releasable knots, may be used and therefore the coupling mechanism is not limited to tether embodiments. Additionally, the tether may be used as a releasable coupling mechanism in any of the embodiments disclosed in this specification.

In an exemplary embodiment, suture 47 comprises a single thread having one end attached to endoframe 19 and the other end attached to endoframe 19, as shown in FIG. 20A. Alternatively, suture 47 may comprise a suture loop, such as those depicted in FIG. 20B. Endoframe 19 may include eyelets 49 near the proximal or distal ends of the endoframe through which the suture 47 can be looped to secure the filling structure 12 to the endoframe 19. This way, the filling structure 12 will be fixed relative to the endoframe as long as the tether loops are taut. Generally, this coupling mechanism will allow about ±5 mm and more preferably ±3 mm of relative movement between the filling structure and the endoframe. Also, the filling structure and endoframe should be positionable within ±7 mm and more preferably between ±5 mm of a target position within the aneurysm of the filling structure 12. In an exemplary embodiment, the four sutures are equally distributed about the distal end of the filling structure. For example, the four sutures may be attached to the filling structure and spaced apart radially at 0 degrees, 90 degrees, 180 degrees and 270 degrees.

FIG. 21 shows an undeployed configuration of delivery catheter 14A which includes an end handle 60A and a sheath retraction knob 57A. Sheath 40A is coupled to the sheath retraction knob 57A and is configured spaced apart from the end handle 60A by a hypotube 41A. The handle 60A includes a guidewire access port 61A through which a guidewire GW is passed. Next to the guidewire access port 61A there is a release wire access and lock port and fitting 66A through which endobag pressurization piping (double wall filling structure 12) passes. One half of a quick release color-coded tubing connector 82A is connected to the catheter end of the endobag pressurization piping/tubing. Endoframe pressurization piping/tubing 68A (such as for balloon expansion within the endoframe) also passes into the handle 60A and has its catheter end connected to one half of a quick release tubing connector 84A. The handle 60A also provides routing for guidewire lumen pressurization piping/tubing 62A from one half of a quick release connector 86A at the catheter end of the tubing, to and through a tee fitting and external connection valve 75A through the tubing 62A into the handle and to the guidewire lumen connected therein. This guidewire lumen pressurization (angiography) tubing 62A and in line tee valve allow simultaneous introduction of contrast solution to both catheters or separate introduction of contrast solution to each catheter.

FIG. 22 shows the catheter 14A configured with its sheath 40A having been retracted over hypotube 41A by retracting the sheath retraction knob 57A towards the handle 60A such that the double walled filling structure 12A is exposed.

Figure 23:
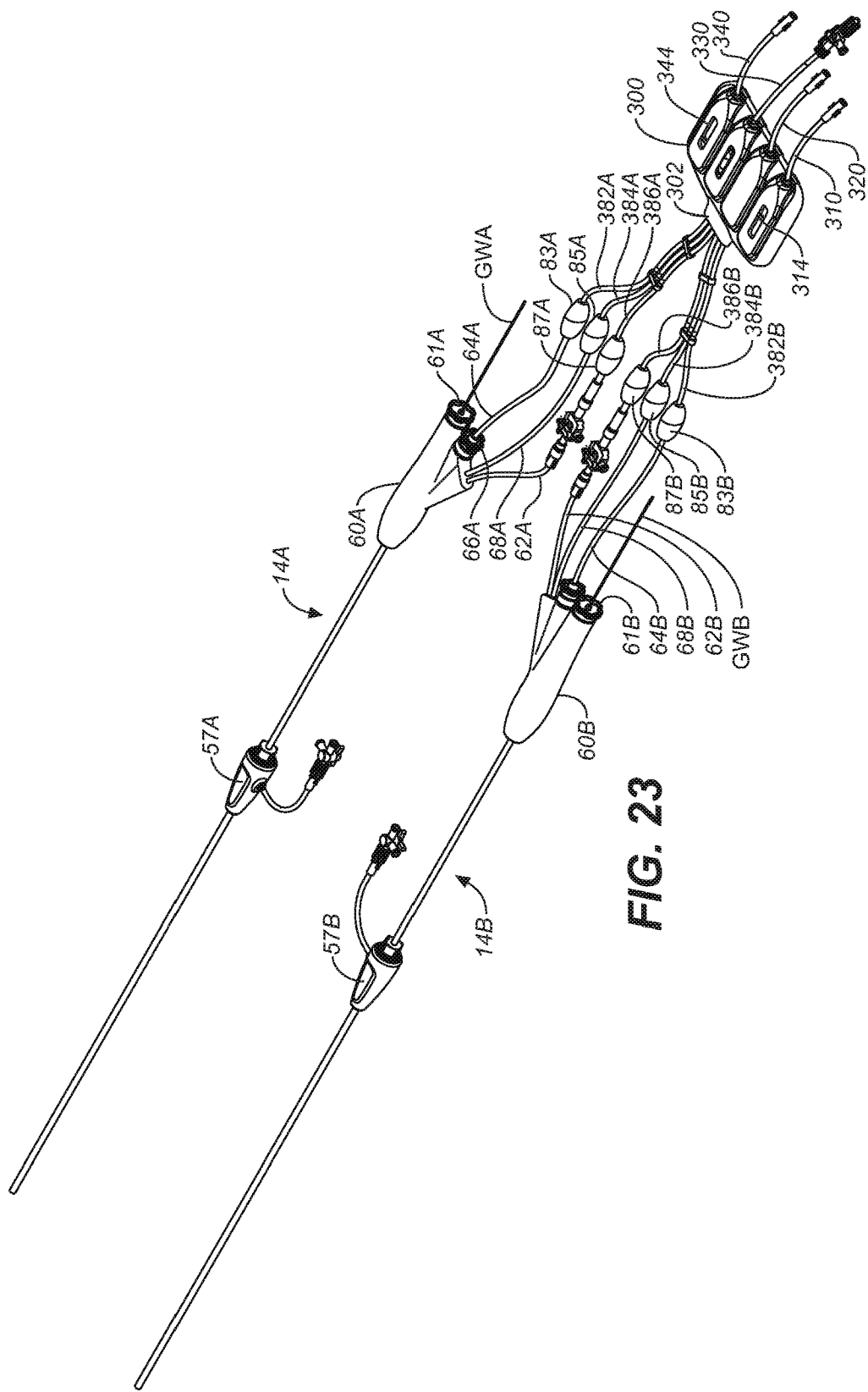
FIG. 23 is a lateral view showing two separate and discrete catheter treatment systems/devices as in FIG. 21, where filling structure fill tubing, endoframe/expansion balloon pressurization tubing, and a guidewire lumen flush or contrast solution supply tubing from each catheter is connected to a sequential deployment step indicating single operator manifold console used to simultaneously pressurize and operate the function of both catheters from one operating input and location.

FIG. 23 shows a lateral view of two separate catheters 14A and 14B configured as they would be for deployment in separate legs of a patient routed through the patient's iliac arteries up into the patient's aorta. Each catheter 14A, 14B has the tubing of its respective handles 60A, 60B connected separately to a single operator sequential manifold console 300. The single operator manifold console 300 provides an operator the convenience, time savings benefit, and deployment operation self equalizing positioning of hooking both catheters 60A, 60B up to a single pressure port to use each step of an orchestrated series of steps to centrally, simultaneously, and equally pressurize the lumens and active elements of both separate catheter systems 14A, 14B. As shown in FIG. 23, the catheter handles 60A, 60B are configured symmetrically about the manifold console 300 to be connected with their corresponding common pressure and fluid supply lines from the manifold console 300. The handle 60A of catheter 14A includes, as previously discussed, a guidewire access port 61A while the catheter 14B and its handle 60B include a guidewire access port 61B. For the catheters pictured, similar structures on catheter 14A are similarly correspondingly numbered on catheter 14B except that the "A" suffix designation with respect to the elements of catheter 14A are transformed into "B" suffix designations when identified on catheter 14B.

The single operator manifold console has piping/tubing pressure and fluid supply lines leading to each to each corresponding fluid and pressure supply line function on the respective separate catheters. One half of quick release connection fittings at the ends of the tubing lines leading from the single operator manifold console are designated 83A for the endobag pressurization piping; 85A for the endoframe pressurization piping, and 87A for the guidewire lumen pressurization piping. The respective tubing leading from the single operator sequential manifold console 300 is designated 382A, 384A, and 386A. While on the second catheter 14B, the handle 60B houses similarly functioning fluid and pressure piping/tubing and quick connectors having a second set of pressurization lines leading from the single operator manifold console to the respective functioning pressurization lines of the catheter. The endobag pressurization piping 64B is connected to the manifold console tubing 382B through quick connector quick tubing connector halves 82B, 83B while the endoframe pressurization tubing 68B is connected to single operator manifold console tubing 384B through connector halves 84B, 85B and the guidewire lumen pressurization piping 62B is connected to single operator manifold console tubing 386B through quick connector halves 86B, 87B. On the catheter side of the manifold console there are six separate tubing lines leaving the console outlet opening 302. On the operator side of the manifold console 300 there are four tubing inlet lines: for endobag deflation (negative pressurization) 310, for endoframe pressurization (expansion of balloon) 320, for endobag polymer filling (positive pressurization) 330, and guidewire lumen pressurization (angiography (contrast) supply) 340.

Figure 24:
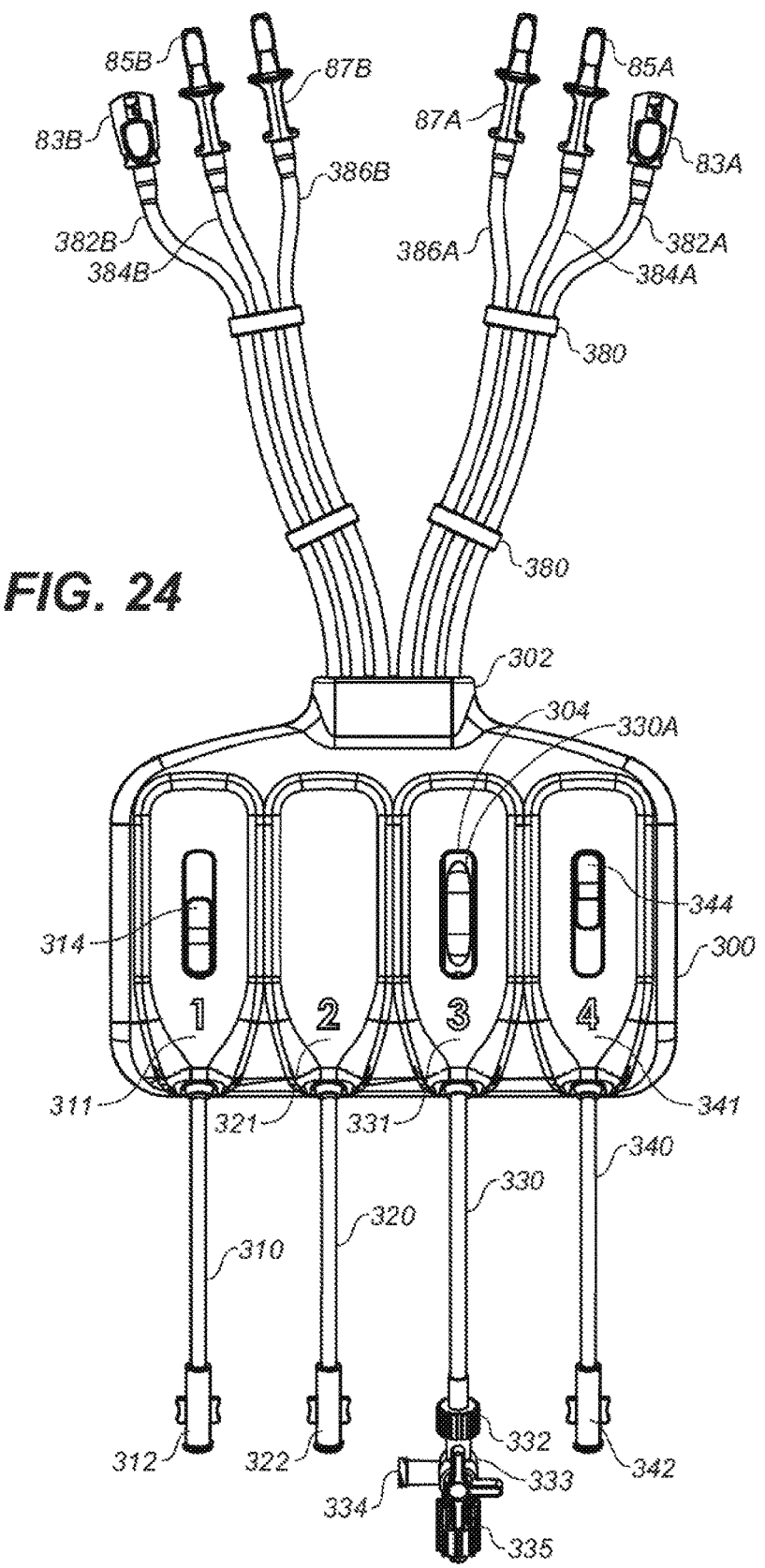
FIG. 24 is a plan view of the single operator manifold console of FIG. 23.

Referring now to FIG. 24 which shows a plan view of the single operator sequential manifold console 300 four lines leading into the operator manifold console and six lines leading out of the console. However, the configuration with only three inlet lines may be used in other applicable systems where different sequential steps are desired/defined as recommended for deployment of the treatment structures associated with two separate catheters.

Although various configurations may be used, typically, a sequential configuration, such as first, second, and third ports for example, is arranged to match a recommended sequence of an operator's steps of operation such as pressure application to: endobag pressurization tubing, endoframe pressurization tubing, and guidewire lumen pressurization tubing. Functionally, there are only three separate (function) pressurization lines from each separate catheter connected to the sequential manifold console. Therefore a most simplified hypothetical manifold configuration would have only three lines matching the three separate system (functions) pressurization lines in the catheters. A console configuration for a catheter system utilizing three sequential steps of pressure application would be configured progressively (side by side by side) with three inlet ports to match the sequential steps of a deployment procedure requiring the operator to act (apply pressure) at a first inlet port, conclude activity at the first inlet port, act at a second inlet port, conclude activity at the second inlet port, act as a third inlet port, and conclude activity at the third inlet port in a sequential stepwise fashion. However, when two pressurization (positive or negative) activities need to be performed at one inlet port non-sequentially, (e.g., another step needs to be performed between the two (or more) steps to be performed at the one inlet port) the re-application or the attachment of a pressurization source and the re-application of pressure provide a non-ideal configuration in that the complexity of executing the recommended appointment steps shifts to the operator, and the operator must be knowledgeable and familiar with the deployment procedure to recognize and act on the three ports of the console while performing four or more steps of a deployment procedure. In this instance where only three steps are to be performed on the three inlet ports sequentially, a configuration of a manifold console as shown, would provide the benefit of simultaneous pressurization of the two separate catheters and their internal separate pressurization systems each from one pressure source as described herein for the configuration of FIG. 23.

The first inlet port into the manifold console 300 on the left side as shown in FIG. 24 is the endobag vacuum function with tubing 310 having a connection fitting 312 supplying the port. A sequence indicating symbol such as a number or letter is aligned with the first and subsequent adjacent inlet ports of the console. For port one here, the sequence indicating symbol 311 is the Arabic number "one" adjacent to port one on the console. In addition, the word ENDOBAG may be listed in alignment with the first port on the face of the console. Port one also has an on-off switch/shutoff valve 314 aligned with it which can be used as a shutoff valve to close the tubing and prevent any flow to or from port one. For example when vacuum is applied to port one, and there is no indication of blood in the endobag pressurization tubing, which would mean that there is a hole in the endobag and blood is being sucked into the tubing by the application of vacuum and that a vacuum pressure attained is maintained, the valve 314 can be closed to secure the system and release the vacuum source from the vacuum tubing connector 312.

A second port leading into the operator manifold console is associated endoframe pressurization tubing 320. The port associated sequence indicating symbol 321 is the Arabic number "two" on the console. The endoframe pressurization tubing 320 has a connection fitting 322 at its end.

The third port to the manifold console 300 adjacent to and to the right of the endoframe pressurization port in relation to the endoframes inlet tubing 320, endobag pressurization (polymer feed) tubing 330 has an end connection fitting 332 to which Tee and valve combination fitting 333 is connected. The side Tee fitting connection 334 is available for and is commonly used to monitor pressure by using a pressure monitoring device such as that shown and described in and for FIG. 17. The Tee and valve combination fitting 333 includes an inlet port 335 where a filler material (such as a hardenable fluid polymer) would be attached. The use of a valve fitting provides the ability to close the inlet port to isolate the endobag pressurization system when a supply source for polymer or other filling substance is replenished or replaced at the inlet port 335. The third port designator is labeled with Arabic numeral "three." A polymer cure visual indicator window 304 in the top of the console aligned with the third port provide visual indication of the completion of the curing process for a time curing polymer or filling material. Tubing, piping, or other conduit material having light transparent, translucent, or light transmissive properties is routed between a colored surface 330A and the indicator window 304. Polymer cure completion is detectable by a user when using a polymer or other filling substance which allows the colored surface 330A to be seen through the uncured polymer and tubing when the polymer is uncured, and then partially or fully obscures light passing through to prevent observing the colored surface through the polymer when the polymer is cured, as indicated by observing the obstruction of light and/or the loss of light transmissivity through the indicator.

The fourth inlet line to the manifold console 300 adjacent and to the right of the third port in sequence, the guidewire lumen pressurization port being having inlet tubing 340 aligned with an alphanumeric designator 341 which in this instance is the Arabic number "four," 341. A guidewire lumen pressurization inlet port connector 342 is at the end of the tubing 340. A guidewire lumen pressurization port control on-off valve 344 is shown in line with the port. Such a valve prevent back leakage from blood being pressurized and finding its way through the guidewire lumen if left unchecked or may be used for angiography as described herein.

On the discharge side of the manifold console 300 the outlet opening 302 has six lines of tubing exiting. Two set of three lines of tubing are bundled by bracket connectors 380. The two bundles of lines each go to one catheter as previously discussed for FIGS. 22 and 23. The halves of the quick connect fittings at the ends of the tubing are configured to mate with complementarily matched halves of quick connect fittings on the catheters.

Figure 25:
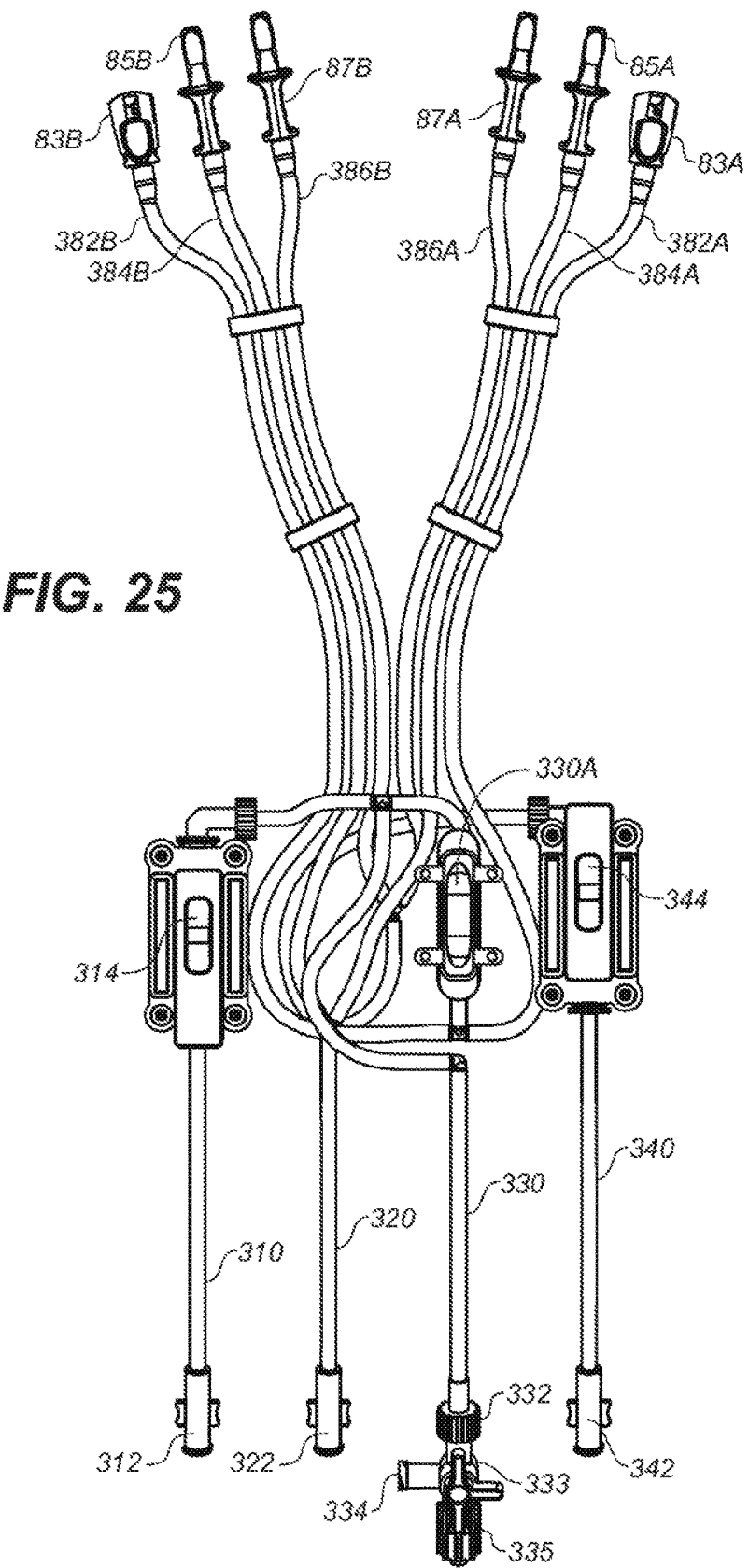
FIG. 25 is a cut-away plan view of the piping/tubing layout, showing the piping layout to, through, and out of the single operator manifold console of FIG. 24.

FIG. 25 shows an overview of all of the tubing/piping routed through the manifold console where the manifold console housing has been removed to reveal the routing of the tubing/piping. There are the four previously discussed supply lines 310, 320, 330, and 340 and the six console outlet tubing lines 382A, 384A, 386A, 386B, 384B and 382B. The endobag vacuum connection line/tubing/piping/ system is connected through on off switch/valve 314 which isolates the endobag inlet port connector 312 from the remainder of the tubing piping system. The guidewire lumen pressure supply tubing 340 is connected through the on off switch/valve 344 which isolates the angiography supply tubing which is fed into the guide wire lumens of the treatment catheters 14A, 14B. The polymer supply tubing line 330 is aligned with a polymer cure indicator window. The colored surface visual polymer siding indicator 330A reduces or eliminates the need to monitor the injection mixing and setting time for curing a polymer by providing a visual indication of successful conclusion of the treatment procedure.

Figure 26:
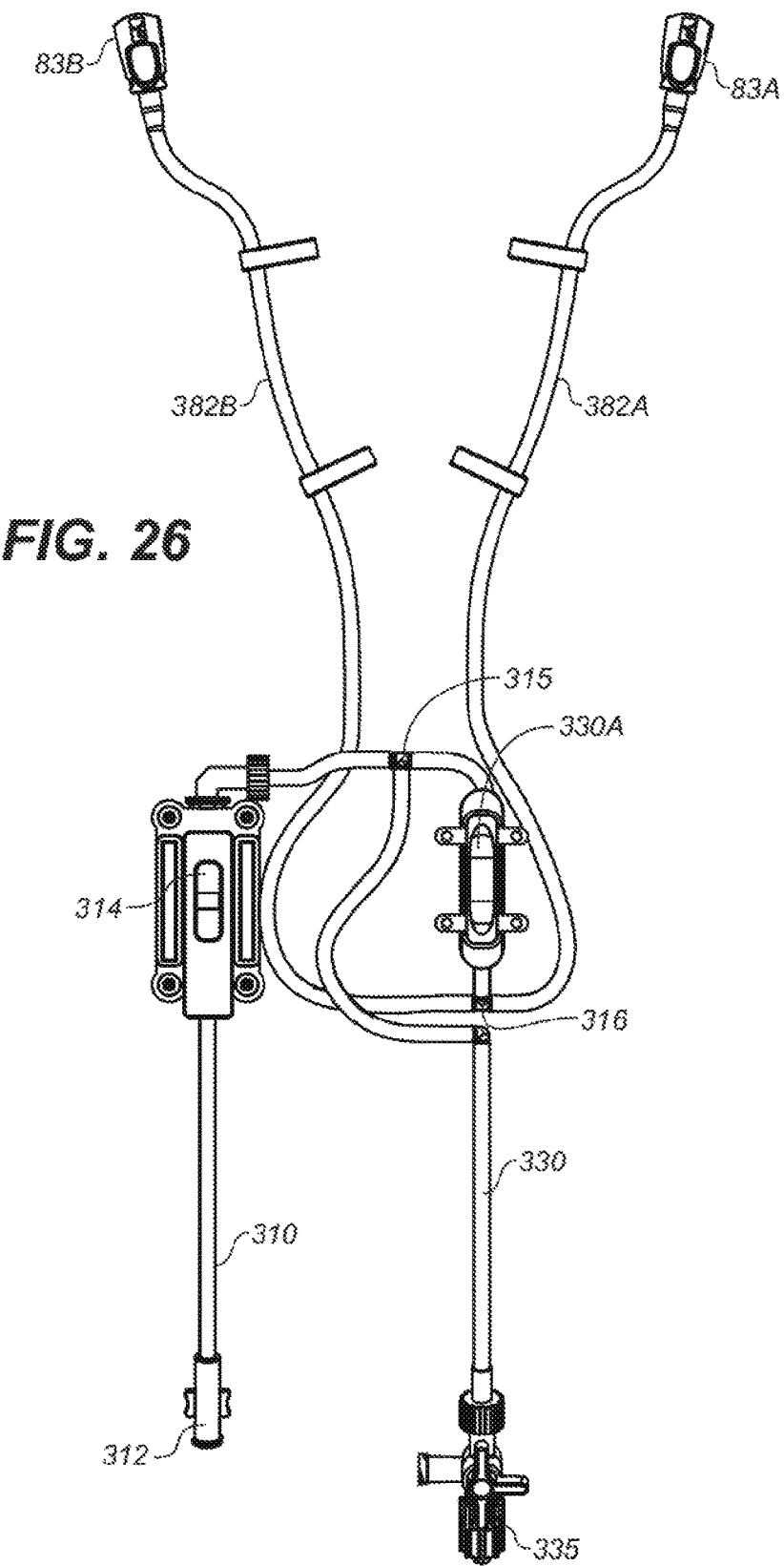
FIG. 26 is a cut-away diagram of the piping/tubing layout of the single operator manifold console of FIG. 24, isolating the piping system used for the application of vacuum to the endobag piping system.

FIG. 26 shows the vacuum connector (endobag pressurization) circuitry isolated from the other piping in the manifold console 300. A vacuum source is connected to the vacuum connector 312 thereby creating a vacuum pressure in connector line 310 sucks through the on off switch/valve 314 to reach a T connector fitting 315. The vacuum then reaches through the polymer cure indicator passage and the polymer cure indicator 330A to reach the downstream piping T connector fitting 316. The vacuum pressure is thereby distributed to the two treatment catheters through the endobag pressurization lines 382A, 382B. The quick disconnect fitting halves 83A, 83B connect to their complementary fitting halves on their respective endobag pressurization lines of the catheters. Once the endobag has been released from the sheath by retracting the sheath using the knob 57, a vacuum is pulled in the endobag piping, as the first step in the pressurization procedure to be sure that bag has no holes and its integrity is intact. Pulling a vacuum on the endobag cause any holes in the endobag to allow blood to the interior of the bag and to be sucked back through the tubing and towards the single operator manifold console. Since clear Tygon® tubing is used, the discoloration associated with a blood re-flow would be immediately apparent. Also if the tubing fails to maintain a vacuum, that would be an indication of some leakage or defect that would need to be explored further, even if blood was not immediately apparent in the tubing. Since this same tubing circuit would later be used and pressurized using the bag filling substance such as a polymer, the leakage of such filling substances from the piping system would be likely to occur at the location where a vacuum seal was not achieved during evacuation. Such leakage, while not universally catastrophic, may cause procedural delays and irregularities which might better be dealt with before the mixing and injection of pressurized expensive polymer into unknown locations by leakage from the piping system. Once the operator is satisfied that the endobags are in fact intact and sealed, the on off switch/valve 314 can be closed to isolate the endobags and maintain the vacuum while shutting off or disconnecting the vacuum source from the system and connector 312.

Figure 27:
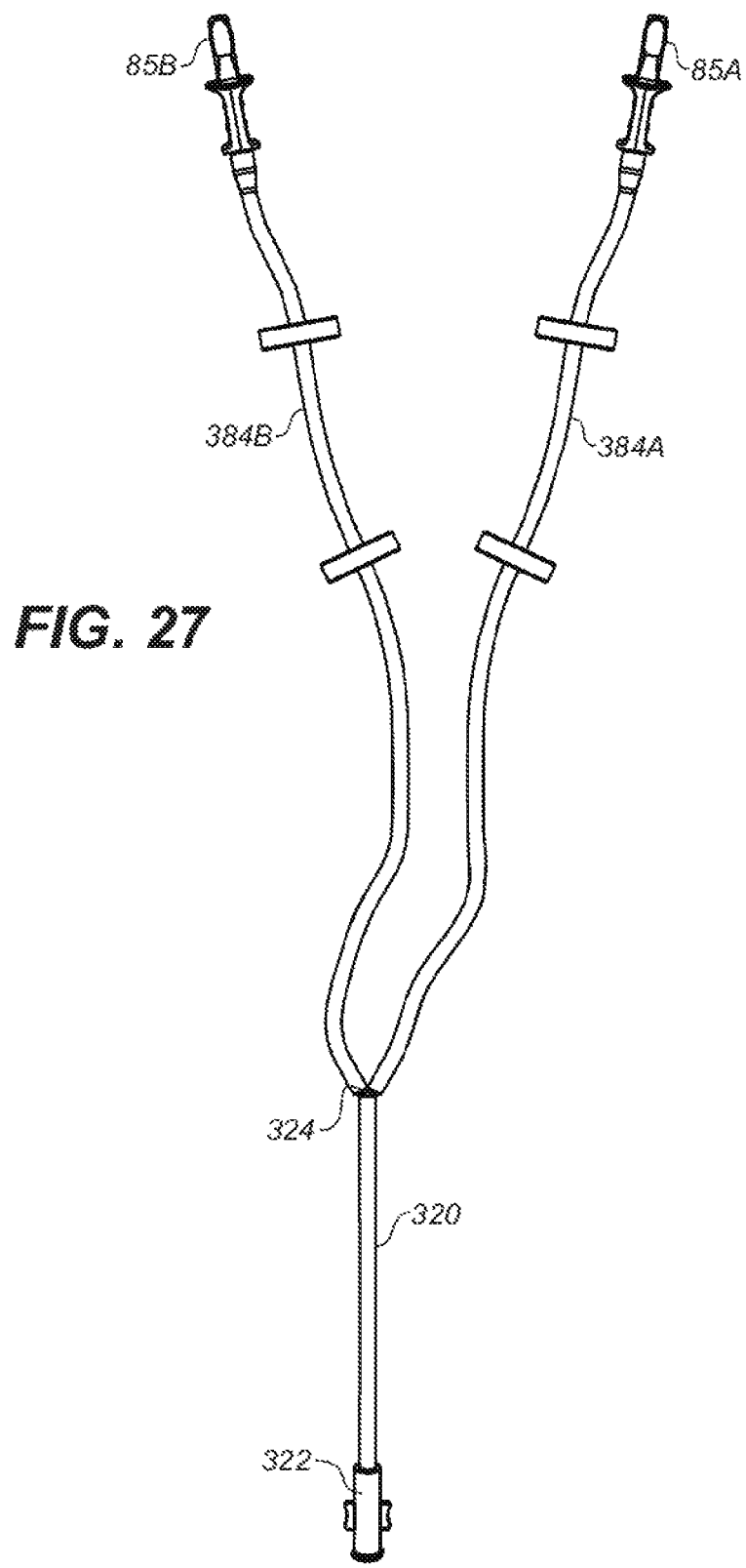
FIG. 27 is a cut-away diagram of the piping/tubing layout of the single operator manifold console of FIG. 24, isolating the piping system used for the application of pressure and vacuum to the endoframe/balloon piping/tubing system.

FIG. 27 shows an isolated view of the endoframe (balloon inflation) pressurization tubing/piping system used to expand endoframes as may be used in a treatment procedure. A pressurized fluid source is connected to the endoframe pressurization port 322 to provide fluid flow and pressure through: inflation tubing 320, a Y fitting 324, and branched into manifold console discharge tubing 384A and 384B, to reach their respective separate catheters as connected to and through their respective halves quick connect tubing/piping fittings 85A and 85B. Since the catheters inside the body are adjacent to one another spanning the aneurysm and the endoframes surrounding inflation balloons are adjacent to one another, simultaneous pressurization will equally distribute the pressure expanding the endoframes. Ideally the endoframes are expanded such that they do not distort or distend the surrounding artery wall and damage to it. Once the endoframes are fully expanded, the endoframe (balloon expanding) pressurizing fluid can be removed or aspirated allowing the balloon to collapse to allow blood to flow through the now unfilled lumen of the expanded endoframes or others support structure (when an endoframe is not used). In the instance where self-expanding endoframes are used, the tubing/piping fitting or port associated with endoframe expansion may be omitted as the retraction of the sheath, e. g., sheath 40, earlier described or other such mechanisms could be used to release the compressed frame and initiate self expansion from its compressed contracted configuration to its relaxed open (expanded) configuration.

Figure 28:
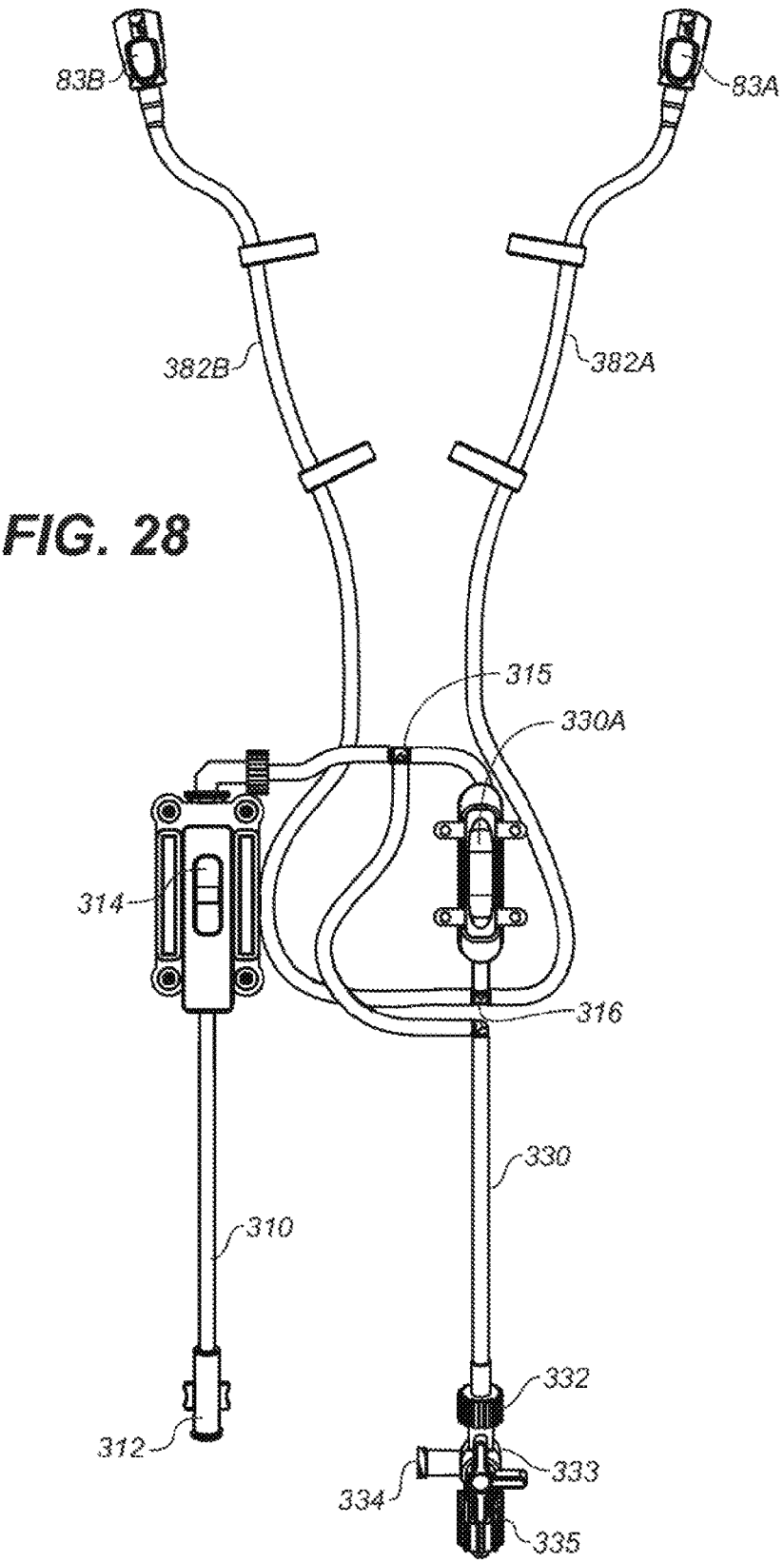
FIG. 28 is a cut-away diagram of the piping/tubing layout of the single operator manifold console of FIG. 24, isolating the piping system used for the supply of pressurized polymer through the endobag pressurization piping/tubing.

FIG. 28 shows the polymer filling piping (endobag pressurization) configuration where a polymer supply source is connected to polymer supply fitting 335. Polymer flows through the T valve combination fitting 333 through the supply tubing 330 to the T fitting 315, through the polymer cure indicator tubing 344, to the T fitting 316, from where the polymer is equally pressurized to be distributed into the aneurysmal sac filling structures of both treatment catheters through discharge tubing and 382A, 382B, and the quick connect halves 83A, 83B connected thereto and to corresponding fitting and tubing on the separates treatment catheters. The vacuum pressure which has been maintained in the piping system since the first pressurization step of the treatment process is aids in initial polymer flow until pressure is equalized in the system, then when pressurized, polymer flows freely at a rate according to the resistance that the flow encounters in passing through the feed tubes and into the endobags. Once the polymer has set the endobag pressurization the operator may turn the release wire access port 66 (such as shown in FIG. 16) on the handle of each catheter to unlock it from the respective handle 60 and pull the port 66, fill tube 64, and release wire 46 (which is locked/fixed to the port 66 to release the endobag from the catheter for subsequent catheter removal.

Figure 29:
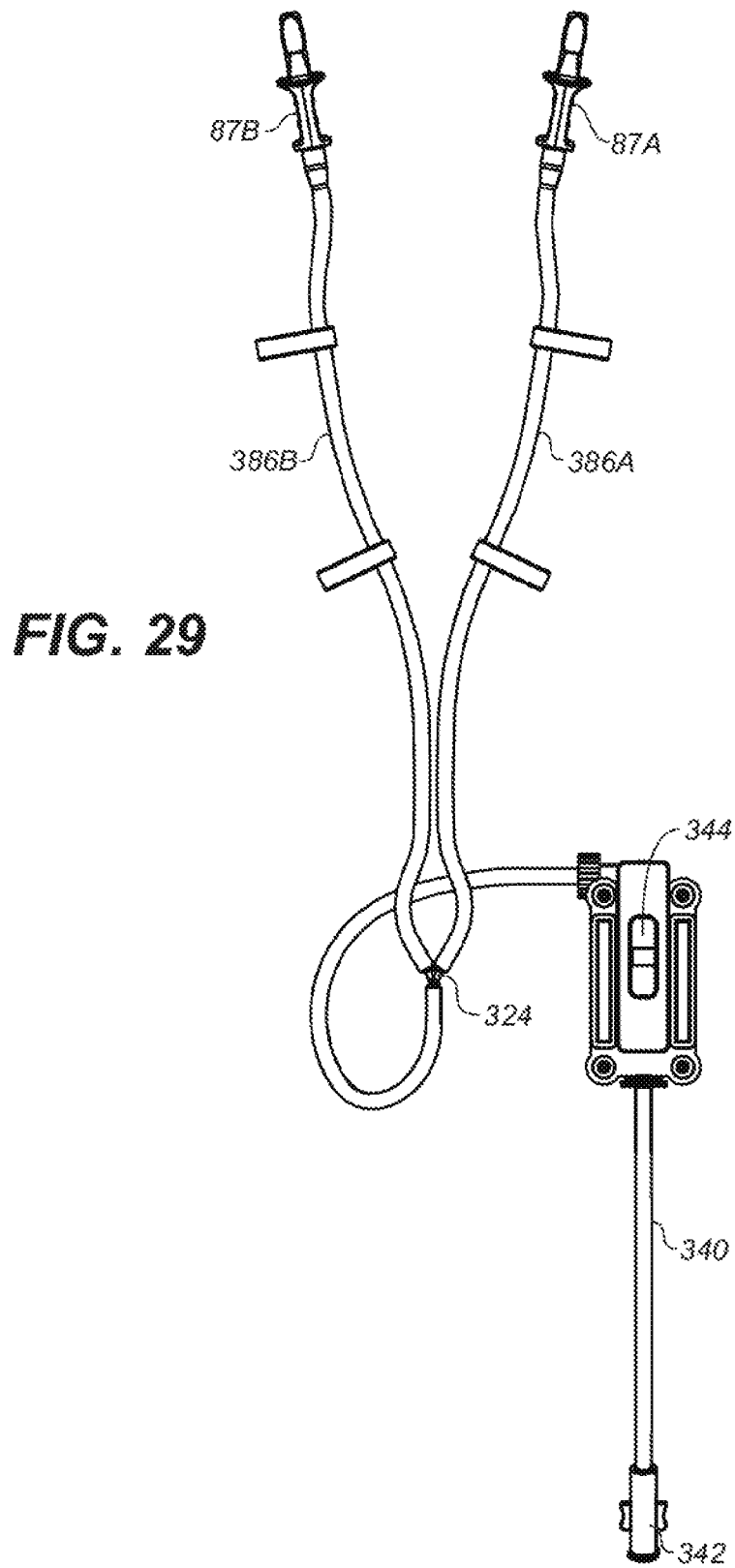
FIG. 29 is a cutaway diagram of the piping layout of the single operator manifold console of FIG. 24 showing the piping/tubing layout for the application of angiography contrast solution to the catheter treatment system through the guidewire lumen.

FIG. 29 shows the angiography/contrast supply tubing (guidewire lumen) pressurization piping. The connector fitting 342 supplies contrast flow through the inlet tube 340 and through on off switch/valve 344 to a Y fitting 346 from where it is distributed to the two treatment catheters through supply tubing 386A, 386B and quick connector halves 87A, 87B, similar to the earlier described connections as would be understood by persons skilled in the art and may be used for pressurization of the guidewire lumen and/or angiography using the guidewire lumen as described herein.

While the above is a description of the embodiments, various alternatives, modifications, and equivalents may be used. For example, although the manifold console is described throughout as a single operator sequential manifold that allows a single user to operate the systems described herein, one of skill in the art would appreciate that various manifold consoles would be within the spirit and scope of the invention as described herein. The various features of the embodiments disclosed herein may be combined or substituted with one another. Therefore, the above description should not be taken as limiting in scope of the invention which is defined by the appended claims.

The invention claimed is:

1. A system for treating an aneurysm comprising:
a first catheter and a second catheter each catheter having an endobag comprising a double-walled filling structure with an aneurysm conforming outer wall and a blood transit lumen creating an inner wall surrounding an endoframe releasably coupled to the respective catheter,
each of the first and second catheters includes an endobag pressurization piping having one end releasably coupled to the respective endobag and an inner lumen in communication with the respective endobag with the other end of the respective endobag pressurization piping in communication with an endobag pressurization tubing outside the respective catheter,
each of the first and second catheters includes a balloon on which the respective endoframe is mounted so as to expand the endoframe when inflated, each balloon being in communication with an endoframe pressurization tubing outside of the respective catheter, and
each of the first and second catheters comprises a guidewire lumen in communication with a guidewire lumen pressurization tubing extending outside the respective catheter; and
a manifold console having two endobag pressurization tubing outlet ports, two endoframe pressurization tubing outlet ports, and two guidewire lumen pressurization outlet ports, the two endobag pressurization tubing outlet ports being connectable to the corresponding ends of the endobag pressurization tubing of the endobags of the first and second catheters, the two endoframe pressurization tubing outlet ports being connectable to the corresponding ends of the endoframe pressurization tubing of the first and second catheters, and the two guidewire lumen pressurization outlet ports being connectable to the corresponding ends of the guidewire lumen pressurization tubing of the first and second catheters;
the manifold console further having a series of inlet ports including a first inlet port in communication with the two endobag pressurization tubing outlet ports, a second inlet port in communication with the two endoframe pressurization tubing outlet ports, and a third inlet port in communication with the two guidewire lumen pressurization outlet ports,
the manifold console being configured so that when the endobag pressurization and endoframe pressurization tubing ends from the first and the second catheters are connected to the corresponding manifold console outlet ports pressurization of the first inlet port equally pressurizes corresponding endobag pressurization tubing to both the first and second catheters simultaneously and pressurization of the second inlet port equally pressurizes corresponding endoframe pressurization tubing to both the first catheter and the second catheter simultaneously.

2. The system of claim 1 wherein the first, second, and third inlet ports are configured in a sequential configuration to provide operator guidance and to retain balanced pressurization between the first and second catheters, where the sequential configuration of first, second, and third ports is arranged to match a desired sequence of an operator's steps of pressure application to the first and second catheter endobag pressurization, endoframe pressurization, and guidewire lumen pressurization tubings.

3. The system of claim 1, wherein the manifold console includes a fourth inlet port, which is also in communication with the endobag pressurization piping in the manifold console, where the fourth port is not located adjacent the first inlet port.

4. The system of claim 3, wherein the manifold console includes a fourth inlet port flow valve which when closed prevents flow between the endobag pressurization piping in the sequential manifold console and the fourth inlet port.

5. The system of claim 3, wherein the manifold console includes a third inlet port flow valve which when closed prevents flow between a guidewire lumen pressurization piping in the sequential manifold console and the third inlet port.

6. The system of claim 1, wherein the manifold console is configured to distribute pressure of a flowable polymer which is curable in situ that is supplied to through the first inlet port to facilitate concurrent filling of two endobags in situ through the endobag pressurization tubing.

7. The system of claim 6, wherein the flowable polymer has a density in the range from 0.1 gm/cc to 5 gm/cc when hardened.

8. The system of claim 6, wherein the filling pressure is in the range from 100 mm Hg to 330 mm Hg.

9. The system of claim 6, further comprising a polymer cure indicator so as to indicate to a user when the flowable polymer has reached a desired cure state.

10. A manifold console
comprising: two endobag pressurization tubing outlet ports;
two endoframe pressurization tubing outlet ports; and
two guidewire lumen pressurization outlet ports, wherein at least one of the two ports are connectable to an end of corresponding pressurization tubing outside of each of a first catheter and a second catheter;

the manifold console further having a series of inlet ports that include a first inlet port that communicates with the two endobag pressurization tubing outlet ports, a second inlet port that communicates with the two endoframe pressurization tubing outlet ports, and a third inlet port that communicates with the two guidewire lumen pressurization outlet ports, the corresponding manifold console outlet ports being connectable to the corresponding pressurization tubing ends comprising corresponding endobag pressurization tubing, corresponding endoframe pressurization tubing and corresponding guidewire lumen pressurization tubing of the first and the second catheters, wherein the manifold console is configured such that pressurization of the first inlet port equally pressurizes the corresponding endobag pressurization tubing to both the first catheter and the second catheter simultaneously and pressurization of the second inlet port equally pressurizes the corresponding endoframe pressurization tubing to both the first catheter and the second catheter simultaneously.

11. The manifold console of claim 10 wherein the first, second, and third inlet ports are arranged to match a sequence of an operator's steps of pressure application to the connectable first and second catheter endobag pressurization, endoframe pressurization, and guidewire lumen pressurization tubing.

12. The manifold console of claim 10, wherein the sequential manifold console includes a fourth inlet port, which is also in communication with the endobag pressurization piping in the manifold console, where the fourth port is not located adjacent the first inlet port.

13. The manifold console as in claim 12, wherein the sequential manifold console includes a fourth inlet port flow valve which when closed prevents flow between the endobag pressurization piping in the sequential manifold console and the fourth inlet port.

14. The manifold console as in claim 10, wherein the sequential manifold console includes a third inlet port flow valve which when closed prevents flow between the guidewire lumen pressurization piping in the sequential manifold console and the third inlet port.

15. The manifold console of claim 10, wherein the manifold console is configured to retain balanced pressurization between the first and second catheters, the sequential configuration of first, second, and third ports.

16. The manifold console of claim 10, wherein the manifold console is configured to distribute pressure of a flowable polymer which is curable in situ that is supplied to through the first inlet port to facilitate concurrent filling of two endobags in situ through the endobag pressurization tubing.

17. The manifold console of claim 16, wherein the polymer comprises a polyurethane, a polyethylene glycol, or a collagen.

18. The manifold console of claim 16, wherein the flowable polymer has a density in the range from 0.1 gm/cc to 5 gm/cc when hardened.

19. The manifold console of claim 16, wherein the filling pressure is in the range from 100 mm Hg to 330 mm Hg.

20. The manifold console of claim 16, further comprising a polymer cure indicator so as to indicate to a user when the flowable polymer has reached a desired cure state.

* * * * *